(12) United States Patent
Kmak et al.

(10) Patent No.: US 11,684,297 B2
(45) Date of Patent: Jun. 27, 2023

(54) SHEATH FOR A MEDICAL DEVICE

(71) Applicant: ViOptix, Inc., Newark, CA (US)

(72) Inventors: Stephen Matthew Kmak, Santa Clara, CA (US); Robert J. Campbell, Jr., Nashua, NH (US); Robert James Mosley, San Jose, CA (US); Mark Gil Martin, Hayward, CA (US); William Welch, Sunnyvale, CA (US); Richard W. O'Connor, Atherton, CA (US)

(73) Assignee: ViOptix, Inc., Newark, CA (US)

( * ) Notice: Subject to any disclaimer, the term of this patent is extended or adjusted under 35 U.S.C. 154(b) by 174 days.

(21) Appl. No.: 17/146,182

(22) Filed: Jan. 11, 2021

(65) Prior Publication Data

US 2021/0212583 A1     Jul. 15, 2021

Related U.S. Application Data

(60) Provisional application No. 62/959,764, filed on Jan. 10, 2020.

(51) Int. Cl.
*A61B 5/1455*     (2006.01)
*A61B 5/00*       (2006.01)
*A61B 50/30*      (2016.01)
*A61B 50/00*      (2016.01)

(52) U.S. Cl.
CPC .......... *A61B 5/14551* (2013.01); *A61B 5/742* (2013.01); *A61B 50/30* (2016.02); *A61B 2050/0066* (2016.02); *A61B 2050/0067* (2016.02); *A61B 2050/314* (2016.02); *A61B 2562/247* (2013.01)

(58) Field of Classification Search
CPC ... A61B 5/145; A61B 5/1455; A61B 5/14551; A61B 5/14552; A61B 5/742; A61B 2562/247; A61B 50/00; A61B 50/30
See application file for complete search history.

(56) References Cited

U.S. PATENT DOCUMENTS

| | | |
|---|---|---|
| 5,517,301 A | 5/1996 | Dave |
| 5,619,992 A | 4/1997 | Guthrie et al. |
| 6,516,209 B2 | 2/2003 | Cheng et al. |
| 8,233,955 B2 | 7/2012 | Al-Ali et al. |
| 8,750,954 B2 | 6/2014 | Petersen et al. |
| 8,798,700 B1 | 8/2014 | Heaton, II et al. |
| 9,398,870 B2 | 7/2016 | Bechtel et al. |
| 10,722,156 B2 | 7/2020 | Lonsinger et al. |

(Continued)

OTHER PUBLICATIONS

International Search Report, PCT Application PCT/US2021/012996, dated Mar. 24, 2021, 7 pages.

*Primary Examiner* — Chu Chuan Liu
(74) *Attorney, Agent, or Firm* — Aka Chan LLP

(57) ABSTRACT

A sheath for an oximetry device includes a top and a body where the top opens to provide an opening where the oximetry device can be placed into the body of the sheath. The top of the sheath can be closed onto the body and the closure of the top can be verified by circuits in the oximetry device. The circuits can monitor the position of a latch that is connected to the top of the sheath. The circuits can determine when the latch is unlatched and the top is open and not sealed closed to the body. And, the circuits can determine when the latch is latched and the top is closed and sealed to the body.

13 Claims, 34 Drawing Sheets

(56) References Cited

U.S. PATENT DOCUMENTS

| | | | |
|---|---|---|---|
| 2005/0143675 A1* | 6/2005 | Neel | A61B 5/15117 600/583 |
| 2006/0169607 A1* | 8/2006 | Carnevali | G06F 1/1626 206/320 |
| 2010/0030020 A1* | 2/2010 | Sanders | A61B 1/00105 600/109 |
| 2013/0150729 A1 | 6/2013 | Zuluage | |
| 2017/0303833 A1 | 10/2017 | Lonsinger et al. | |

* cited by examiner

SHEATH FOR A MEDICAL DEVICE

CROSS-REFERENCE TO RELATED APPLICATIONS

This application claims the benefit of U.S. patent application 62/959,764, filed Jan. 10, 2020. This application is incorporated by reference along with all other references cited in these applications.

BACKGROUND OF THE INVENTION

The present invention relates generally to optical systems that monitor parameters related to oxygen levels in tissue. More specifically, the present invention relates to optical probes, such as compact, handheld oximeters, and sheaths for the optical probes that shield the optical probes from contaminants during use and communicate status information to the optical probes regarding contaminant protection so that the optical probes are reusable.

Oximeters are medical devices used to measure the oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for a marathon); and veterinary purposes (e.g., animal monitoring).

In particular, assessing a patient's oxygen saturation, at both the regional and local level, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply. Tissue oximeters can measure oxygen levels in human tissue by exploiting these light-absorption differences.

Human tissue, as an example, includes a variety of light-absorbing molecules. Such chromophores include oxygenated hemoglobin, deoxygenated hemoglobin, melanin, water, lipid, and cytochrome. Oxygenated and deoxygenated hemoglobins are generally the dominant chromophores in tissue for much of the visible and near-infrared spectral range. Light absorption differs significantly for oxygenated and deoxygenated hemoglobins at certain wavelengths of light.

Despite the success of existing oximeters, there is a continuing desire to improve oximeters by, for example, improving the reuse of oximeters; reducing or eliminating contamination during use; improving remote communication; improving measurement accuracy; reducing measurement time; lowering cost through reuse; reducing size, weight, or form factor; reducing power consumption; and for other reasons, and any combination of these.

Therefore, there is a need for improved tissue oximetry devices and methods of shielding oximetry devices during use for reuse of the devices.

BRIEF SUMMARY OF THE INVENTION

Embodiments relate to compact, handheld oximeters and sheaths that house and shield the handheld oximeters from patient contact and contaminants during use and shield patients from contaminants on the handheld oximeters. Because a handheld oximeter is located in a sheath and cannot contaminate patient tissue, the handheld oximeter can be reused.

In an implementation, a housing for an oximeter device places forces on the oximeter device when the oximeter device is enclosed in the sheath. The force is transferred through the housing so that the force is applied by a probe face of the device onto a sensor window of the sheath. The force facilitates even pressure between the probe face and sensor window so that reliable oximetry measurements may be made by the oximetry device.

The housing includes a lid where the lid includes a first open end and a first closed end that is located opposite to the first open end on the lid. The first closed end includes a first window. The housing includes a body where the body includes a second open end and a second closed end that is located opposite to the second open end on the body. The second closed end includes a second window. The housing includes a hinge where the hinge hinge-couples the lid and body of the housing. The lid includes a back portion proximal to the hinge, and a front portion distal from the hinge and the back portion. The lid includes a pad coupled to an inside surface of the lid at the back portion of the lid. The lid includes a latch coupled to the lid at the front portion of the lid. The pad is a first distance from the hinge, the latch is a second distance from the hinge, and the first distance is less than the second distance.

In an implementation, a sheath includes a top and a body where the top opens to provide an opening where a handheld oximeter can be placed into the body of the sheath. The top of the sheath can be closed onto the body and the closure of the top can be verified by circuits in the handheld oximeter. The circuits can monitor the position of a latch that is connected to the top of the sheath and can latch to the sheath or can monitor the position of a latch that is connected to the sheath and can latch to the top. The circuits can determine when the latch is unlatched and the top is open and not sealed closed to the body. And, the circuits can determine when the latch is latched and the top is closed and sealed to the body.

In an implementation, a sheath communicates sheath status information to a handheld oximeter to verify that the sheath is a validated sheath that is permitted to operate in combination with the handheld oximeter. A validated sheath having a known and trusted configuration facilitates the reuse of a handheld oximeter because the oximeter is known to remain free of contaminants during the use of the oximeter. The communication between the sheath and handheld oximeter can be wireless using near-field communication (NFC) devices and NFC communication protocols or other circuit types and other communication protocols.

The sheath can include windows that allow light from a handheld oximeter to pass through the windows during the use of the oximeter. A first window can be proximate to a display of the handheld oximeter so that the display can be viewed by a user during use. A second window can be proximate to a probe face of a handheld oximeter so that the oximeter can emit light into tissue and collect the light after reflection from the tissue so that oximetry measurements can be made for the tissue. The windows are sealed to the sheath and keep the handheld oximeter from becoming contaminated during use.

The handheld oximeters implementations are entirely self-contained, without any need to connect, via wires or wirelessly, to a separate system unit for making oximetry measurements. The sources and detectors of the oximetry device are arranged in an arrangement having various source-detector pair distances that allow for robust calibration, self-correction, and oximetry measurements (such as spatially-resolved spectroscopy) in a compact probe. Other source-detector arrangements are also possible.

In an implementation, the handheld oximeter is a tissue oximeter that can measure oxygen saturation without requiring a pulse or heartbeat. A tissue oximeter of the invention is applicable to many areas of medicine and surgery, including plastic surgery. The tissue oximeter can make oxygen saturation measurements of tissue where there is no pulse; such tissue, for example, may have been separated or partially separated from the body (e.g., a flap) and will be transplanted to another place in the body. The tissue oximeter can also make oxygen saturation measurements of tissue where there is a weak pulse, such as where perfusion is relatively low.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
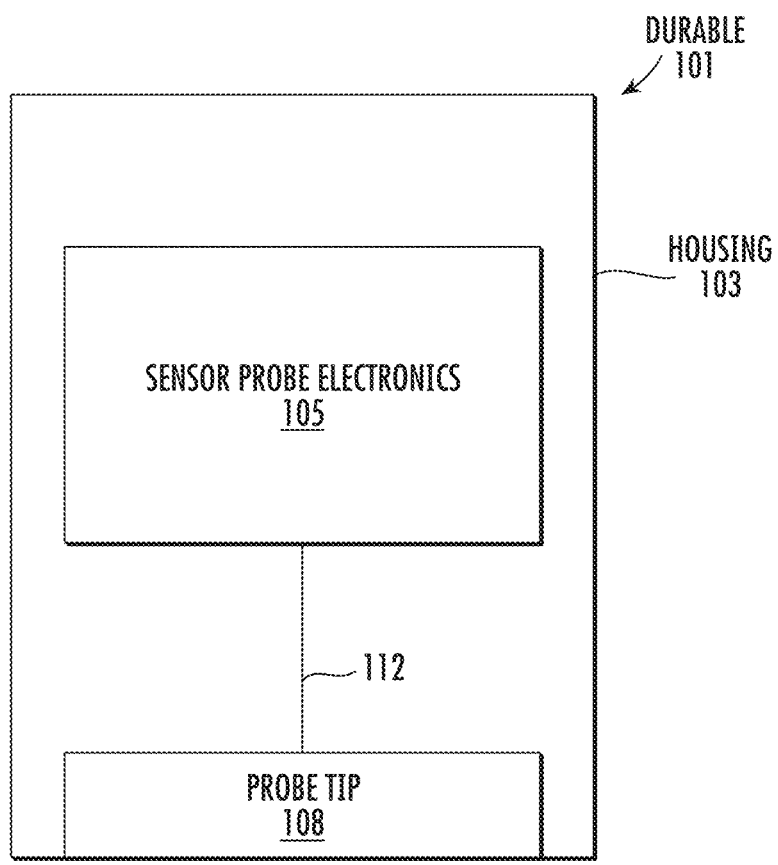
FIG. 1 shows a block diagram of a system unit for measuring various oximetry parameters of patient tissue.

Spectroscopy has been used for noninvasive measurements of various physiological properties in animal and human subjects. Visible (e.g., red light, green light, or both) and near-infrared spectroscopy is often utilized because physiological tissues have relatively low scattering in these spectral ranges. Human tissues, for example, include numerous light-absorbing chromophores, such as oxygenated hemoglobin, deoxygenated hemoglobin, melanin, water, lipid, and cytochrome. The hemoglobins are the dominant chromophores in tissue for much of the visible and near-infrared spectral range and via light absorption, contribute to the color of human tissues. In the visible and near-infrared range, oxygenated and deoxygenated hemoglobins have significantly different absorption features. Accordingly, visible and near-infrared spectroscopy has been applied to exploit these different absorption features for measuring oxygen levels in physiological media, such as tissue hemoglobin oxygen saturation (sometimes referred to as oxygen saturation) and total hemoglobin concentrations.

Various techniques have been developed for visible and near-infrared spectroscopy, such as time-resolved spectroscopy (TRS), frequency-domain techniques such as phase modulation spectroscopy (PMS), and continuous wave spectroscopy (CWS). In a homogeneous and semi-infinite model of physiological media, both TRS and PMS have been used to obtain the absorption coefficients and the reduced scattering coefficients of the physiological medium by use of the photon diffusion approximation, Monte Carlo models, or other techniques. From the absorption coefficients at multiple wavelengths, concentrations of oxygenated and deoxygenated hemoglobins can be determined and from these concentrations, the tissue oxygen saturation can be calculated.

Spatially-resolved spectroscopy (SRS) is one type of visible and near-infrared spectroscopy that allows tissue absorption to be determined independently from tissue scattering, thereby allowing absolute measurements of chromophore concentrations, such as oxygenated and deoxygenated hemoglobins. More specifically, an SRS instrument may emit light into tissue through a light source and collect the diffusely reflected light at two or more detectors positioned at different distances from the light source.

Alternatively, an SRS instrument may emit light from two or more light sources positioned at different distances from one or more detectors. Scattering of light back to the detectors is caused by relative changes of the index of refraction of the tissue and includes Mie scattering from larger structures such as mitochondria (the majority of tissue scattering is a result of mitochondria) and Rayleigh scattering from smaller structures such as intracellular vesicles. Absorption of light is caused by interaction with the tissue's chromophores.

From the reflectance (i.e., the recovered light intensity), which is recovered as a function of distance (e.g., multiple discrete distances of light detectors) from the light source, an SRS instrument can quantify the absorption coefficient and the scattering coefficient of the tissue at a single wavelength.

Multiple wavelengths of light can then be used with SRS to determine oxygenated and deoxygenated hemoglobin concentrations, and therefore, oxygen saturation within the volume of the tissue probed. Further, the wavelengths of the light source or light sources and the relative positions of the light source(s) with respect to a single detector or multiple ones of the detectors, allow tissue oximetry measurements to be made for a predetermined tissue depth. In an embodiment, one or more of the light sources and one or more of the detector source may emit and detect light so that oximetry measurements may be made for one or more predetermined tissue depths.

One field in which visible and near-infrared spectroscopy, such as SRS, is useful is in tissue flap surgery in which a tissue flap is moved from one location on a patient to another location for reconstructive surgery. Visible and near-infrared spectroscopy techniques can be used to measure oxygen saturation in a tissue flap so that the viability of the tissue flap can be determined in surgery and after surgery. Intraoperative tissue flap oximetry probes that employ visible and near-infrared SRS should be able to quickly deliver accurate oxygen saturation measurements under a variety of non-ideal conditions.

Oximetry probes adapted for SRS and other spectroscopies can come into contact with tissue, other surfaces, fluids (both liquid and gas), or other elements that can contaminate the probes. An oximetry probe that contacts tissue, for example, can be contaminated by the tissue, bacteria on the tissue, viruses on the tissue, tissue fluid, debris on the tissue, the environment near the tissue, any one of these substances, other substances, or any combination of these substances. A sheath can shield an oximetry probe from contaminants, but the efficacy of a sheath can be compromised in a number of ways. The ways in which a sheath can be compromised, allowing an oximetry probe to be contaminated, can be known and unknown. For example, a sheath housing an oximetry device may open and allow contaminants to contact the oximetry probe. The sheath opening may be relatively small and not detectable by visual inspection and the small opening may allow contaminants to enter the sheath and contact the oximetry probe. The efficacy of a sheath can be compromised if the sheath has been previously used and the previous use is unknown. The efficacy of a sheath can also be compromised if the sheath is provided from an unknown source and the sterility or sanitation of the sheath is unknown. Either inside or outside surfaces of the sheath, or both, can be contaminated if the sheath is provided by an unknown source. If the previous use of a sheath is unknown and the sheath is reused, contaminants on the sheath from an initial use can be spread during subsequent use of the sheath. Sheaths and the oximetry probes in the sheath may be contaminated in a variety of other ways. Reuse of an oximetry probe after contamination may be precluded or may increase the cost of reuse due to the cost of sanitizing or sterilizing the oximetry probe. Oximetry probes and sheaths of the present invention are directed toward improved sanitation, sterilization, or both.

FIG. 1 shows a system unit 101 for measuring various parameters of tissue in a patient. System unit 101 is sometimes referred to as a durable system unit because the unit is reusable, such as when the unit is used in combination with a protective sheath. The parameters of the tissue measured by the system unit may include an oxygen saturation level (relative oxygen saturation, absolute oxygen saturation, or both), a total hemoglobin concentration, an oxygenated hemoglobin concentration, an deoxygenated hemoglobin concentration, blood flow, pulse rate, a signal level of light reflected from the tissue, melanin concentration of tissue, homogeneity of a tissue quality, other tissue parameters, or any combination of the parameters. The system unit includes housing 103, sensor probe electronics 105, and a probe tip 108, which is connected to the sensor probe electronics via a wired connection 112. Connection 112 may be an electrical connection, an optical connection, or another wired connection including any number of wires (e.g., one, two, three, four, five, six, or more wires or optical fibers), or any combination of these or other types of connections. In other implementations, connection 112 may be a wireless connection, such as via a radio frequency (RF) or infrared (IR) connection.

Typically, the system unit is used by placing the probe tip in contact with tissue (e.g., skin) or close proximity to tissue (e.g., an internal organ that is located inside of a body) at a site where tissue parameter measurements are desired. The system unit causes an input signal to be emitted by the probe tip into the tissue (e.g., human tissue). There may be multiple input signals, and these signals may have varying or different wavelengths of electromagnetic radiation. The intensity of the emitted wavelengths of radiation may be time modulated by a digital-to-analog converter that is coupled between the processor and the LEDs. The intensity of the radiation may be sinusoidally modulated, square wave modulated, or modulated by another function. The processor may transmit a digital sinusoidal signal to the digital-to-analog converter, which converts the signal into an analog signal that is transmitted to the LEDs. Sinusoidal light that is emitted and detected can be correlated so that the detected light can be discriminated from background light that generally has a constant intensity relative to the modulated light. The input signal is transmitted into the tissue and reflected from the tissue, absorbed by the tissue, or transmitted through the tissue.

Then, after transmission through the tissue or reflection from the tissue, the signal is received at the probe tip. This received signal is received and analyzed by the sensor probe electronics. Based on the received signal, the sensor probe electronics determine various parameters of the tissue, such as an oxygen saturation level, a total hemoglobin concentration, an oxygenated hemoglobin concentration, an deoxygenated hemoglobin concentration, a blood flow, a pulse, a signal level of light reflected from the tissue, melanin concentration of tissue, other tissue parameters, or homogeneity of any one or more of these parameters. One or any combination of these parameters can be displayed on a display screen of the system unit.

In an implementation, the system unit is a tissue oximeter, which can measure oxygen saturation and hemoglobin concentration, without requiring a pulse or heartbeat. A tissue oximeter of the invention is applicable to many areas of medicine, surgery (including plastic surgery and spinal surgery), post-surgery, athlete monitoring, and other uses. The tissue oximeter can make oxygen saturation and hemoglobin concentration measurements of tissue where there is no pulse, such as tissue that has been separated from the body (e.g., a tissue flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation, such as discussed in U.S. Pat. Nos. 6,516,209, 6,587,703, 6,597,931, 6,735,458, 6,801,648, and 7,247,142. There are various implementations of systems and techniques for measuring oxygen saturation, such as discussed in U.S. patent applications 62/959,757, 62/959,778, 62/959,787, 62/959,795, and 62/959,808, filed Jan. 10, 2020; Ser. No. 17/146,176, 17/146,186, 17/146,190, 17/146,194, 17/146,197, and 17/146,201, filed Jan. 11, 2021; and Ser. No. 29/720,112, 29/720,115, 29/720,120, and 29/720,122, filed Jan. 9, 2020. These patent applications are incorporated by reference along with all other references cited in these applications.

Figure 2:
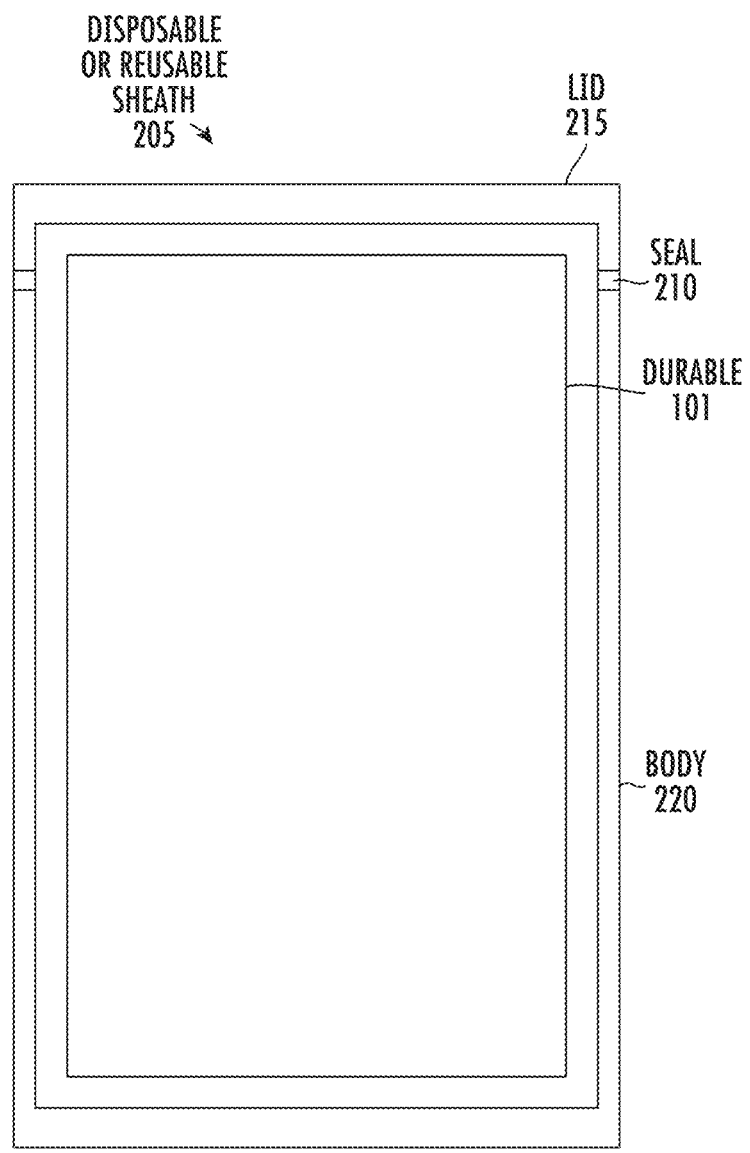
FIG. 2 shows a block diagram of the system unit housed in a sheath.

FIG. 2 shows system unit 101 housed in a sheath 205. The sheath includes a lid 215 and a body 220, which may be sealed to the lid via a seal 210. The lid may be separable from the body or may be connected to the body, such as via a hinge. The hinge may allow the lid to rotate to seal the lid to the body. The sheath may be a disposable sheath or a sheath that is reusable. For example, the system unit and sheath may travel with a patient from surgery (e.g., use) to post-surgery (e.g., reuse) for tissue monitoring.

With the lid opened, the system unit may be inserted into the sheath, and thereafter the lid may be sealed to the body to house and seal the system unit in the sheath. The system unit may then be used to make tissue parameter measurements in the sealed environment provided by the sheath. The sheath can protect a patient from contacting contaminants on the system unit, and the sheath can protect the system unit from contacting elements that the sheath contacts, such as tissue, tissue fluid, biological agents (e.g., bacteria, viruses, prions, and pyrogens), pyrogens, debris, and other contaminants. When the lid is open and the seal is broken, the system unit may be removed from the sheath. Because the system unit is sealed into the sheath by the body, lid, and seal, the system unit can remain relatively clean, sanitized, or sterile for reuse. The sheath can also protect the tissue of a patient from contacting elements that are on a system unit that is inside the sheath. For example, the sheath can prevent patient tissue from contacting bacteria, viruses, prions, pyrogens, other contaminants, or any one of these contaminants that might be on the system unit.

The sheath can also protect the tissue of a patient from contacting elements that are on a system unit that is inside the sheath. The sheath can prevent patient tissue from contacting bacteria, viruses, prions, pyrogens, other contaminants, or any one of these contaminants that might be on the system unit from passing through the sheath seal and contacting patient tissue.

Figure 3:
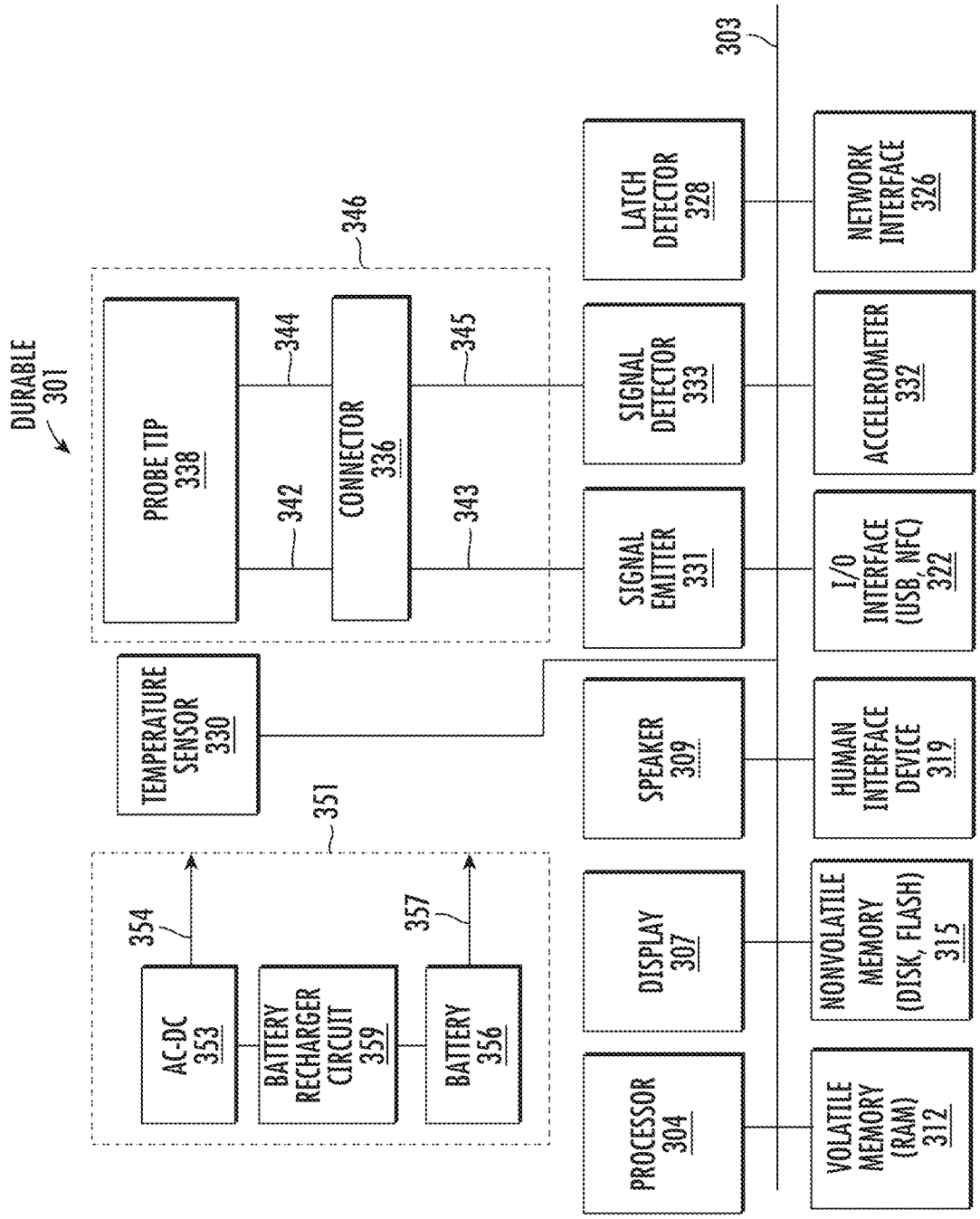
FIG. 3 shows a block diagram of the system unit, in an implementation.

FIG. 3 shows a block diagram of system unit 301, in an implementation. The system unit includes a processor 304, display 307, speaker 309, signal emitter 331, signal detector 333, volatile memory 312, nonvolatile memory 315, human interface device (HID) 319, input-output (I/O) interface 322, network interface 326, latch detector 328, temperature sensor 330, and accelerometer 332. These components are housed within housing 103. Different implementations of the system may include any number of the components described, in any combination or configuration, and may also include other components not shown.

The components are linked together via a bus 303, which represents the system bus architecture of the system unit. Although FIG. 3 shows one bus that connects to each component of the system unit, bus 303 is illustrative of any interconnection scheme that links the components of the system unit. For example, one or more bus subsystems can interconnect one or more of the components of the system unit. Additionally, the bus subsystem may interconnect components through one or more ports, such as an audio port (e.g., a 2.5-millimeter or 3.5-millimeter audio jack port), a universal serial bus (USB) port, or other port. Components of the system unit may also be connected to the processor via direct connections, such as direct connections through a printed circuit board (PCB).

In an implementation, system unit 301 includes a sensor probe 346. The sensor probe includes a probe tip 338 and a connector 336. The probe tip is connected to the connector via a first communication link 342 and a second communication link 344. First communication link 342 may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The second communication link may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The electrical wire or sets of electrical wires of the first communication link, the second communication link, or both can include one or more electrical traces on a printed circuit board.

The connector connects (e.g., removably connects) the probe tip, the wires, waveguides, or any combination of these elements to the signal emitter and signal detector of the system unit. For example, a communication link 343 may connect the signal emitter to the connector and a communication link 345 may connect the signal detector to the connector. Each of the communication links 343 and 345 may include an electrical wire, a set of electrical wires (e.g., a ribbon cable) one waveguide, a set of waveguides, a wireless communication link, or any combination of these links. Each communication link can also include one or more electrical traces on a printed circuit board. For example, the connector may include one or more connectors that are mounted on a PCB. Communication links 342, 344, or either one of these links may be ribbon cables that connect to the probe tip and connect to connectors mounted on a PCB. In this implementation, communication links 343 and 345 can be electrical traces on the PCB that link to the single emitter, signal detector, or both. In this implementation, the signal emitters and signal detectors may be electrical emitters and detectors that control light emitters, light detectors, or both in the probe tip.

In an implementation, where the probe tip is separable from the system unit 301, connector 336 may have a locking feature, such as an insert connector that may twist or screw to lock. If so, the connector is more securely held to the system unit and it will need to be unlocked before it can be removed. This will help prevent the accidental removal of the probe tip from the system unit.

The connector may also have a first keying feature, so that the connector can only be inserted into a connector receptacle of the system unit in one or more specific orientations. This will ensure that proper connections are made.

The connector may also have a second keying feature that provides an indication to the system unit of a type of probe (e.g., a probe from many different types of probes) that is attached. The system unit may be adapted to make measurements for a number of different types of probes. When a probe is inserted in the system unit, the system uses the second keying feature to determine the type of probe that is connected to the system unit. Then the system unit can perform the appropriate functions, use the appropriate algorithms, or otherwise make adjustments in its operation for the specific probe type.

In an implementation, the connector and system unit are communicatively coupled (e.g., wired or wirelessly) to transmit and receive information regarding the type of probe being attached to the system unit. The connector and system unit may be electrically coupled by electrical connectors or by radio frequency circuits. For example, the connector and system unit may each include a near field communication device that transmits and receives information for the type of probe being attached to the system unit. Then the system unit can perform the appropriate functions, use the appropriate algorithms, or otherwise make adjustments in its operation for the specific probe type.

In an implementation, signal emitter 331 includes one or more light sources that emit light at one or more specific wavelengths. In a specific implementation, the light sources emit five or more wavelengths of light (e.g., 730 nanometers, 760 nanometers, 810 nanometers, 845 nanometers, and 895 nanometers). Other wavelengths of light are emitted by the light sources, including shorter and longer wavelengths of light in other implementations. The signal emitter may include one or more laser diodes or one or more light emitting diodes (LEDs). In an implementation, a light source is a multispectral light source and a detector is a spectrometer detector.

In an implementation, signal emitter 331 is an emitter that emits electrical signals to one or more light sources, which may emit light based on the received electrical signals. In some implementations, the signal emitter includes one or more light sources and electrical signal emitters that are connected to the light sources.

In an implementation, signal detector 333 includes one or more photodetectors capable of detecting the light at the wavelengths produced and emitted by the signal emitter. In another implementation, the signal detector 333 is an electrical signal detector that detects electrical signals generated by one or more photodetectors. In another implementation, the signal detector includes one or more photodetectors and one or more electrical detectors that are connected to the photodetectors.

In an implementation, HID 319 is a device that is adapted to allow a user to input commands into the system unit. The HID may include one or more buttons, one or more slider devices, one or more accelerometers, a computer mouse, a keyboard, a touch interface device (e.g., a touch interface of display 307), a voice interface device, or another HID.

In an implementation where the HID is an accelerometer and the system unit is a handheld unit, the accelerometer may detect movements (e.g., gestures) of the system unit where the system unit may be moved by a user. Movements may include a left movement, right movement, forward movement, back movement, up movement, down movement, one or more rotational movements (e.g., about one or more axes of rotation, such as the x-axis, y-axis, z-axis, or another axis), any combinations of these movements, or other movements.

Information for the various movements detected by the accelerometer may be transmitted to the processor to control one or more systems of the system unit. For example, an upward movement (e.g., a lifting movement) may be transmitted to the processor for powering on the system unit. Alternatively, if the system unit is set down and left unmoved for a predetermined period of time, then the processor may interpret the lack of movement detected by the accelerometer as a standby mode signal and may place the system unit in a standby power mode (a lower power mode than a normal operation mode where oximetry measurements can be made by the system unit), or a power-down signal and may power down the system unit. In an embodiment, movements detected by the accelerometer are used by the process for making mode changes, state changes in a state based method (i.e., state machine). For example, a detected movement of the accelerometer may be used by the system unit to place the system unit in an averaging mode, exit the averaging mode, place the system unit in a melanin concentration detection mode, exit the melanin concentration mode, enter or exit a low power mode, a sleep mode, a power down mode, or other mode.

When the system unit is powered on, information for a left movement or a right movement detected by the accelerometer and transmitted to the processor may be used by the processor to control the system unit. For example, a left or right movement of the system unit may be used by the processor to change menu items displayed on the display. For example, the processor may use the information for a left movement to scroll menu items on the display to the left (e.g., scroll a first menu item left and off of the display to display a second menu item on the display). The processor may use the information for a right movement of the system unit to scroll menu items to the right (e.g., scroll a first menu item right and off of the display, and display a second menu item on the display).

The HID and processor may be adapted to detect and use various movements to activate a menu item that is displayed on the display. For example, information for an upward movement or a downward movement may be detected and used to activate a menu item that is displayed on the display. For example, if a user is prepared to take an oximeter measurement and a menu option is displayed for taking an oximeter measurement, a quick downward movement of the system unit may start a measurement when the probe tip is placed in contact with tissue.

The HID may include one or more accelerometers to detect motion in various directions (e.g., linear, rotational, or both). The accelerometers can include one or more capacitive micro-electro-mechanical system (MEMS) devices, one or more piezoresistive devices, one or more piezoelectric devices, or any combination of these devices.

In an embodiment, accelerometer 332 is adapted to detect relatively high G-force accelerations associated with a shock that the system unit experiences. The shock may be from bumping the system into something, dropping the system unit (e.g., dropping the system unit on a table or the floor), or other shock events. In an implementation, if the accelerometer indicates to the processor that a shock event has occurred, the processor can take a number of actions. For example, the processor can shut down the system unit. The processor can display one or more messages on the display. The messages may indicate that the system unit should be checked for operability or fore recalibrated. The message may indicate that contact between the system unit and the sheath should be checked. The accelerometer may include one or more capacitive micro-electro-mechanical system (MEMS) devices, one or more piezoresistive devices, one or more piezoelectric devices, or any combination of these devices.

In an implementation, the latch detector 328 is adapted to detect whether a latch of the sheath is latched or unlatched. If the latch is latched (e.g., latched and detected as being latched), then the system unit is housed and enclosed in the sheath. In this configuration, with the system unit housed and enclosed in the sheath, the system unit may not be contaminated by material contacting the outside surface of the sheath. If the latch is unlatched and the system unit is in the sheath, then the system unit might be contaminated with material contacting the outside surface of the sheath. That is, the seal that seals the lid of the sheath to the body of the sheath may be unsealed (i.e., opened) and contaminates may pass from outside of the sheath to the inside of the sheath where the system unit is located.

In an implementation, at least a first portion of the latch is metal. Other portions of the latch may be metal or other material, such as a plastic material. The first portion of the latch is a first distance from the latch detector when the latch is latched and is a second distance from the latch detector when the latch is unlatched. The first distance is less than the second distance.

In an implementation, the latch detector includes an inductor that can inductively couple to the first portion of the latch. The inductor can be driven with a direct current or an alternating current and thus detect when the first portion of the latch as the portion moves toward the latch detector or away from the latch detector. The latch detector can be calibrated so that the latch detector can detect when the latch moves to the first distance away from the latch detector or farther than the first distance away from the latch detector. The latch detector can include an analog-to-digital converter, a digital signal processor (DSP), or both that digitize and analyze the current flowing through the inductor. One or both of these circuits can communicate the digitalized information to the processor that can determine whether the latch is open or closed. The processor can display a message on the display to indicate whether the latch is open or closed, whether the seal for the sheath is sealed or unsealed, warn of potential contamination, or other messages associated with the latch being opened or closed.

The latch detector can be a binary detector that detects when the latch is opened or closed. The latch detector can send a first of the two binary signals to the processor to indicate that the latch is open and a second of the two binary signals to the processor to indicate that the latch is closed.

In an embodiment, the latch detector is a capacitive detector that can capacitively couple to the latch. The capacitive detector can detect the latch in the latched position at a first distance from the capacitive detector and moving away from the latched position and the first distance. In an embodiment, the latch detector is a magnetic detector that can magnetically detect that the latch is latched. That is, the magnetic detector can detect the latch in the latched position at a first distance from the magnetic detector and moving away from the latched position and the first distance. In an embodiment, the latch detector is a mechanical detector, such as a mechanical interlock.

The nonvolatile memory 315 may include a FLASH memory, other nonvolatile solid-state storage (e.g., USB flash drive), battery-backed-up volatile memory, tape storage, reader, and other similar media, and combinations of these. In some implementations, the nonvolatile memory includes a mass disk drive, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc). The volatile memory may include a random access memory (RAM).

The processor may include a microcontroller, a microprocessor, an application specific integrated circuit (ASIC), programmable logic (e.g., field programmable gate array), or any combination of these circuits. The processor may include multiple processors or a multicore processor, which may permit parallel processing of information.

In an implementation, the system unit is part of a distributed system. In a distributed system, individual systems are connected to a network and are available to lend resources to another system in the network as needed. For example, a single system unit may be used to collect results from numerous sensor probes at different locations.

Aspects of the invention may include software executable code, firmware (e.g., code stored in a read only memory (ROM) chip), or both. The software executable code or firmware may embody algorithms used in making oxygen saturation measurements of the tissue. The software executable code or firmware may include code to implement a user interface by which a user uses the system, displays results on the display, selects or specifies parameters that affect the operation of the system, or execute algorithms and calculations to generate a result.

The software executable code or firmware may include code to set the operational configuration of various mode of the system unit, such as placing the system unit in a calibration mode, use mode, run a background mode (such as a measurement averaging mode, a temperature control mode, or other background modes), lookup table modes, or other modes.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, MATLAB (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows XP, Windows XP x64 Edition, Windows Vista, Windows CE, Windows 7, Windows 8, Windows 10, Windows Mobile), Linux, HP-UX, UNIX, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may communicate with other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or another device (e.g., a laptop computer, smartphone, or personal digital assistant), a user accesses the system unit of the invention through a network such as the Internet. The user will be able to see the data being gathered by the system unit. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
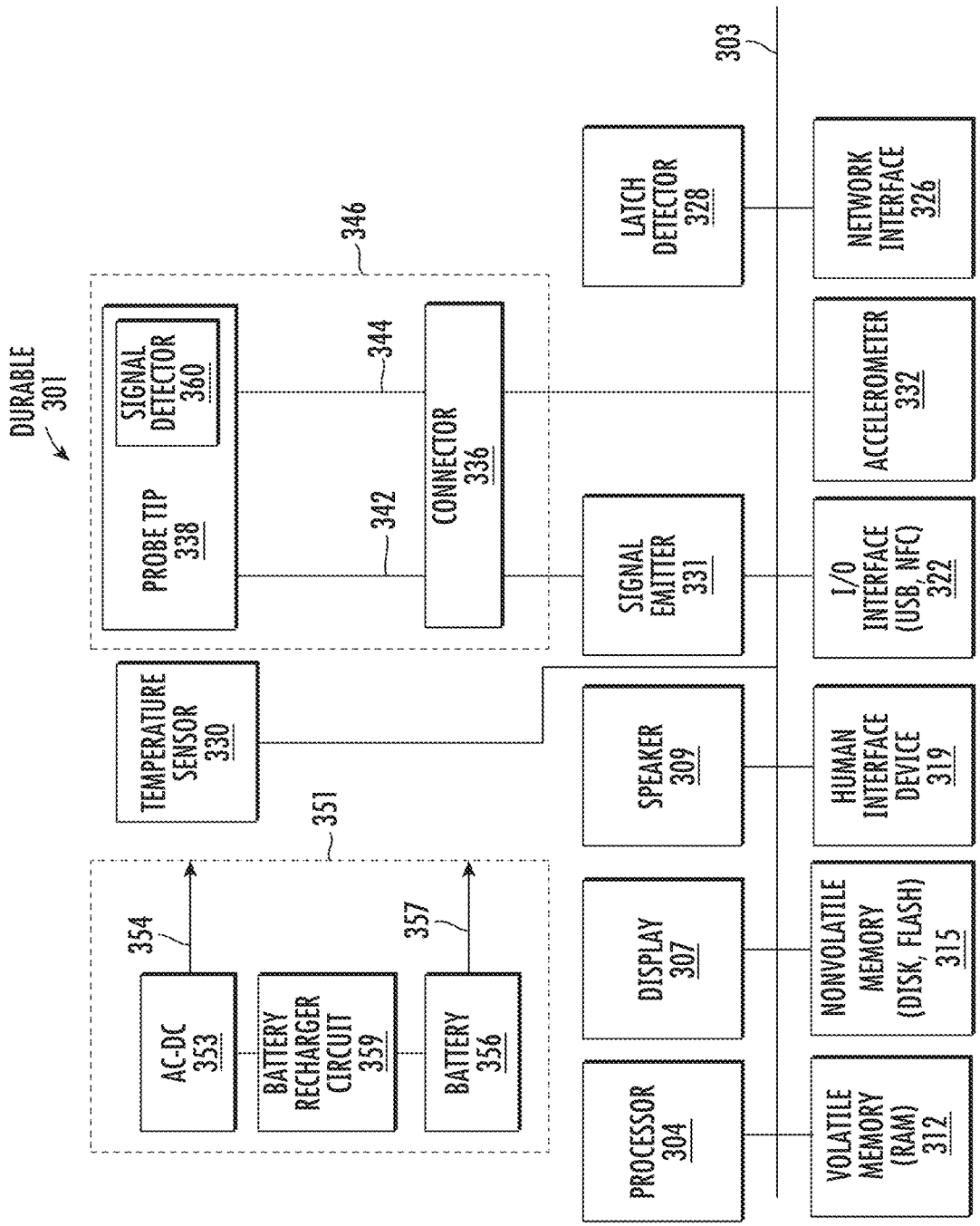
FIG. 4 shows a block diagram of the system unit, in an implementation.

FIG. 4 shows a block diagram of system unit 401, in an implementation. System unit 401 is similar to system unit 301 but differs in that the signal detector 344 is located in probe tip 346. A wire or set of wires (e.g., a ribbon cable) may connect the signal detector to the bus and processor. For example, a ribbon cable that is connected to the signal detector may also be connected to a connector or socket mounted on a PCB that the processor and other circuits are mounted on. The signal detector may be located at a probe face of the probe tip. The signal emitter may be optically located behind the probe face of the probe tip.

Figure 5:
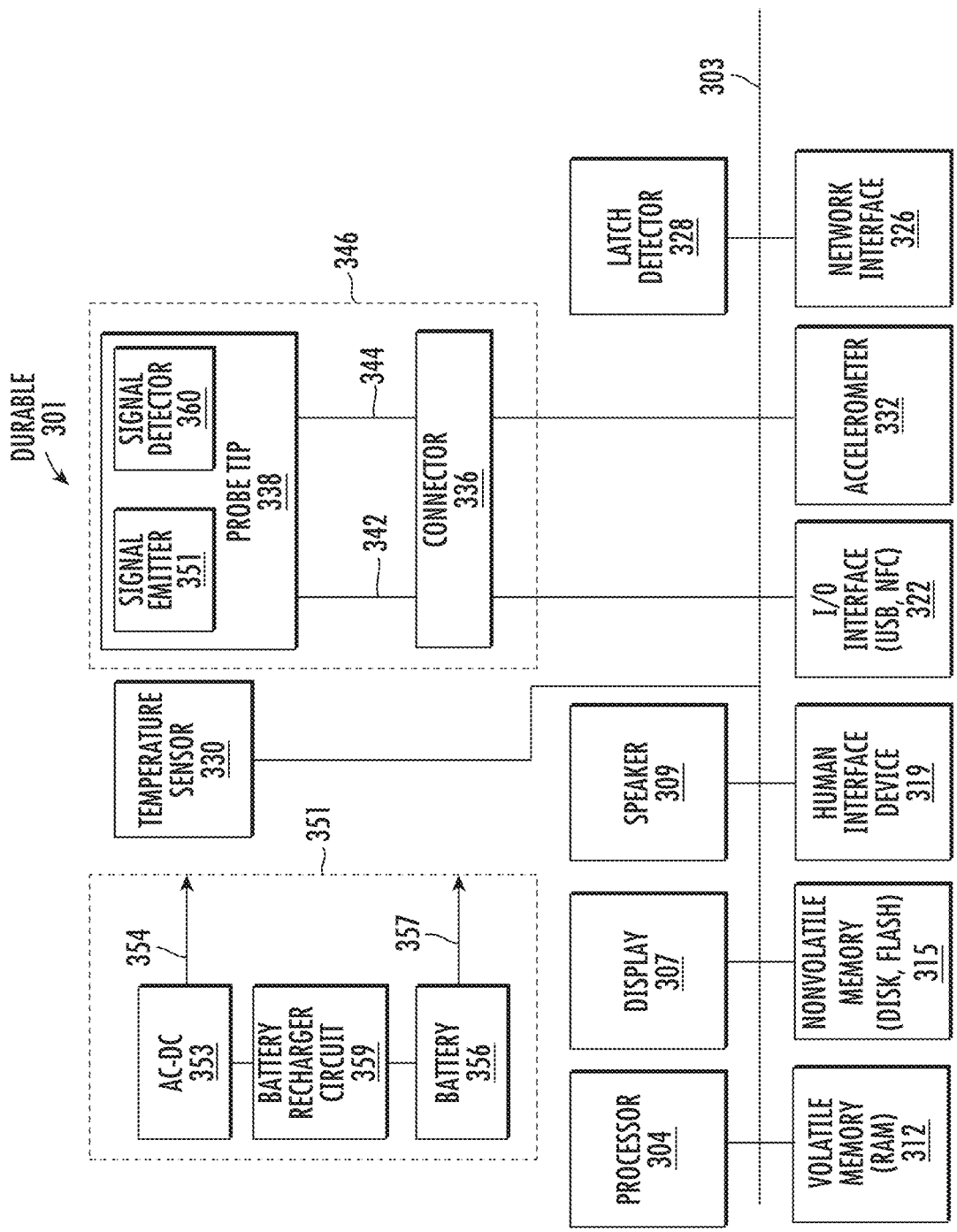
FIG. 5 shows a block diagram of the system unit, in an implementation.

FIG. 5 shows a block diagram of system unit 501, in an implementation. System unit 501 is similar to system units 301 and 401 but differs in that the signal emitter 331 and the signal detector 344 are located in probe tip 346. A wire or wires (e.g., one or more ribbon cables) may connect the signal emitter, the signal detector, or both to the bus and processor. A first ribbon cable may connect the signal emitter to the bus and processor and a second ribbon cable may connect the signal detector to the bus and processor. For example, the first ribbon cable that is connected to the signal emitter may also be connected to a connector or socket mounted on a PCB that the processor and other circuits are mounted on, and the second ribbon cable that is connected to the signal detector may also be connected to a connector or socket mounted on the PCB. The signal detector may be located at a probe face of the probe tip. The signal emitter may be optically located behind the probe face of the probe tip.

In an implementation, connector 336 includes a locking feature, such as an insert connector that inserts into a connecting port and then twists or screws to lock. If so, the connector is more securely held to the system unit and it will need to be unlocked before it can be removed. This will help prevent accidental removal of the probe.

In an implementation, connector 336 includes one or more PCBs that are connected to one or more wires (e.g., ribbon cables) that connect to the signal emitter, the signal detector, or both. For example, a first ribbon cable may connect to a first PCB that connects to the signal emitter. A second ribbon cable may connect to a second PCB that connects to the signal detector. connect a firs Block 351 shows a power block of the system unit having both AC and battery power options. In an implementation, the system includes an AC-to-DC converter 353, such as a full-wave rectifier. The converter takes AC power from a wall socket, converts AC power to DC power, and the DC output is connected (indicated by an arrow 354) to the components of the system unit needing power.

In an implementation, the system is battery operated. The DC output of a battery 356 is connected (indicated by an arrow 357) to the components of the system unit needing power. The battery may be recharged via a recharger circuit 359, which received DC power from the AC-to-DC converter. The AC-to-DC converter and recharger circuit may be combined into a single circuit. In an implementation, the battery is rechargeable via magnetic charging or induction charging.

In an implementation, block 351 is a battery module that includes one or more batteries that power the components of the system unit. The batteries may be rechargeable or disposable batteries. The block may not include the AC-to-DC converter. Block 351 may be a block that is integrated with the system unit or is separable from the system unit.

Figure 6:
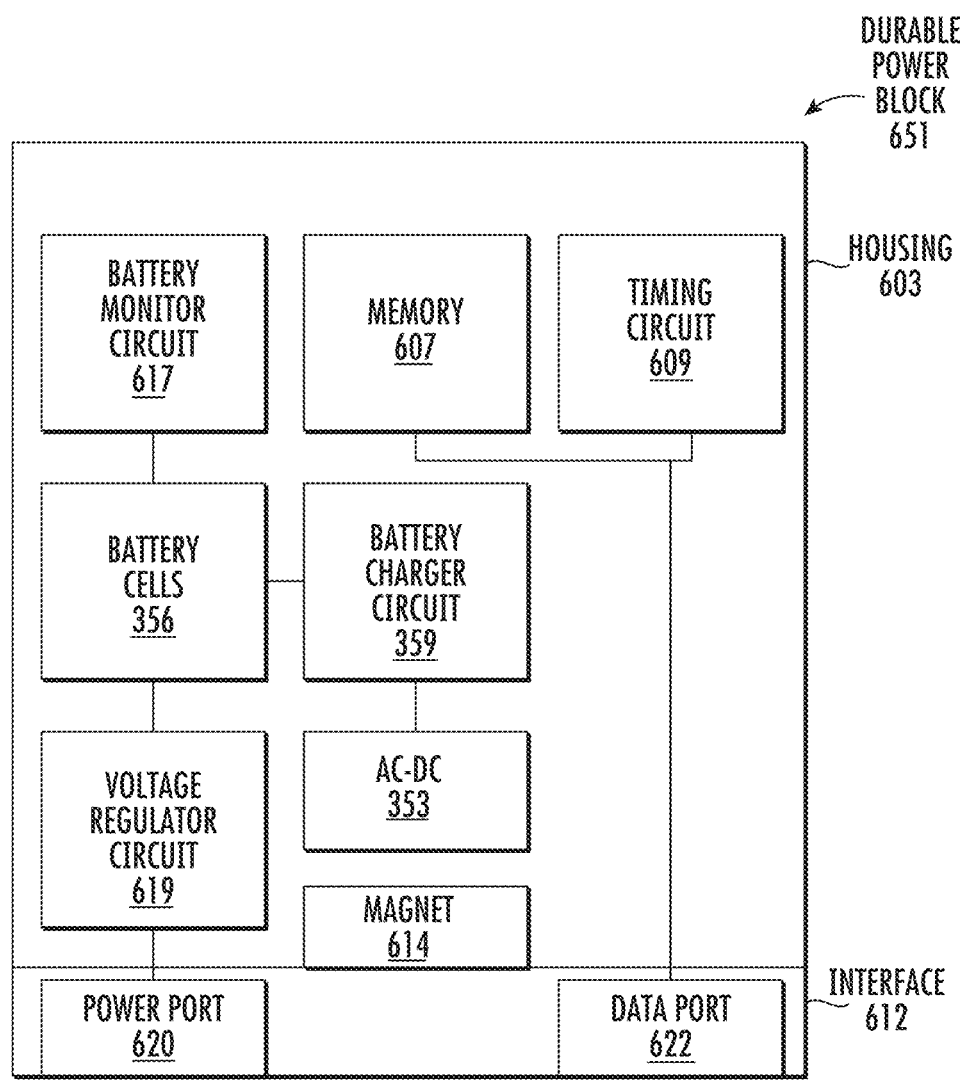
FIG. 6 shows a diagram of the power block of the system unit, in an implementation.

FIG. 6 shows block 651 that is a power block, in an implementation. Block 651 is similar to block 351 but may include a battery monitor 617, a voltage regulator circuit 619, a memory 607, a timing circuit 609, an interface 612, which includes a power port 620 and a data port 622, a magnet 614, other circuits, or any combination of these circuits.

Battery monitor 617 may be connected to the battery cells 356 and may monitor the capability of the battery cells. For example, the battery monitor may determine a current charge state, such as a percentage of the total possible charge. The battery monitor may determine the charge capacity of the battery cells. The charge capacity may be a percentage of the charge capacity compared to the charge capacity of the battery cells when new. The battery monitor may determine the maximum power delivery capability of the battery.

The battery cells may be disposable battery cells, such as alkaline battery cells, or rechargeable battery cells, such as nickel metal hydride, lithium battery cells (e.g., Li/FeS2 size AA, AAA, N, CR123, 18650, or others), lithium polymer, or other types of cells. The power back may include four battery cells that are AA size cells that output 1.5 volts. The four batteries may be in series to output 6 volts, or may be in series and parallel to output 3 volts.

Voltage regulator circuit 619 may be connected between the battery cells and the power port of the battery interface 612. The voltage regulator circuit conditions the voltage output from the battery to output an approximately constant voltage. The voltage regular circuit may also include a DC-to-DC converter that converts a first voltage output from the battery cells to a second voltage that is different from the first voltage.

The timing circuit is a circuit that determines the amount of time length that the battery has been used. Information for the amount of time may be stored in the memory and may be transferred through the data port to the processor when the processor queries the memory for the information.

In an embodiment, the memory may also store an encrypted identifier that identifies the power block. The processor may be adapted to retrieve the encrypted identifier via the power blocks data port. The processor or another decryption circuit of the system unit may decrypt the encrypted identifier and may identify the power block based on the identifier after decryption. The identifier may identify the manufacturer of the power block or may identify other information about the power block, such as the manufacturing date, the battery cell type, battery cell voltage, elapsed usage time, or any combination of these elements. In an implementation, if the identifier is not a known identifier that is known to the system unit, then the processor with not allow the system unit to operate with the power block. That is, the system unit will not operate with a power block manufactured by an unknown manufacturer. Allowing the system unit to operate with known (e.g., authorized) power blocks, the system unit is assured that the power provided by the power block is within the operating specifications of the system unit. Therefore, the circuits, signal emitters, signal detectors, and other elements of the system unit will operate within predetermined parameters and will not operate outside of the predetermined parameters. Also, using a known battery from a known manufacturer provides that the stem unit will operate for a known period of time so that the system unit will not run out of battery power during a medical procedure, such as a surgery. Operating the system unit according to predetermined parameters, facilitates the system unit making accurate and reliable oximetry measurements.

In an implementation, nonvolatile memory 315 stores one or more identifiers for one or more power blocks that may operate with the system unit. The processor may compare the identifier for the power pack that has been decrypted to the one or more identifiers retrieved from the nonvolatile memory to determine whether the power block will be allowed to operate with the system unit. If the power block is not authorized for use with the system unit, the processor may cause a message to be displayed on the display that indicates that the power block is not authorized for use with the system unit. If the power block is authorized to operate with the system unit, then the system unit may operate to make oximetry measurements with or without displaying information on the display about the authenticity or the inauthenticity of the power block.

In an implementation, the memory of the power block stores an indicator that indicates whether the battery has been previously used. The indicator may be the time information for the amount of time that the power block has operated. The indicator may be the time information for the amount of time that the power block has operated. In an embodiment, a time stored in memory that is greater than zero is an indicator that the power block has been previously used. In an embodiment, a nonzero use time stored in the memory is an indicator that the power block has been previously used. Alternatively, the indicator may be an identifier of a system unit that the power block has been connected to and provided power to. For example, the nonvolatile memory of the system unit may store an identifier of a system unit. The processor of the system unit may transfer the system identifier of the system unit to the power block for storage in the power block's memory.

When the power block is attached to a system unit, the processor of the system unit may query the power block's memory to retrieve any system identifier that may be stored in the power block's memory. In an implementation, if a system identifier retrieved from the power block's memory is different from the system identifier of the system unit that retrieved the system unit from the power block's memory, then the system unit will not operate with the power block. The implementation attempts to ensure that a power block is fully charged and can be used for the duration of a medical procedure (e.g., a surgery) without the power block running out of stored energy. Ensuring that a power block is unused prior to using the power block during a medical procedure provides that the power block will not run out of power during the procedure and minimize risk to a patient. That is, patient risk is lowered if a system unit used during a procedure does not run out of power and can be used for patient monitoring when required.

In an implementation, when the power block is attached to a system unit, the processor of the system unit may query the power block's memory to retrieve the time information for the amount of time that the power block has operated. In an implementation, if the system unit determines that the power block has been previously used based on the time information, then the system unit will not operate with the power block. Similar to the embodiment described immediately above, ensuring that a power block is unused prior to using the power block during a medical procedure provides that the power block will not run out of power during the procedure and minimize risk to a patient.

The power block may include one more magnets 614 that are arranged in an arrangement, such as a square, a rectangular, or another arrangement. A system unit may also have one or more magnets or one or more metal plates (e.g., ferromagnetic plates) that are arranged in an arrangement that is complementary to the arrangement of magnets in the power block. The magnets of the power block may attract the magnets or metal plates of the system unit when the power block is placed in contact with the system unit. The magnetic attraction between the magnets or plates may hold the power block in place when the system unit is being used.

The power block may include one more plates (e.g., ferromagnetic plates) that are arranged in an arrangement, such as square, rectangular, or another arrangement. The system unit may include one or more magnets that are arranged in a complementary arrangement. The magnets of the system unit may magnetically attract the metal plates of the power block when the power block is placed in contact with the system unit. The magnetic attraction between the magnets and plates may hold the power block in place when the system unit is being used.

In an implementation, the power port of the power block includes at least two electrical contacts (e.g., a power contact and a ground contact) and the data port includes at least two electrical contacts (e.g., a data line and a shared ground contact with the power port). The electrical contacts are arranged in an arrangement, such as in a row, in a square, in a rectangle, another arrangement. The system unit includes a power port that includes at least two electrical contacts (e.g., a power contact and a ground contact) and includes a data port that includes at least two electrical contacts (e.g., a data line and a shared ground contact with the power port). The arrangement of the electrical contacts is complementary to the electrical contacts of the power block.

When the power block is placed in contact with the system unit, the magnetic attraction between the magnets or between the magnets and metal plates forces the electrical contacts of the power port in the system unit into contact with the electrical contacts of the power port of the power block. Also, the magnetic attraction forces the electrical contacts of the data port in the system unit into contact with the electrical contacts of the data port of the power block. As such, electrical power can be transferred from the power block to the system unit to power the circuits and other elements of the system unit, and data can be transferred between the power block and the system unit.

Figure 7:
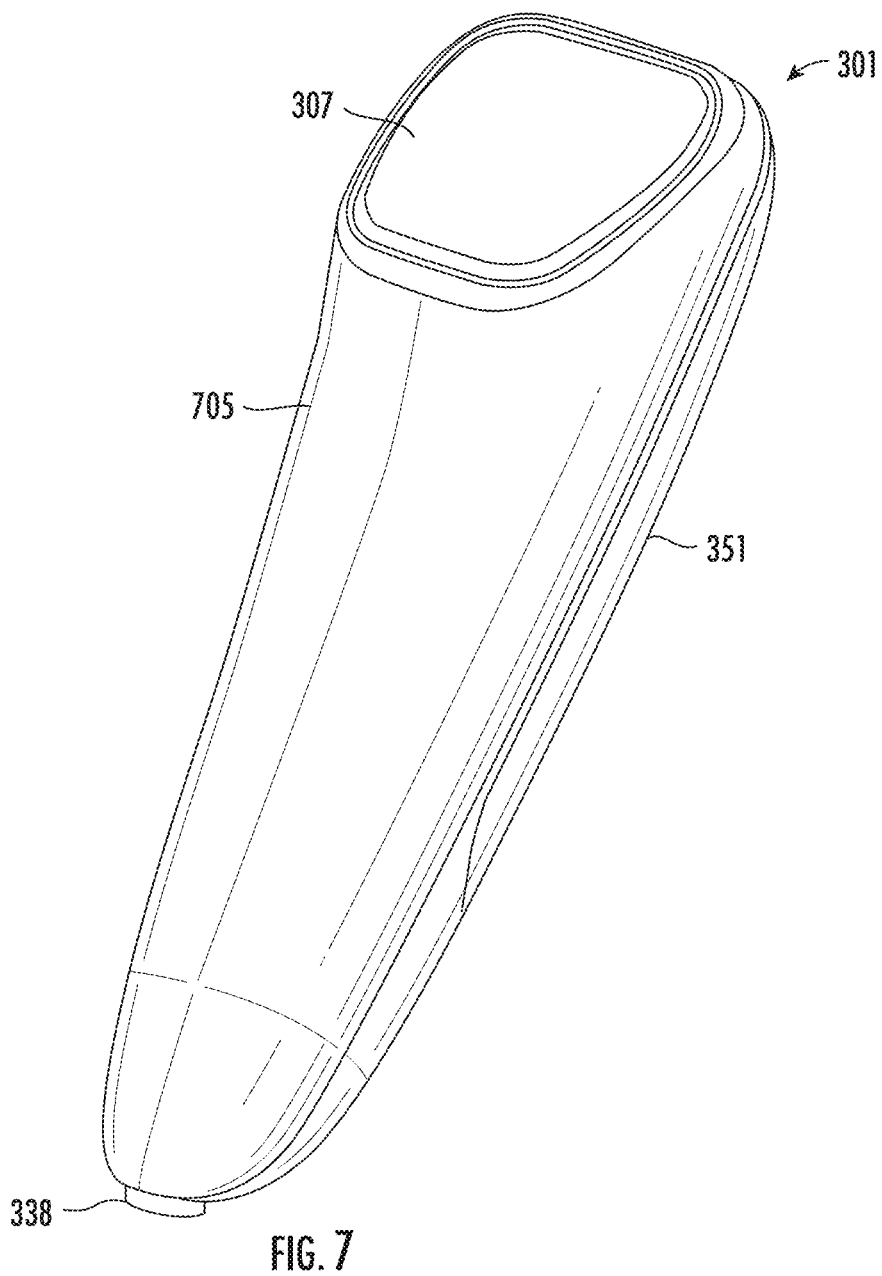
FIG. 7 shows a perspective view of the system unit and power block.

FIG. 7 shows a perspective view of the system unit 301 and power block 351 coupled to the system unit, in an implementation. The display 307 of the system unit is located at a first end of the system unit and the probe tip 338 is located at a second end of the system unit where the first and second ends of proximal and distal ends of the unit. The housing of the system unit tapers from the first end to the second end. The described circuit elements are housed in the housing 705 of the system unit. housing 705 of the system unit. When the second window of the sheath is in contact with tissue, the first window of the sheath and the display of the system unit faces away from the tissue for easy visibility of the display. In an implementation where the system unit is used without a sheath, when the probe face of the system unit is in contact with tissue, the display faces away from the tissue for easy visibility of the display.

Figure 8:
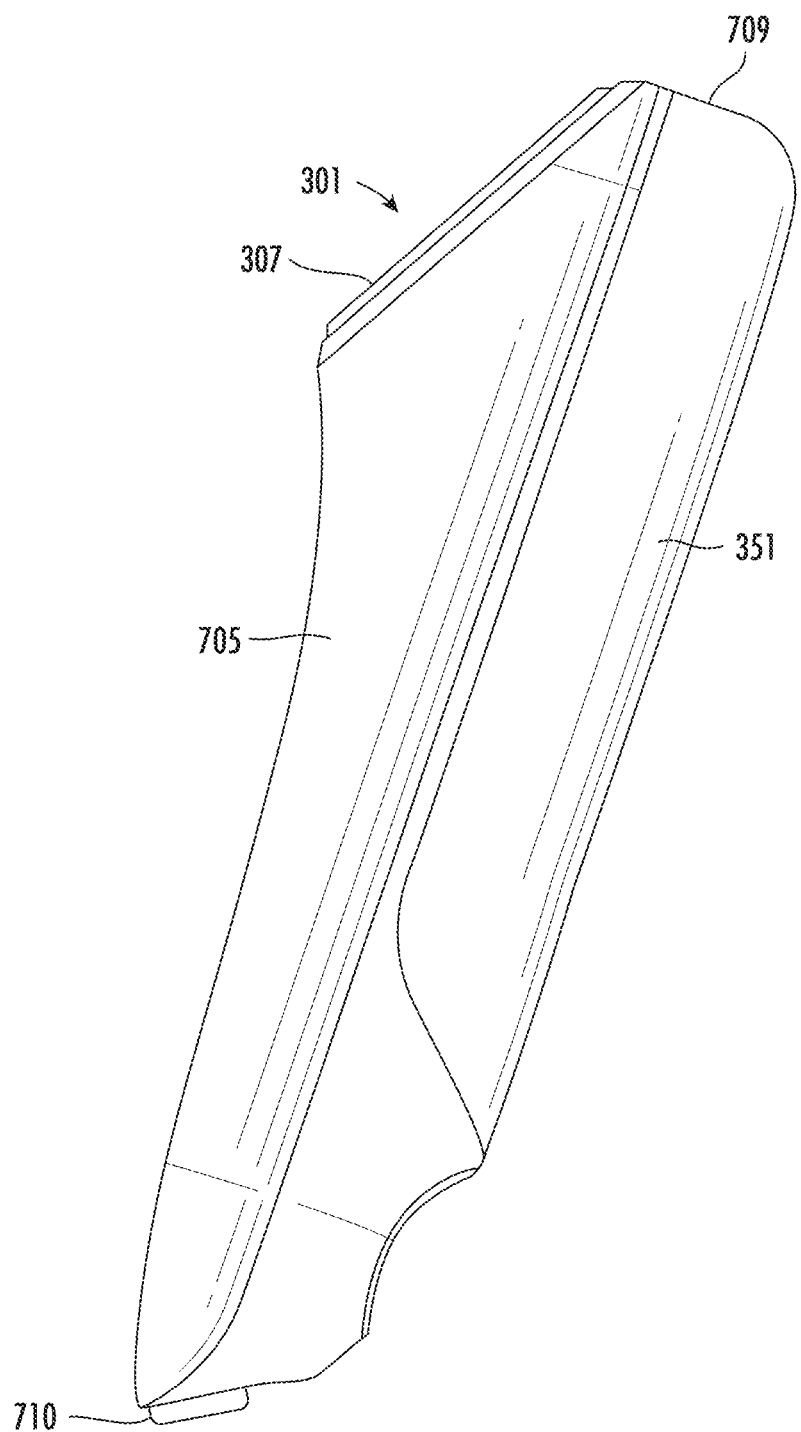
FIG. 8 shows a side view of the system unit.

FIG. 8 shows a side view system unit 301, in an implementation. The housing 705 of the system unit includes a bezel 710 that houses a portion of the probe tip. The bezel includes an opening the exposes a probe face of the probe tip. The bezel is at a distal end of the system unit and a top surface 709 is at a proximal end of the system unit.

Figure 9:
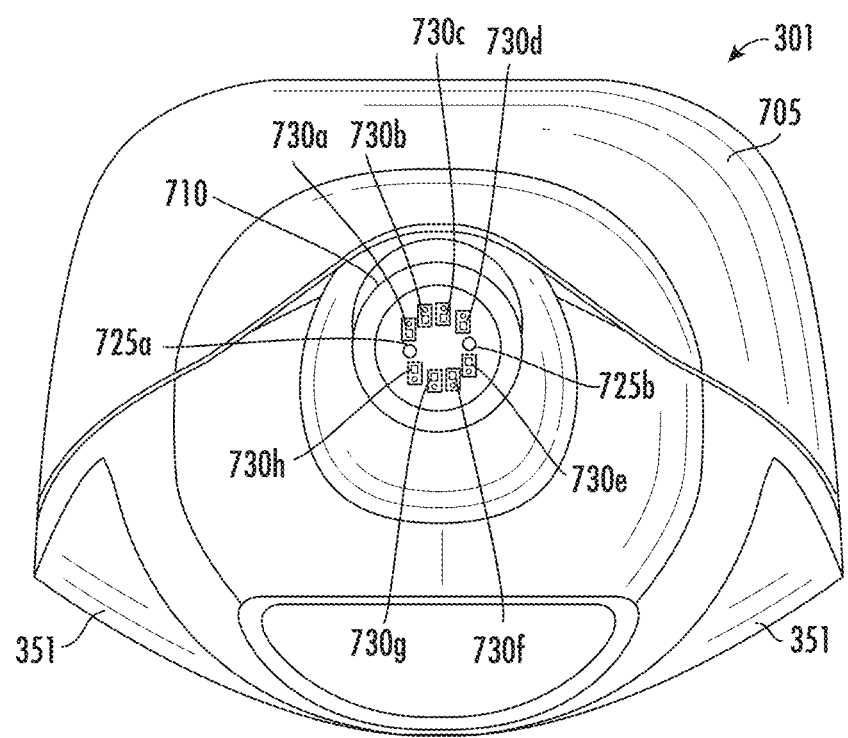
FIG. 9 shows an end view of the system unit.

FIG. 9 shows an end view of the second end of the system unit, in an implementation. The end of bezel 710 is shown with the probe face 715 in the opening of the bezel. The probe face may include an aperture plate 720 that includes a number of source apertures, for example, source apertures 725*a* and 725*b*, and includes a number of detector apertures 730*a*-730*h*. Each of the source apertures may be included in a source structure that may include light sources, such as one or more optical fibers (e.g., forming a portion of the probe tip of the system unit), laser diodes, LEDs, one or more portions of the aperture plate, or other structures at the probe tip in any combination. Each of the detector apertures may be included in a detector structure that may include light detectors, such as one or more optical fibers, photodetectors, one or more portions of the aperture plate, or other structures at the probe tip in any combination.

Figure 10A:
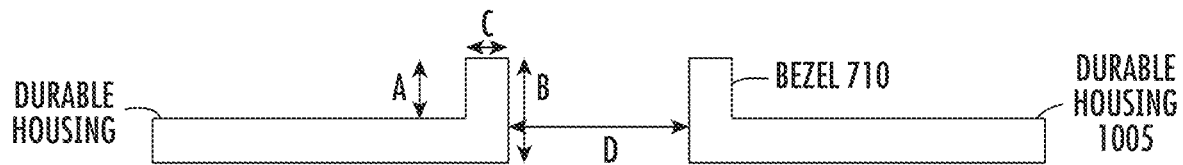
FIGS. 10A-10D show a number of steps for forming the probe face of the probe tip and forming the finished bezel of the housing of the system unit.

FIGS. 10A-10D show a number of steps for forming the probe face 715 of the probe tip 338 and forming the finished bezel 710 of the housing 1005 of the system unit 301. FIG. 10*a* shows the bezel 710 of the housing 1005 at an initial height A where the height is from the outside surface of the housing to the top of the bezel. Height A may be from about 3.5 millimeters to about 4 millimeters. In a specific implementation, height A is about 3.75 millimeters. The inner height B of the bezel is from the inside surface of the housing to the top of the bezel. Height B may be from about 4.5 millimeters to about 5.5 millimeters. In a specific implementation, height B is about 5.05 millimeters. The diameter D of the opening of the bezel may be from about 8 millimeters to about 10 millimeters. In a specific implementation, the diameter of the opening of the bezel may be about 9.1 millimeters. The width C of the bezel at the bezel's end may be about 1.0 millimeters to about 2.0 millimeters. The width C may vary around the circumference of the bezel. In a specific implementation, the width C of the bezel is about 1.5 millimeters.

Figure 10B:
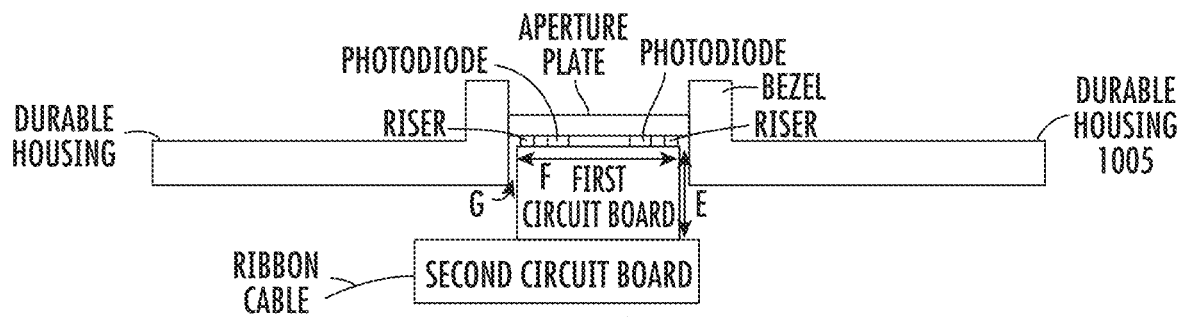

FIG. 10B shows the housing and bezel with a portion of the probe tip 338 in the housing and bezel. The portion of the probe tip shown includes a first circuit board 1020, a second circuit board 1025, riser 1030, photodiodes 1035, an aperture plate 1040, and a ribbon cable 1045 connected to the second circuit board. The first and second circuit boards may include electrical traces that are coupled. The second circuit board may be a fiberglass circuit board (e.g., FR4) that includes electrical traces that are connected to electrical traces of the first circuit board. The electrical traces of the first circuit board may extend upward from the second circuit board along the outer surface of the first circuit board. The first and second circuit boards may be connected by mechanical fasters, plastic welding, an adhesive (e.g., epoxy), another material, or any combination of these materials. The first circuit board may have a diameter F of about 6 millimeters to about 8 millimeters. In a specific implementation, the diameter F of the first circuit board is about 7 millimeters. The first circuit board may have a height E of about 3 millimeters to about 4 millimeters. In a specific implementation, the height E of the first circuit board is about 3.5 millimeters.

A distance G between the side of the first circuit board and the inner sidewall of the bezel may be about 0.5 millimeters to about 1.5 millimeters. In a specific embodiment, the distance between the side of the first circuit board and the inner sidewall of the bezel may be about 1.05 millimeters.

The riser may be connected to both the first circuit board and the aperture plate and may separate the first circuit board and aperture plate may be predetermined height. The photodiodes may be mounted on a top surface of the first circuit board and be connected to the electrical traces of the first circuit board. The aperture plate may include an aperture for each photodiode that is mounted on the first surface of the first circuit board and the diodes may respectively be inside the apertures. The height of each riser may be about 100 micrometers to about 200 micrometers. In an implementation, the height of each riser is about 150 micrometers.

Figure 10C:
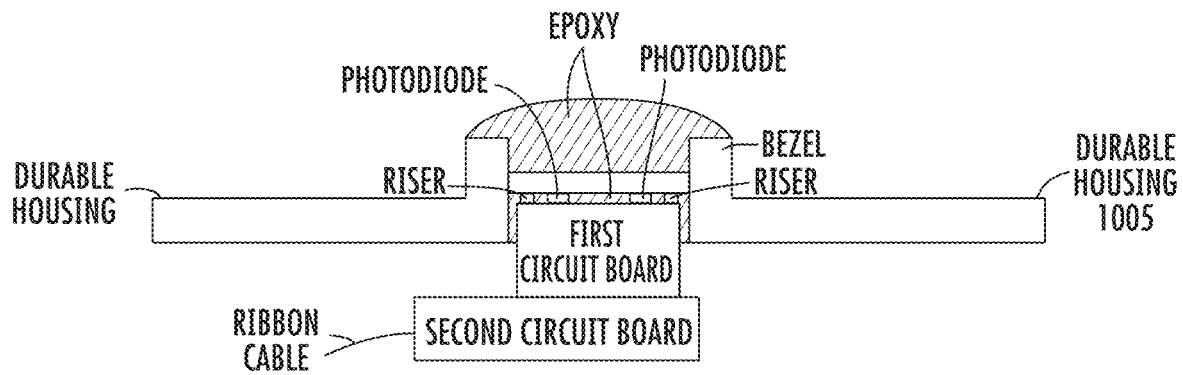

After the portion of the probe tip shown in FIG. 10B is placed into the opening of the bezel, epoxy is flowed into the opening as shown in FIG. 10C. The epoxy may flow into the apertures of the aperture plate, along the sides of the first circuit board, and may flow to the second circuit board and around the sides of the second circuit board.

Figure 10D:
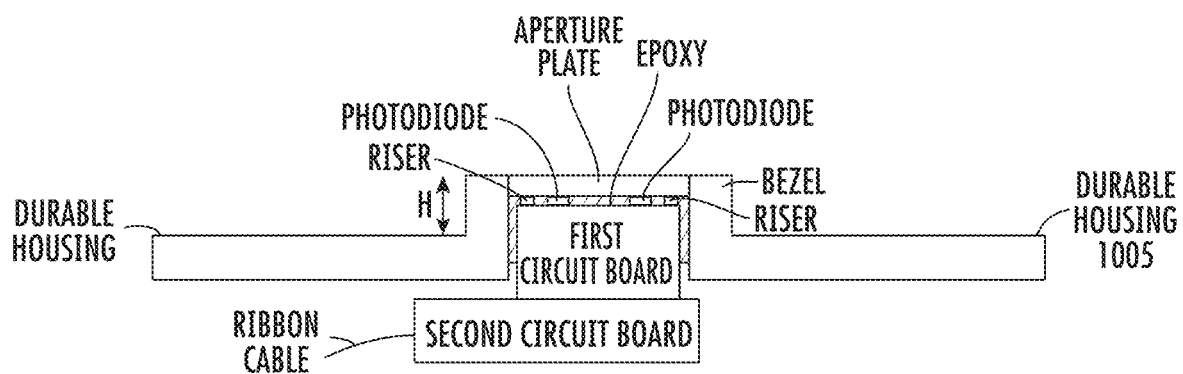

After the epoxy cures, the epoxy and sides of the bezel may be removed (e.g., polished down) to a final height, as shown in FIG. 10D. The final outside height H of the bezel may be about 2.0 millimeters to about 3 millimeters. In a specific implementation, the final outside height H of the bezel is about 2.58 millimeters. In an implementation, a portion of the aperture plate may also be thinned (e.g., polished thinner) when the bezel and epoxy are removed. The aperture plate can include a marker embedded in the plate. The embedded marker is exposed and polished away in the polishing process, the polishing is completed when the marker is polished away.

In an implementation, the epoxy is polished down to the surface of the tops of the photodetectors inside the apertures of the aperture plate. In another implementation, a thin layer of epoxy remains over the tops of the photodetectors after polishing. In another implementation, a thin layer of the tops of the photodetectors is removed from polishing. In an implementation, a layer of epoxy is over the bezel sidewall and the front surface of the aperture plate. The layer of epoxy may be from about 5 micrometers to about 50 micrometers. In an implementation where the top surface of the aperture plate is in the sidewall of the durable housing after polishing, a layer of epoxy is in the opening in the sidewall and over the front surface of the aperture plate that faces outward from the sidewall. The layer of epoxy may be from about 5 micrometers to about 50 micrometers.

Figure 11:
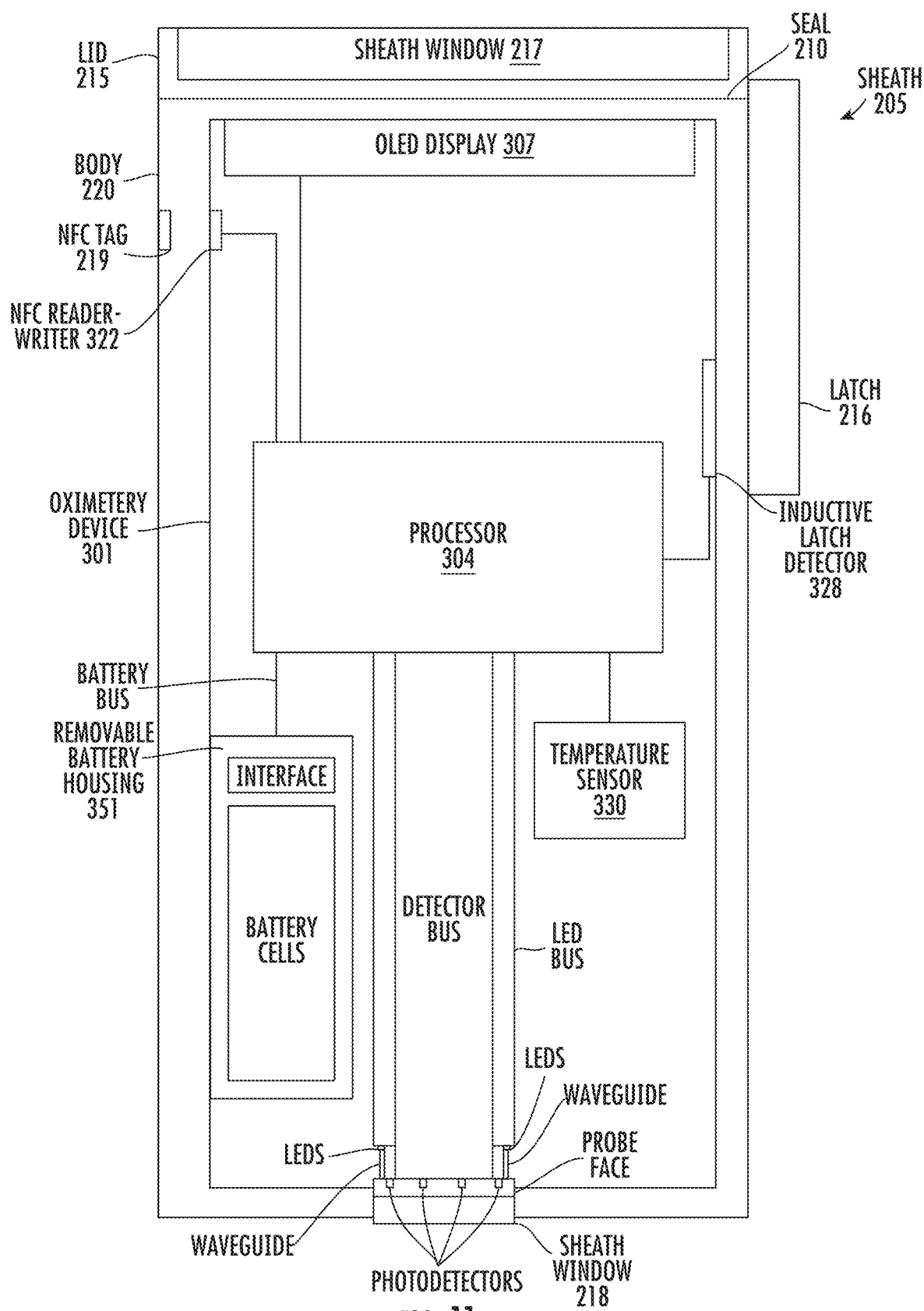
FIG. 11 is a block diagram of the system unit in a sheath, in an implementation.

FIG. 11 is an additional block diagram of system unit 301 in sheath 205, in an implementation. The sheath includes the seal 210, the lid 215, the body portion 220, a latch 216, a first sheath window 217, a second sheath window 218, and a radio-frequency communication device 219, such as an NFC tag or an NFC reader-writer. When system unit 301 is in the sheath and the probe face of the system unit contacts that the inside surface of sheath window 218, the NFC reader-writer is registered with the NFC tag of the sheath. That is, the probe face of the system unit and the inside surface of sheath window 218 are reference surfaces for the NFC circuits so that the circuits can register for NFC communication when the surfaces contact.

The sheath may include a hinge that hinge couples the lid to the body portion and allows the lid to be opened and closed. Both the lid and the body of the sheath can be formed of a relatively rigid plastic material. In an implementation, the lid is formed from a plastic material that is less rigid than the body portion of the sheath. In an implementation, the lid is formed from a flexible plastic material.

As described above, the latch latches that lid closed and seals the seal. The latch also releases the lid from the closed position and allows for the seal to be unsealed. The latch detector 328 (e.g., an inductor or a capacitive detector and an A-to-D converter coupled to the processor) of the system unit is positioned nearest to the latch when the latch is closed (i.e., the first distance from the latch detector) so that the latch detector can detect when the latch is latched, the lid is closed, and the seal is sealed. The latch detector can detect when the latch opens and moves away from the first distance.

In an implementation, a first portion of the latch is rigidly connected to the lid and a second portion of the latch extends in a cantilever configuration from the lid. The first and second portions are opposite portions of the latch. The latch is capable of bending to latch that latch to the body of the sheath and bending to unlatch the latch from the body. The latch can be steel, such as spring steel, which allows the second portion (e.g., cantilevered portion) of the latch to bend to latch and unlatch the latch from the body.

In an implementation, a first portion of the latch is rigidly connected to the body and the second portion of the latch extends in a cantilever configuration from the lid. The latch capable of bending to latch that latch to the lid of the sheath and unlatch the latch from the lid.

The latch can be hinge connected to the lid via a lid hinge. With the lid hinge connected to the lid, that latch can rotate towards the body of the sheath and away from the body of the sheath to latch that latch to the body and unlatch the latch from the body. In another implementation, the latch is hinge connected to the body of the sheath and can rotate towards the lid and away from the lid to latch to the lid and unlatch from the lid.

In an implementation, the first window 217 is located in the lid of the sheath. In another implementation, the lid is transparent and the lid is the first window of the sheath. The first window is positioned over the display 307 (e.g., an organic LED display) of the system unit when the lid of the sheath is closed. The first window can be transparent, so that information displayed on the display is visible and discernable to a user when the lid of the sheath is closed. The first window can be a plastic material or glass. The first window can be sealed to the lid via an adhesive, such as epoxy, an O-ring, welding, heat-stake (if both materials are plastic), or another seal material. The seal can prevent contaminants (e.g., patient tissue, patient fluid, or other debris) from passing through the seal and contaminating the system unit. The sheath window may be a square-shaped window or a rectangular window that approximately matches the size and shape of display 307.

In an embodiment, the first window is replaced by a display. The display is communicatively coupled (e.g., wired or wirelessly) to the system unit, which may not include a display in the implementation. The system unit can communicate information that is to be displayed on the display of the sheath, which can control the display to display the information. The display of the sheath can display any information that is displayed on the display of the system unit that is described in this patent application.

The second window 218 can be at an opposite end of the sheath from the first window. The second window can contact the probe face of the probe tip when the system unit is in the sheath. The second window can have a relatively flat surface that contacts the polished probe face so that relatively little air is trapped between the second widow and the probe face when the second window and probe face are in contact. In an implementation, the inside surface (e.g., inside the body of the sheath) of the second window can have an adhesive that can stick to the probe face of the system unit.

In an implementation, the I/O interface 322 of the system unit includes an NFC reader-writer. The NFC reader-writer can power the NFC tag 219 of the sheath so that the NFC reader-writer can communicate with the NFC tag. In some implementations, the NFC tag is battery powered by a battery of the NFC tag or of the sheath. In implementations, the NFC tag is a read only NFC tag where information can be read from the NFC tag by the NFC reader-writer of the system unit. In an implementation, the NFC tag can be read and can be written to by the NFC reader-writer. In an implementation, the NFC reader-writer is an NFC reader and is not configured to write to an NFC tag.

In an implementation, the NFC tag includes a memory (e.g., a non-volatile memory, a random access memory, or both) that can store an identifier for the sheath, store an indicator that indicates whether the sheath has been previously used or is unused, other information, or any combination of this information. The identifier for the sheath can be an unencrypted identifier or an encrypted identifier that is previously stored in the memory. An identifier can be unique to a sheath or an identifier can be used for a number of sheaths. The identifier can identify the sheath as a particular type of sheath, such as a sheath that is reusable or a sheath that is not reusable. The identifier can be stored in the memory of the NFC tag by a manufacturer of the NFC tag or a manufacturer of the sheath.

Figure 12:
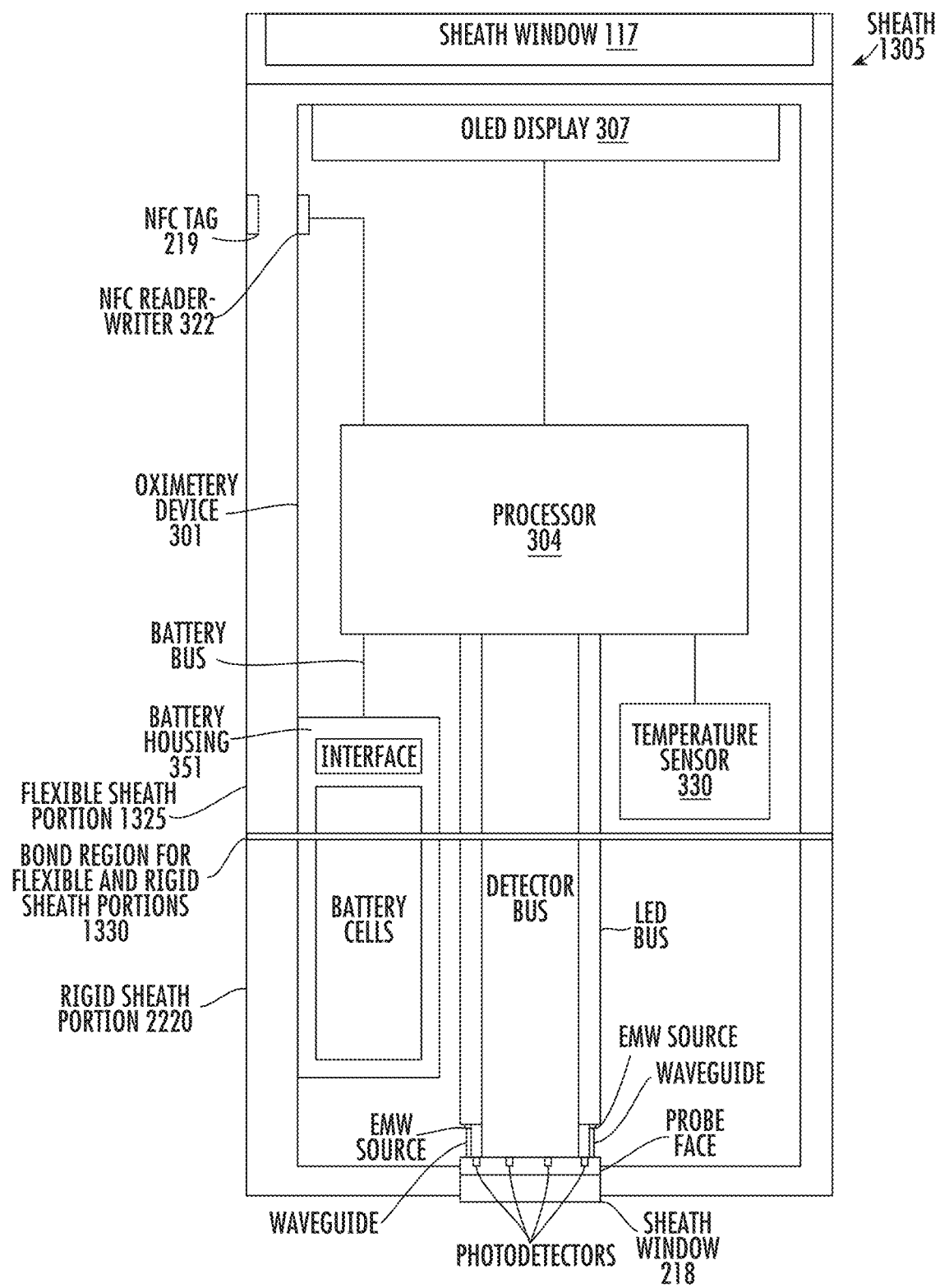
FIG. 12 is a block diagram of the system unit in the sheath, in an implementation.

FIG. 12 is a block diagram of system unit 301 in sheath 1305, in an implementation. Sheath 1205 is similar to sheath 205 but differs in that a lower body portion 1320 of the sheath is a relatively rigid plastic material and an upper body portion 1325 of the sheath is a relatively flexible plastic material. That is, the material of the upper body portion has a higher flexibility than the lower body portion. The upper and lower body portions may be coupled by an adhesive 1330, sonic welding, or another bonding material that forms a seal between the body portions. The seal is a barrier to patient tissue, patient liquid, and other contaminants. A top portion of the upper body portion can be sealed so that a system unit can be sealed in the sheath where patient tissue, patient liquid, and other contaminants cannot reach the system unit when the unit is sealed in the sheath.

Figure 13:
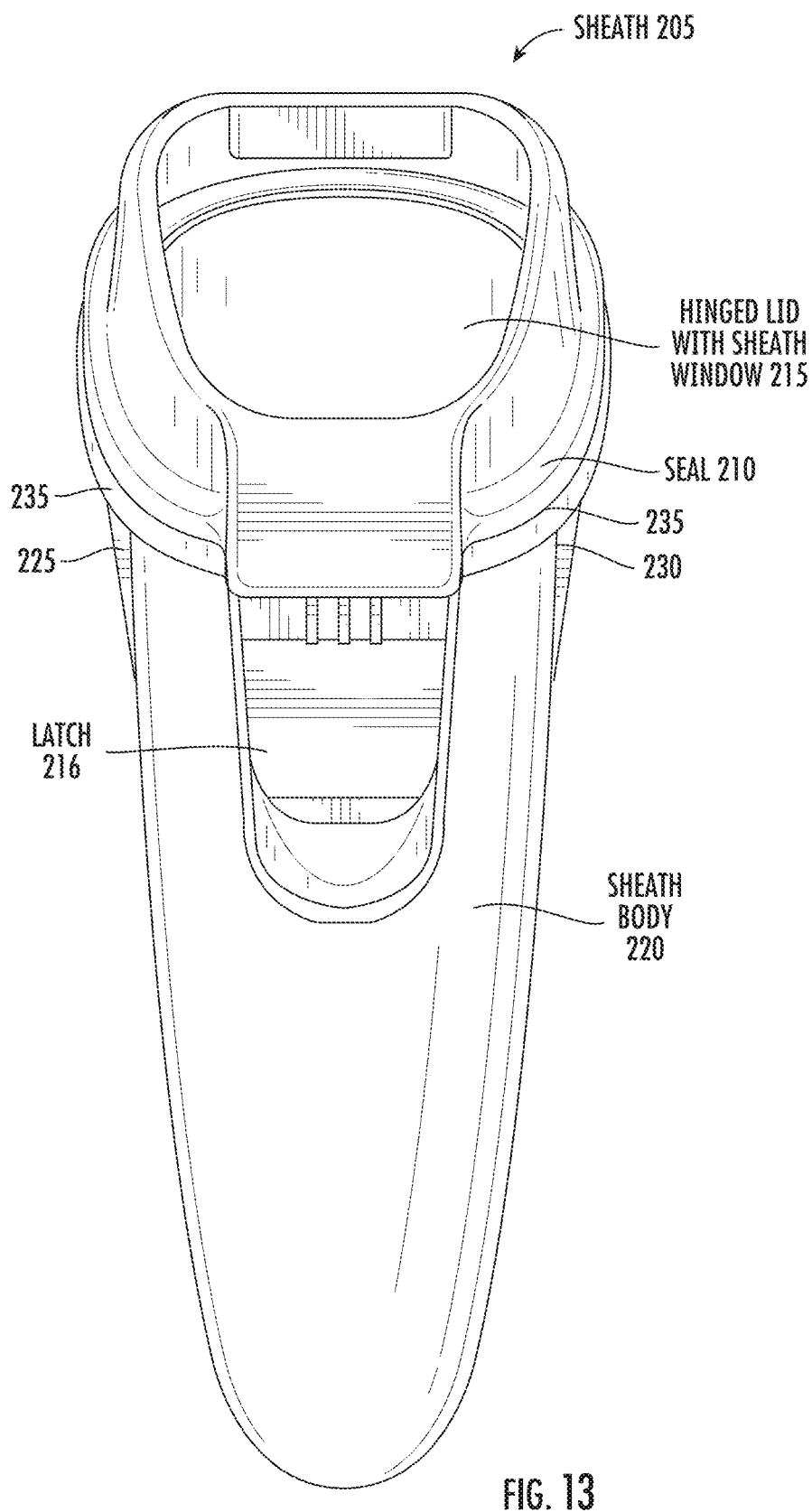
FIG. 13 shows a front view of the sheath, in an implementation.

FIG. 13 shows a front view of the sheath 205, in an implementation. The sheath is shown in FIG. 13 with the lid 215 closed against the body 220 of the sheath with the latch in a latched position against the body. The lid may be formed of a first plastic material that can be transparent (e.g., the window of the lid), translucent (e.g., portions of the lid attached to the window), opaque, or any combination of these properties. The body may be formed of a second plastic that can transparent, translucent, opaque, or any combination of these properties. The second window of the body may be attached to the body via an adhesive (e.g., epoxy), plastic weld, ultrasonic welding, or other fasteners. In an embodiment, the second window is ultrasonic welded to the sheath body and a portion of material from the welding process is over the edge of the second window on the outside surface of the body, on inside surface of the body, or both to inhibit the second window from becoming detached from the body. The second widow may form a seal with the body where the second window attaches to the body where contaminants cannot pass through the seal to contaminate a system unit in the sheath via the seal; and so that contaminants present on the system unit cannot reach the patient.

In an implementation, the lid of the sheath is a plastic material. The material can be polycarbonate (e.g., polycarbonate healthcare resin, such as Lexan HP1-112 of General Electric Company of Boston Mass.), acrylic, polyethylene terephthalate (PET), PETG, polyester, acrylonitrile butadiene styrene (ABS), or other plastic material. Polycarbonate, for example, is a material the lid may be made of because the material is easy to form, can be transparent, and can be sterilized by a variety of sterilization techniques and material, such as ethylene oxide (EtO), exposed to irradiation (both gamma and electron-beam), and steam autoclaving, isopropyl alcohol exposure, and other techniques and materials.

In an implementation, the body of the sheath is a plastic material. The material can be polycarbonate, acrylic, polyethylene terephthalate (PET), PETG, polyester, acrylonitrile butadiene styrene (e.g., ABS medical resin, such as Lustran 348 of INEOS Styrolution Group GmbH of Darmstadt, Germany), or other plastic material. ABS, for example, is a material the body may be made of because the material is easy to form and can be sterilized by a variety of sterilization techniques and material, such as ethylene oxide (EtO), exposed to irradiation (both gamma and electron-beam), and steam autoclaving, isopropyl alcohol exposure, and other techniques and materials. In an implementation, the body of the sheath is metal. In an implementation, the body of the sheath is ceramic.

The second window of the sheath at the bottom of the sheath is a plastic material or a glass material. In an implementation, the second window is a plastic material. The material can be polycarbonate, acrylic, polyethylene terephthalate (PET), PETG, clear polyester, clear acrylonitrile butadiene styrene (ABS), or other transparent plastic material. PET, for example, is a material the second window may be made of because the material has a refractive index that can match or approximately match the index of refraction of other optical components of the system unit, is easy to form, can be relatively strong while relatively thin, can be made optically flat, can be transparent, and can be sterilized by a variety of sterilization techniques and material, such as ethylene oxide (EtO), exposed to irradiation (both gamma and electron-beam), and steam autoclaving, isopropyl alcohol exposure, and other techniques and materials. The glass can be silica, borosilicate glass, optical glass, or other types of glass, such as other types of hard glass.

Sheath 205 includes a first structural support 225 (e.g., a strut) and a second structure support 230 (as strut). The first structural support includes a first side that is connected to the body 220 of the sheath and a second side that is connected to a lip 235 (i.e., flange) of the sheath. The lip extends around the top of the body and forms a top edge of the body. A third side of the first structural support may not be connected to the body. The first structural support may have a triangular shape or another shape, such as square, rectangular, may have curved sides, other shapes, or any combination of these shapes. The second structural support includes a first side that is connected to the body 220 of the sheath and a second side that is connected to a lip 235 of the sheath. A third side of the second structural support may not be connected to the body. The second structural support may have the same or similar shape as the first structural support.

In an implementation, the first and second structural supports are each triangular shaped with a longer side of the triangle connected to the body and a second side of the triangle connected to the lip of the sheath. A third side of the triangular shape of each structural support may not be connected to the body. The triangle shape of each structural support may be a right triangle shape, an obtuse triangle shape, or an acute triangle shape.

In an embodiment, one or more sides of each of the struts are curved and conform to the shape of the side of the body and the shape of the side of the lip. The struts may have generally triangular shapes even with one or more curved sides.

The first side of each structure support may be about 1 millimeter long to about 50 millimeters long. The second side of each structure support may be about 0.5 millimeters long to about 10 millimeters long. The third side of each structure support may be about 1 millimeter long to about 55 millimeters long.

The first and second structural supports may be struts that provide structural rigidity to the body of the sheath that prevents the sheath from flexing, such as along the plane that the two struts may be in. For example, the struts may prevent the body of the sheath from deforming when a user holds the sheath in a hand for use. As the user's hand squeezes the sheath to hold the sheath, the struts counter the force applied by the user's hand and put counter forces on the body and lip to prevent distortion of the sheath's shape. Preventing the body of the sheath from deforming relative to the lid inhibits the seal 210 from opening during use so that contaminants will not enter the sheath and thus will not contaminate the system unit. Preventing the interior space of the sheath, the system unit, or both may allow for the sheath, system unit, or both to be reused.

Figure 14:
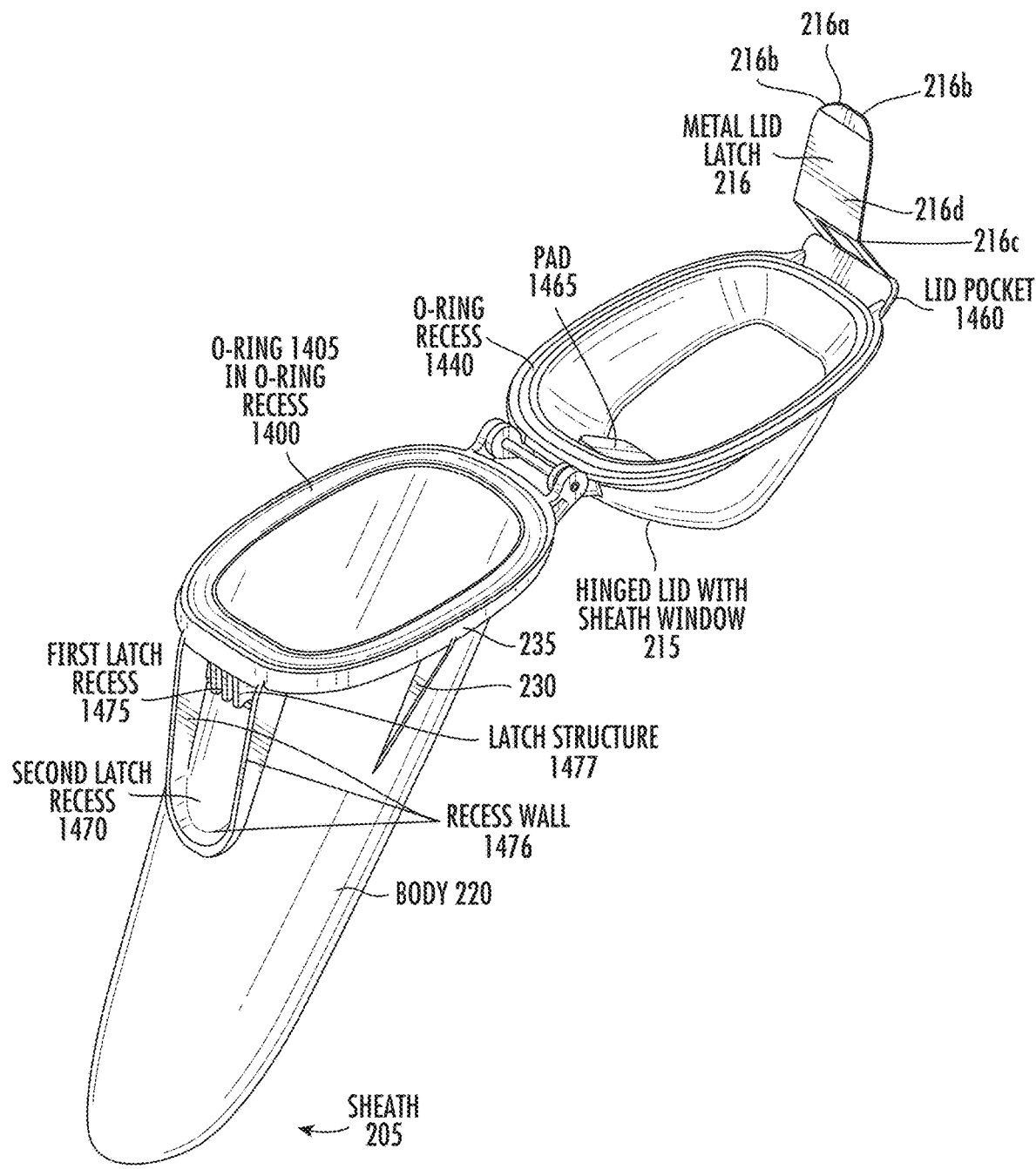
FIG. 14 shows a perspective view of the sheath, in an implementation.

FIG. 14 shows a perspective view of the sheath 205, in an implementation. The lid 215 is shown in an open position with respect to the body 220 where a system unit can be inserted into the sheath or removed from the sheath. The hinge that connects the lid and the body can be on a backside of the sheath. The body can include an O-ring recess 1400 of the top of the body. An O-ring 1405 is shown in the recess. The lid can also include an O-ring recess 4110 on the bottom of the lid. The O-ring recesses of the body and lid can contact the O-ring when the lid is closed against the body. The O-ring has a diameter from 1 millimeter to about 10 millimeters. In an implementation, the O-ring has a diameter of 5 millimeters. The O-ring can form a seal that seals the lid to the body so that contaminants cannot cross the seal between the lid and body. The body can include a first latch recess 1475 upon which the latch can sit, holding the lid closed against the body.

The O-Ring is a deformable plastic-type material. In an implementation, the O-ring is a medical-grade silicon rubber. The Shore durometer of the O-ring may be from about 8 A to about 22 A. In an implementation, the Shore durometer of the O-ring is 15±5 A. Shore durometer values are based on a unitless scale that ranges from 0 to 100. The Shore "A" durometers traditionally designates are typically used for softer materials and range broadly enough to cover flexible rubbers up to semi-rigid plastics with almost no flexibility. In contrast, Shore "D" durometers are typically used for harder materials, such as hard rubber, semi-rigid plastics and hard plastics. The deformable nature of the material that the O-ring is formed from facilitates the ridges 1420 and 1425 being able to form trenches in the O-ring when the O-ring is compressed allowing for a biological seal of the system unit in the sheath. In an implementation, a hermetic seal is formed. The O-ring may be translucent or clear silicone rubber so that the color of the O-ring is not distracting during use.

The latch can have a rounded end 216a and rounded corners 216b at the end of the latch. The end 216a, corners 216c, and edges 216d of the latch can be relatively smooth. The smooth surface will not snag and tear surgical gloves when the sheath and system unit are used. The body can include a second latch recess 1470 that resides beneath adjacent ribs in the body. These ribs can shield the latch from contact with surgical gloves, further preventing tears. Because the end, corners, and edges of the latch can be relatively smooth and not snag on gloves, clothing, or other items, this smooth feature also inhibits the latch from being inadvertently opened during use.

In an embodiment, the latch includes a magnet that can magnetically latch the lid to the body of the sheath. The sheath can include a piece of metal or another magnet that magnetically couples to the magnet of the latch. The magnets can be registered when the lid is in a closed position on the body of the sheath. One or both of the magnets can be relatively strong magnets, such as neodymium magnets.

An inner surface of the lid includes a pad 1465. The pad may be foam or other soft compressible material. When the lid is closed with a system unit in the sheath, the pad pushes on a top surface of the system unit that is at the proximal end of the unit. The top surface is connected to the back and side surfaces of the system unit and is adjacent to the display of the unit. When the lid is closed and the latch is latches, the force applied by the pad to the top of the oximeter device is from about 60 Newtons to about 85 Newtons. In an implementation, the force applied by the pad to the top of the oximeter device is about 73 Newtons.

In an implementation, the body includes a first latch recess 1475 and a second latch recess 1470. The body includes a recess wall 1476 that partially surrounds both the first and second latch recesses. An inner surface of the recess wall that faces the first and second pockets is tapered outward. The outward taper facilitates guiding the latch into the pocket at the lid is closed. The guidance of the latch into the pocket further facilitates the opening of the lid registering with the opening of the body of the sheath so that the lid and body create a seal as described in this application, and facilitates the uniform compression of the O-ring.

A portion of lip 235 that is adjacent to the first and second recesses may be a wall of the first and second recess latches. Wall 1476 may have a tapered shape with a first height at the tip tapering to a second height at a distal end of the wall that is distal from a portion of the lip where the recess wall attaches. The first height of the wall may be about 1 millimeter to about 15 millimeters. The second height of the wall may be about 0.5 millimeters to about 10 millimeters. The taper of the wall forms the second latch recess that has the same or a similar taper shape as the recess wall. The second recess can be deeper adjacent to the lip than at the distal end of the recess wall.

The wall may have a rounded shape at the distal end of the wall. Wall portions between the distal end of the wall and the lip may be relatively straight. The inside surface of the wall that faces the first and second latch recesses may have a shape that is complementary to the shape of the portion of the latch that is inside the wall when the latch is latched to the body. The wall prevents or inhibits the latch from being caught on the clothing of a user, a user's fingers, or other objects that can contact with a side of the latch and open the latch.

In an implementation, the first latch recess is formed in a latch structure 1477, which extends into the second recess. Latch structure 1477 may include a number of struts (e.g., 2-6, such as 3) that connect to lip 235 and a bottom surface of the second latch recess. Each strut includes a recess that collectively forms the first latch recess. An edge 216d of the latch can be positioned in (i.e., engage) the first latch recess when the latch is closed. The first latch recess holds edge 216d in this latch recess to hold the latch closed and as such holds the lid of the sheath closed against the O-ring and body of the sheath. The latch structure 1477 and the first latch recess are inside the second latch recess. In an implementation, the latch structure 1477 does not connect with the latch wall. In another implementation, the latch structure is connected to the latch wall.

Figure 15:
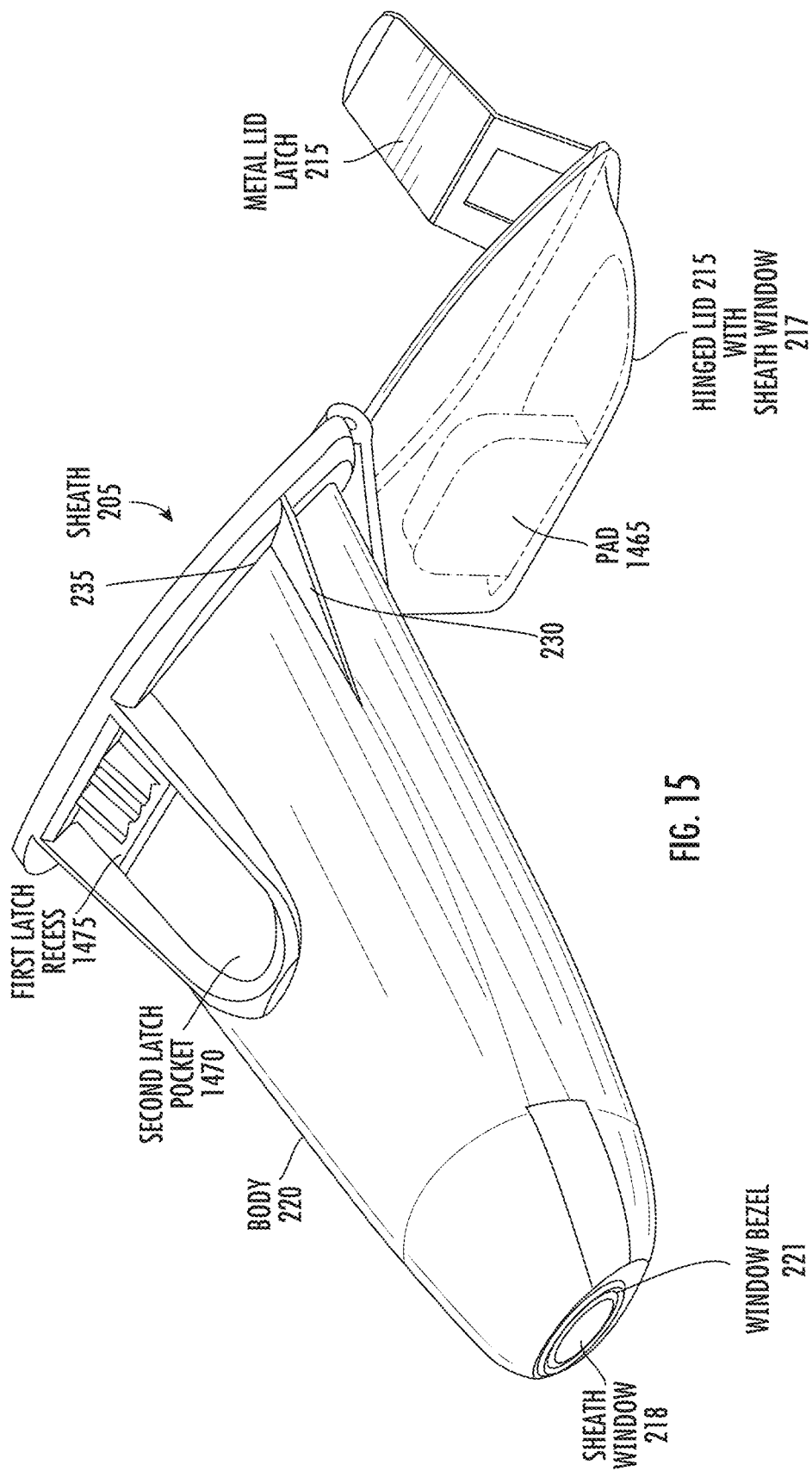
FIG. 15 shows a perspective view of the sheath, in an implementation.

FIG. 15 shows a perspective view of the sheath 205, in an implementation. The lid is shown in an open position with respect to the body where a system unit can be inserted into the sheath or removed from the sheath. The figure shows the second sheath window 218 at the bottom of the body of the sheath. A window bezel 221 is attached to the body of the sheath and covers an edge portion of sheath window 218. The window bezel may be attached to the top via an adhesive (e.g., epoxy), plastic weld (e.g., ultrasonic welding), fasteners, or any combination of these attachment techniques or materials. The window bezel includes a central opening that exposes window 218.

The second sheath window may generally be round from an end view. In a specific implementation, the second sheath window is circular. The upper and lower surface of the second sheath window may be approximately parallel. The second sheath window may be about 8 to 10 millimeters in diameter. In a specific implementation, the second sheath window has a diameter of about 9 millimeters. The second sheath window may be about 0.25 millimeters thick to about 1 millimeter thick. In a specific implementation, the second sheath window is about 0.5 millimeters thick.

In an implementation, window 218 is pressed into an opening formed in the bottom of the body of the sheath. The window may be pressed in using an arbor press or another type of press. The window may have a diameter that is larger than the opening formed in the bottom of the body of the sheath that the window sits in. The difference in the diameter of the window and opening allows for the body of the sheath to place a compression for on the window to hold the window in place in the aperture. The difference in diameters may be from about 1 micrometer to about 100 micrometers. In one implementation, a side surface of the window is rough or has a structure (e.g., cogs, gear teeth, scratches, or another structure) that aids in holding the window in the body of the sheath. The window can also be held in place in the opening by an adhesive, such as epoxy or silicone adhesive. The adhesive may be a thin film of adhesive (e.g., silicone adhesive) on the window when the window is pressed into the body of the sheath. The adhesive can contact a ledge of the aperture of the body of the sheath when the window is pressed into the aperture.

Figure 16:
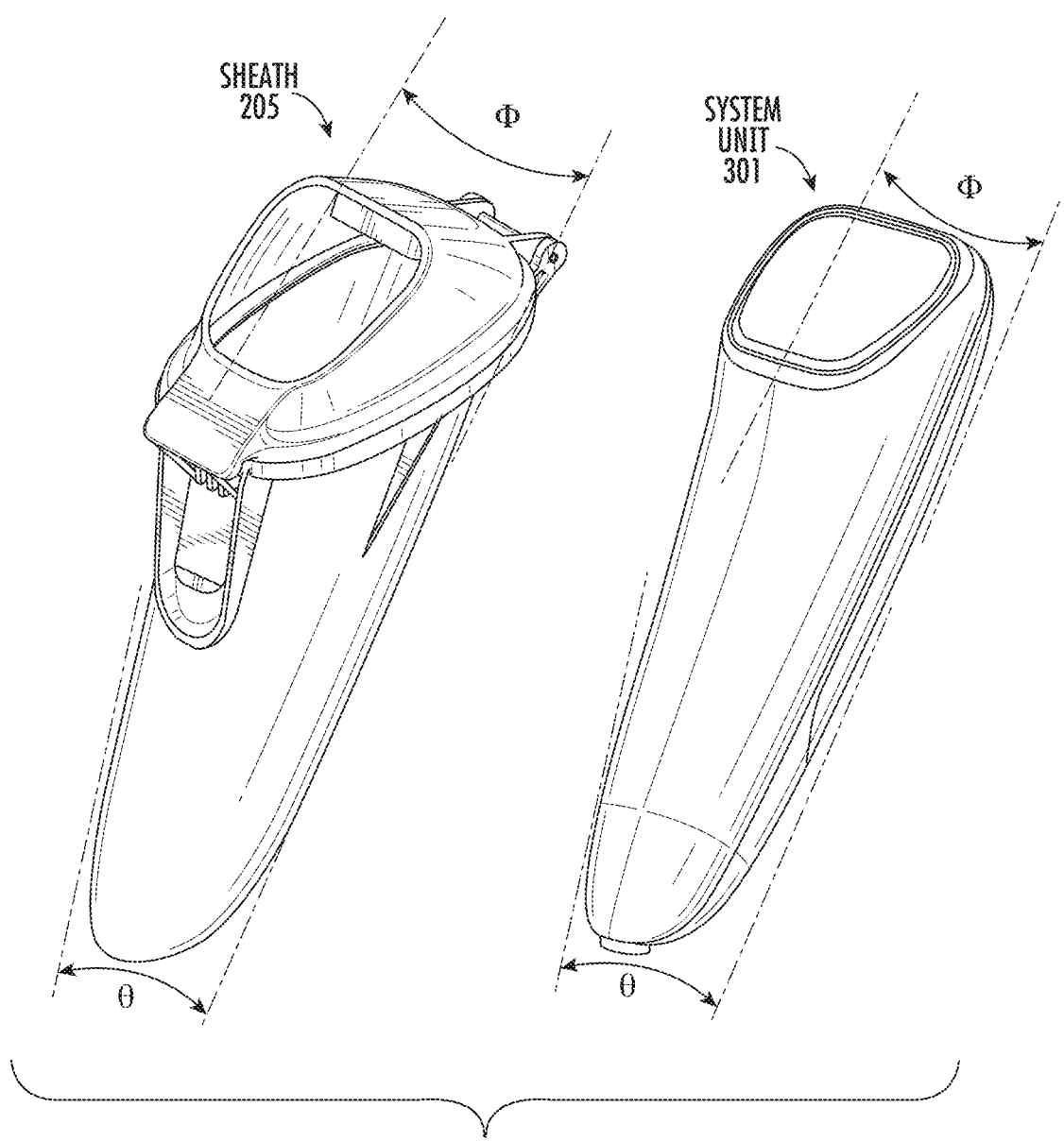
FIG. 16 shows a perspective view of the sheath and the system unit, in an implementation.

FIG. 16 shows a perspective view of the sheath 205 and the system unit 301, in an implementation. The interior space of the sheath and the exterior of the system unit have the same or similar shapes, such that the system unit can fit inside (e.g., be housed) of the sheath. For example, along various axes of the sheath and system unit the sheath and system unit have the same or similar angular shapes, such as the angular taper shape having an angle θ between opposite surfaces of the sheath and opposite surfaces (e.g., left and right side surfaces) of the system unit. The opposite surfaces of the sheath can be the interior right surface and interior left surface, the exterior right surface and exterior left surface, or both. Additionally, the angle 1 between the surface (e.g., interior surface, exterior surface, or both) of the window of the top of the sheath and the back of the sheath, and the angle 1 between the surface of the display of the system unit and the back of the system unit may be the same or similar.

Figure 17A:
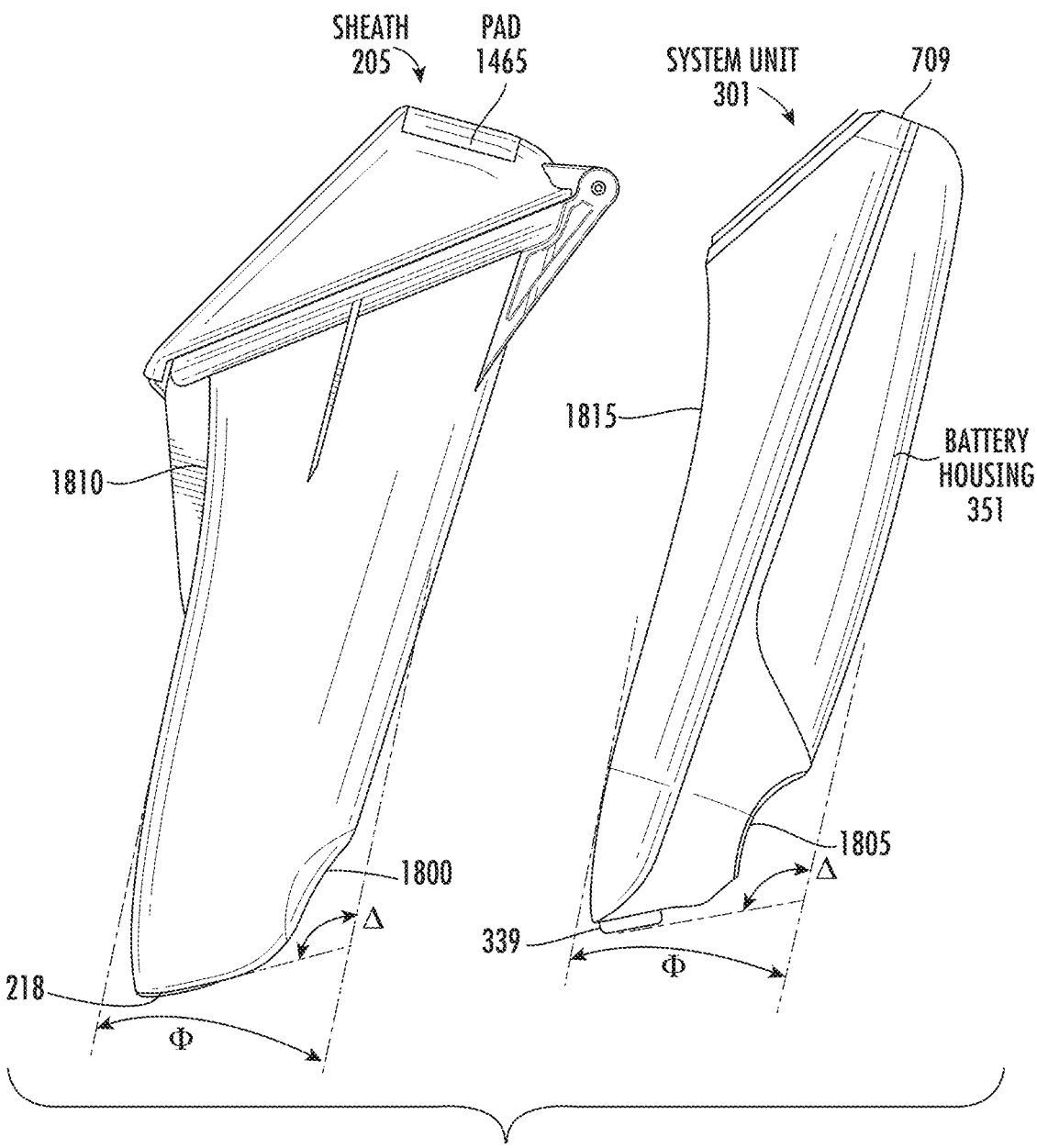
FIG. 17A shows a side view of the sheath and the system unit, in an implementation.

FIG. 17A shows a side view of the sheath 205 and the system unit 301, in an implementation. The angle Ω between the front surface (e.g., interior front surface, exterior front surface, or both) and the back surface (e.g., interior back surface, exterior back surface, or both) of the sheath and the angle Ω between the front surface and the back surface of the system unit may be the same or similar, such that the system unit can fit inside (e.g., be housed) by the sheath.

The angle A between the face (interior face, exterior face, or both) of the second window 218 of the sheath and the back surface (e.g., interior back surface, exterior back surface, or both) of the sheath, and the angle A between the probe face 339 of the system unit and the back surface of the system unit, may be the same or similar. The same or similar angles A allow the probe face 339 to contact the interior surface of the second window of the sheath without air gaps between the surface of the probe face and the surface of the second window.

During the use of the system unit, when the system unit is housed in the sheath, the sheath can be held between a user's thumb and finger on the web of skin (i.e., purlicue) that is between the thumb and index finger. The sheath can include a finger rest surface 1800 that is a concave surface on the back surface of the sheath. The finger rest surface can rest on a user's index finger, middle finger, or ring finger when the sheath is held for use between the user's thumb and index finger. An interior surface of the sheath can include a complimentary shaped convex surface that faces the interior of the body of the sheath.

The system unit can include a finger rest surface 1805 that is a concave surface on the back surface of the sheath. The convex surface inside the body of the sheath and the finger rest surface of the sheath can be mating surfaces (e.g., complementary-shaped surfaces) when the system unit is in the sheath. The complementary-shaped surfaces can inhibit the movement of the system unit in the sheath.

The front surface 1810 (exterior surface, interior surface, or both) of the sheath can include a curved surface that has a similarly shaped curve as a curved surface 1815 of the system unit. The interior curved surface of the sheath and the curved surface of the system unit can be mating surfaces.

Figure 17B:
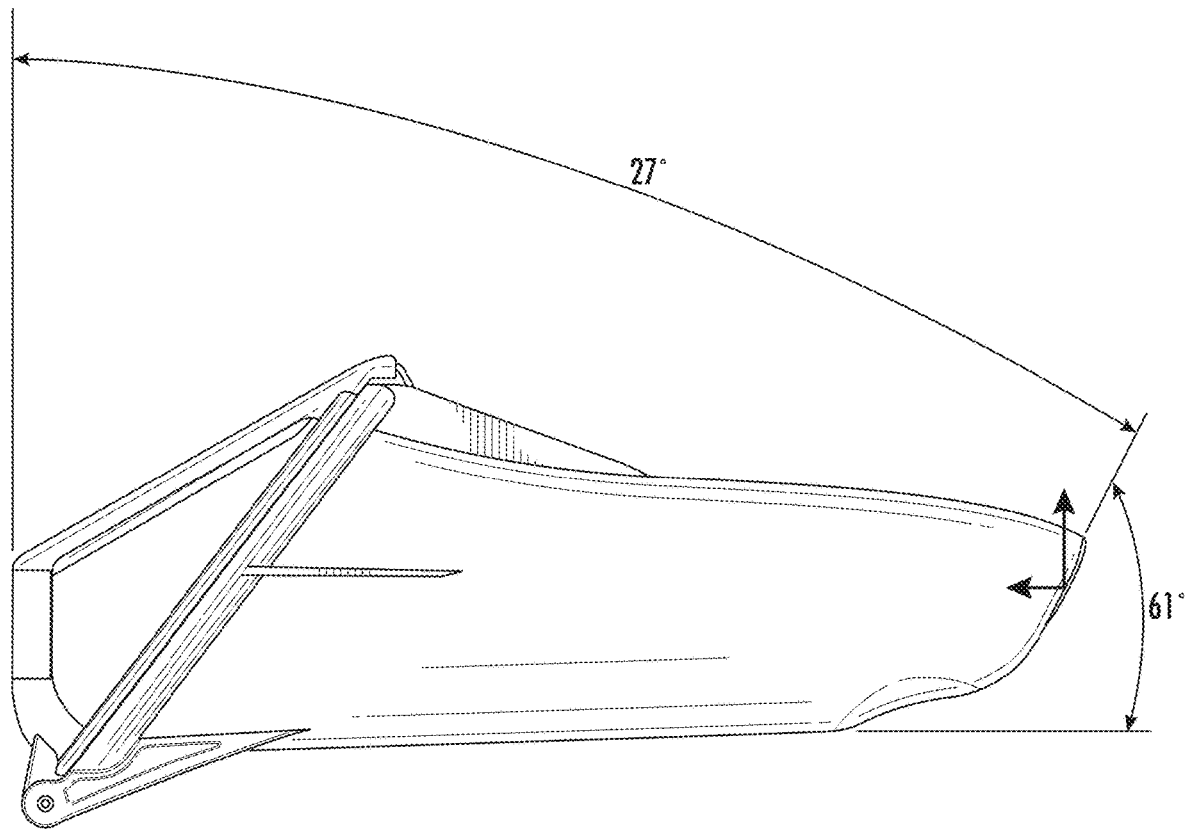
FIG. 17B is a side view of the sheath, in an implementation.

FIG. 17B is a side view of the sheath, in an implementation. The side view shows the angle between the top of the sheath and the second window. The angle may be from about 20 degrees to about 30 degrees. In an implementation, the angle is about 27 degrees (e.g., 27.02 degrees). The side view also shows the angle between the back of the sheath and the second window. The angle may be from about 55 degrees to about 65 degrees. In an implementation, the angle is about 61 degrees. The angle between the bottom of the foam pad and the second window of the sheath may be the same angle as between the top of the sheath and the second window.

When the second window is in contact with patent tissue that is oriented approximately parallel to a horizontal surface, such as an operating table, a gurney, the ground, or another horizontal feature, the center of mass of the battery of the system unit is over a user's hand when the sheath is held against the webbing of skin (i.e., the purlicue) between the index finger and thumb. With the center mass over a user's hand, the sheath with the system unit inside is relatively easy to maneuver across patient tissue with relatively fine dexterity so that the second window can be easily placed onto to target locations on the tissue, with relatively uniform pressure of the second window on a target location, and without fatigue so that the uniform contact and uniform pressure remains between the second window and the tissue when the system unit is taking oximetry measurements. That is, the angular geometry and the center of mass of the system unit and sheath facilitate the system unit making reliable oximetry measurements.

Figure 17C:
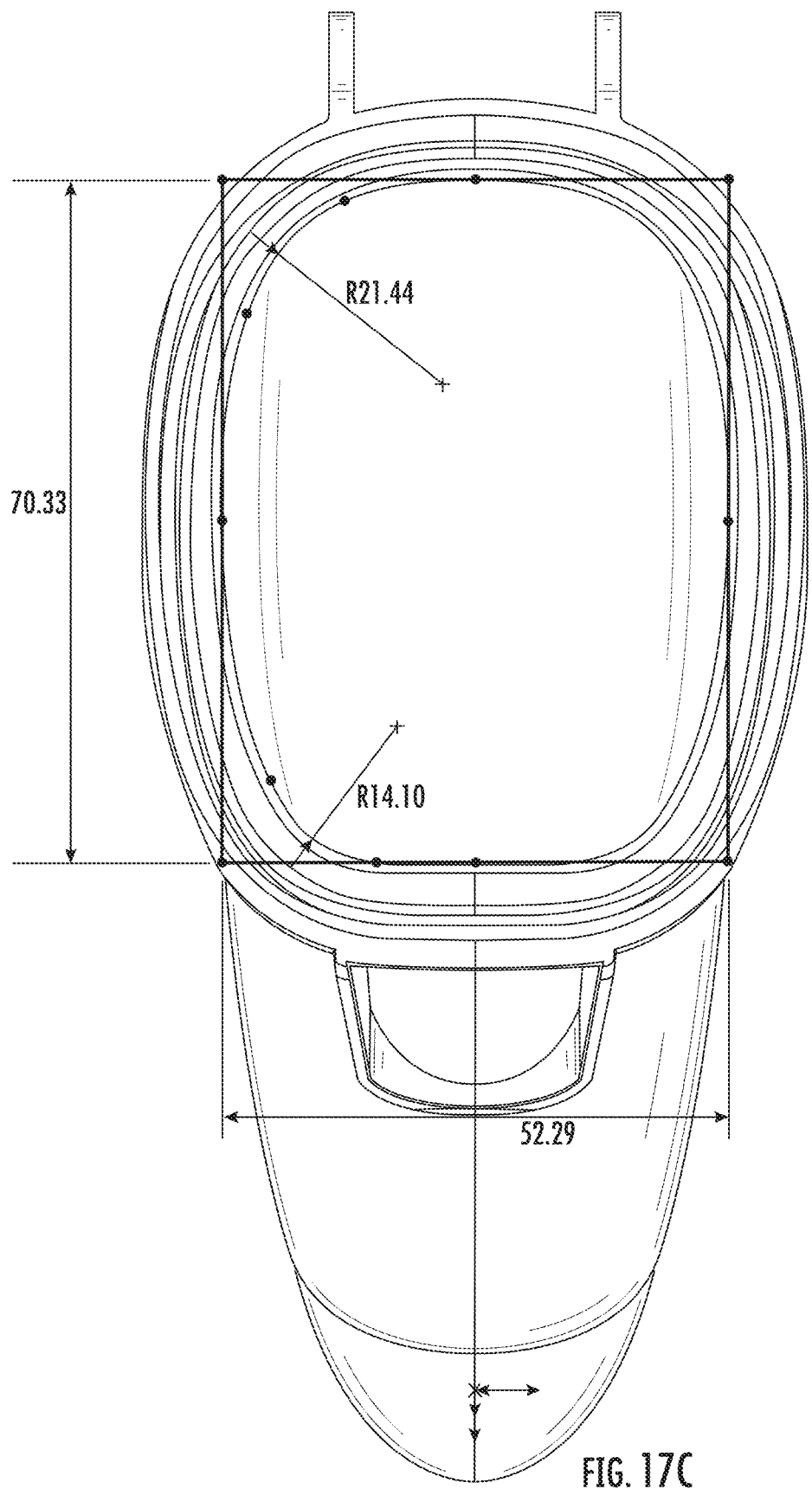
FIG. 17C is a top view of the sheath, in an implementation.

FIG. 17C is a top view of the sheath body 220 without the lid 215 attached to the body, in an implementation. The top view shows the opening at the top sheath body into which a system unit may be placed into the body. In an implementation, the opening has rounded corner portions 220a, 220b, 220c, and 220d with sides portions 220e, 220f, 220g, and 220h located between the corner portions. In an implementation, corner portions 220a and 220b have the same radius of curvature and corner portions 220c and 220d have the same radius of curvature. Corner portions 220a and 220b each have radiuses of curvatures that are different from each of the corner portions 220c and 220d. The radius of curvature of each of corner portions 220a and 220b may be from about 18 millimeters to about 25 millimeters. In an implementation, the radius of curvature of corner portions 220a and 220b are about 21.5 millimeters (e.g., about 21.44 millimeters). The radius of curvature of each of corner portions 220c and 220d may be from about 10 millimeters to about 20 millimeters. In an implementation, the radius of curvature of corner portions 220c and 220d are about 14 millimeters (e.g., about 14.1 millimeters).

The longest length of the opening between sides 220e and 220g may from about 60 millimeters to about 80 millimeters. In an implementation, the length of the opening between sides 220e and 220g is about 70 millimeters (e.g., about 70.33 millimeters). The longest length of the opening between sides 220f and 220h may from about 50 millimeters to about 60 millimeters. In an implementation, the length of the opening between sides 220f and 220h is about 52 millimeters (e.g., about 72.29 millimeters).

The differences in the radius of curvatures of the corner portion and the difference in the lengths of the side portions of the opening facilitate the lid of the sheath "locking" into the body of the sheath when the lid is closed onto the body. That is, the differences in the radius of curvatures and lengths inhibit the lid from rotating (e.g., such as if the radius of curvatures were equal) and shifting relative to the body. Thus, these curvatures and lengths inhibit a seal formed between the lid and body from being breached during normal handling and if the sheath is bumped or dropped.

Figure 18:
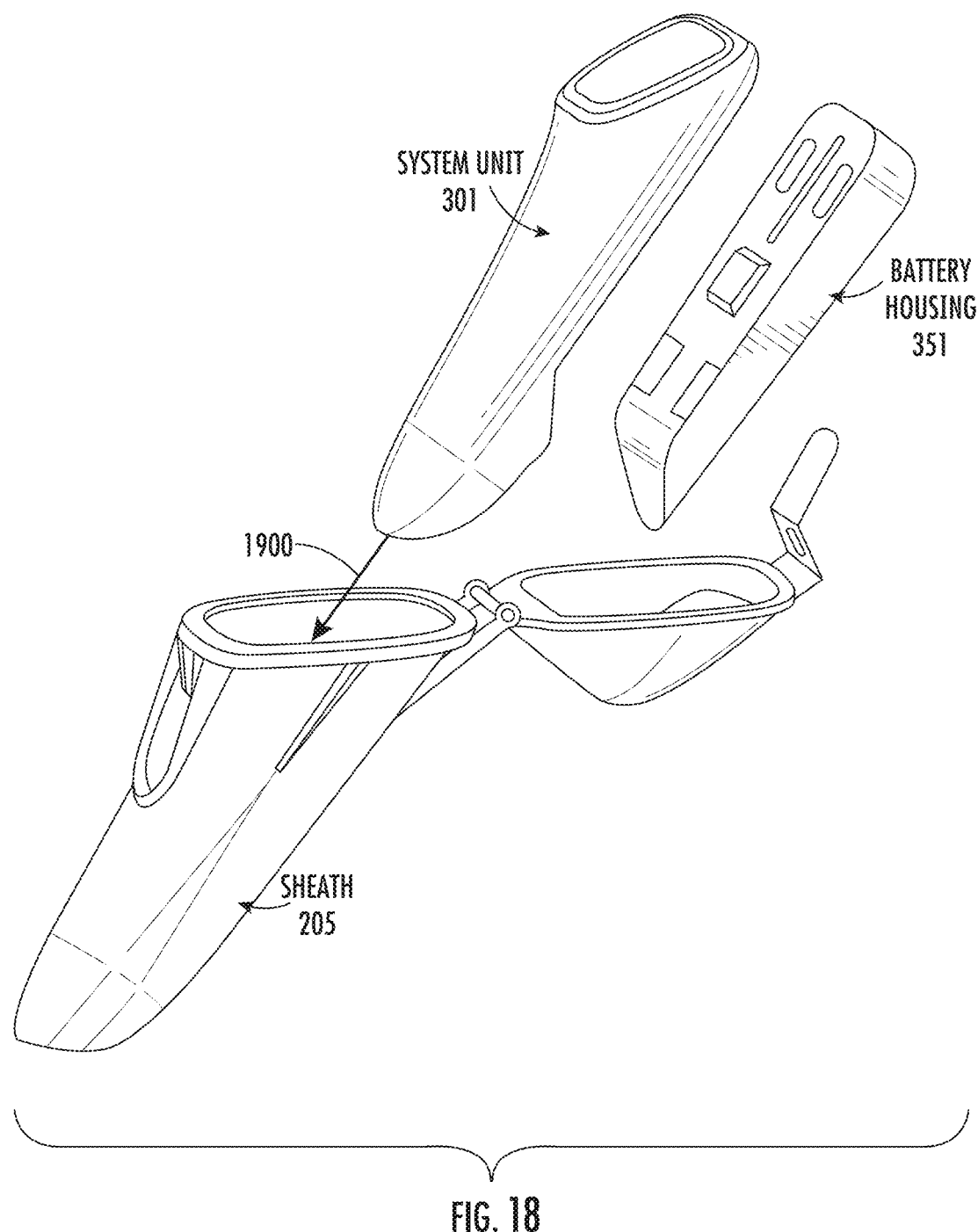
FIG. 18 shows a perspective view of the sheath, system unit, and power block, in an implementation.

FIG. 18 shows a perspective view of the sheath, system unit, and power block, in an implementation. The sheath is shown with the sheath lid open and the system unit above the opening of the body of the sheath. When the power block is placed onto the system unit, the system unit and power block may be placed into the sheath as indicated by arrow 1900. The lid may then be closed and the system unit and power block sealed in the sheath ready for use.

Figure 19:
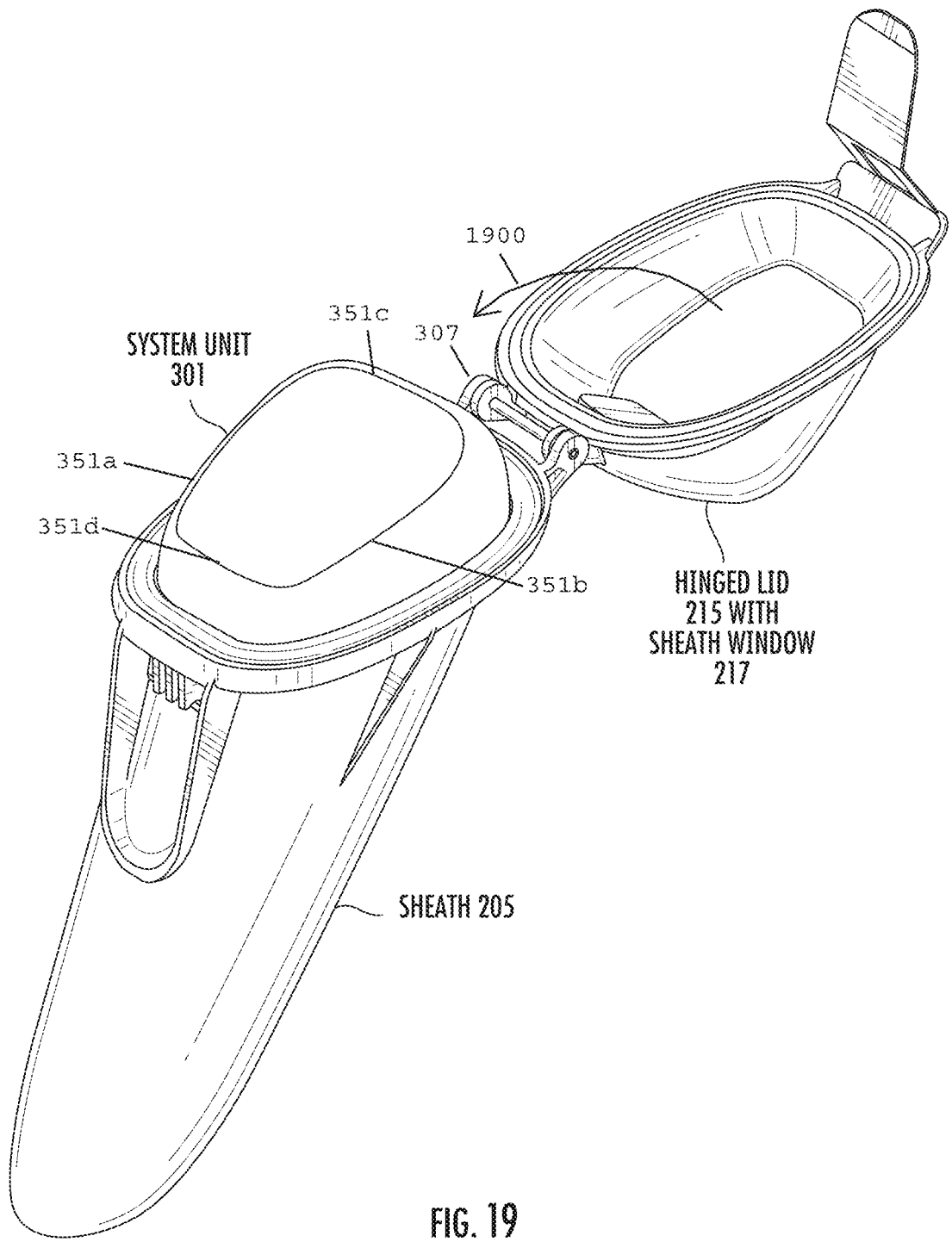
FIG. 19 shows a perspective view of the sheath, system unit, and power block, in an implementation.

FIG. 19 shows a perspective view of the sheath, system unit, and power block, in an implementation. The sheath is shown with the sheath lid open and the system unit with the power block attached is in the sheath. The probe face of the system unit may be in contact with the second window of the sheath.

In an implementation, the second window has an adhesive layer that is located on the inside surface of the second window that faces into the body of the sheath. The adhesive layer allows the probe face of the probe tip of the system unit to adhere to the inside surface of the second window when the system unit is placed into the sheath. The adhesive layer facilitates the probe face of the probe tip adhering to the inner surface of the second window so that the probe face and second window do not relative to each other during use of the sheath and system unit. The index of refraction of the adhesive may approximately match the index of refraction of the second window, the portion of the probe tip of the system unit that contacts the second window, or both.

In an implementation, an adhesive layer is located on the probe face of the probe tip of the system unit. The adhesive layer on the probe face allows for the above-described function of the adhesive layer on the inside surface of the second window. The adhesive layer on the probe face may have the same or similar characteristics as the adhesive layer described above. In an implementation where the probe face has an adhesive layer, the inside surface of the second window of the sheath does not have an adhesive layer. In an implementation where the inside surface of the second window of the sheath has an adhesive layer, the probe face of the probe tip of the system unit does not have an adhesive layer. In an implementation, the inside surface of the second window and the probe face of the probe tip both have adhesive layers.

In an implementation, both of the inside surface of the second window of the sheath and the probe face of the probe tip of the system unit do not have an adhesive layer. Thus, the probe face of the probe tip may directly contact the inside surface of the second window.

Figure 20:
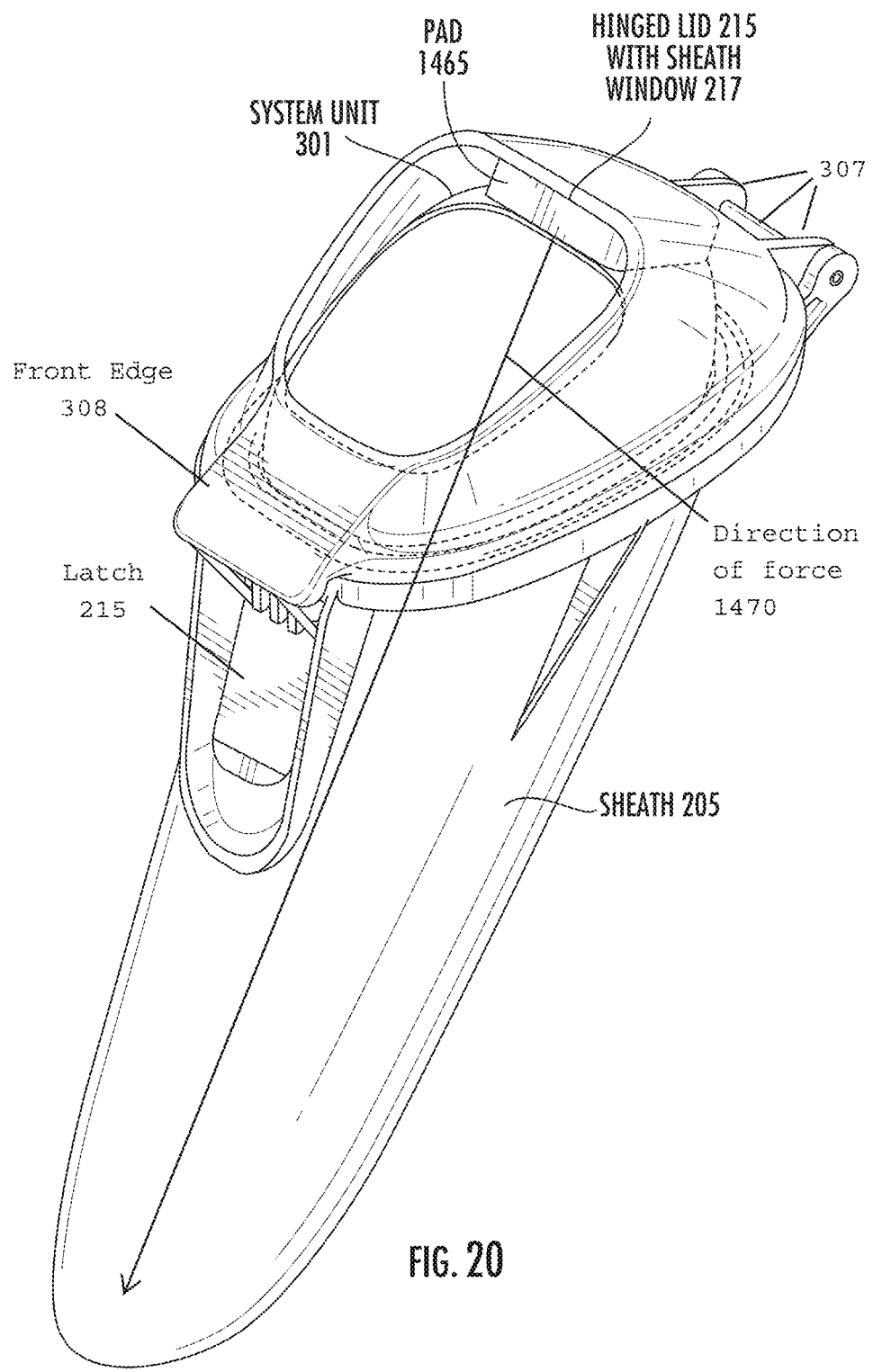
FIG. 20 shows a perspective view of the sheath, system unit, and power block, in an implementation.

FIG. 20 shows a perspective view of the sheath, system unit, and power block, in an implementation. The sheath is shown with the sheath lid closed and the system unit with the power block attached is in the sheath. The display of the system unit is visible through the first window of the lid of the sheath. Information (e.g., text, graphics, or both) that is displayed on the display of the system unit is visible to a user looking through the second window of the lid. The display and window are both proximally located with the probe face and the second window distally located when the system is ready for use. With the second window in contact with tissue, the display faces away from the tissue so that the display, through the first window, can be seen by a user.

Figure 21A:
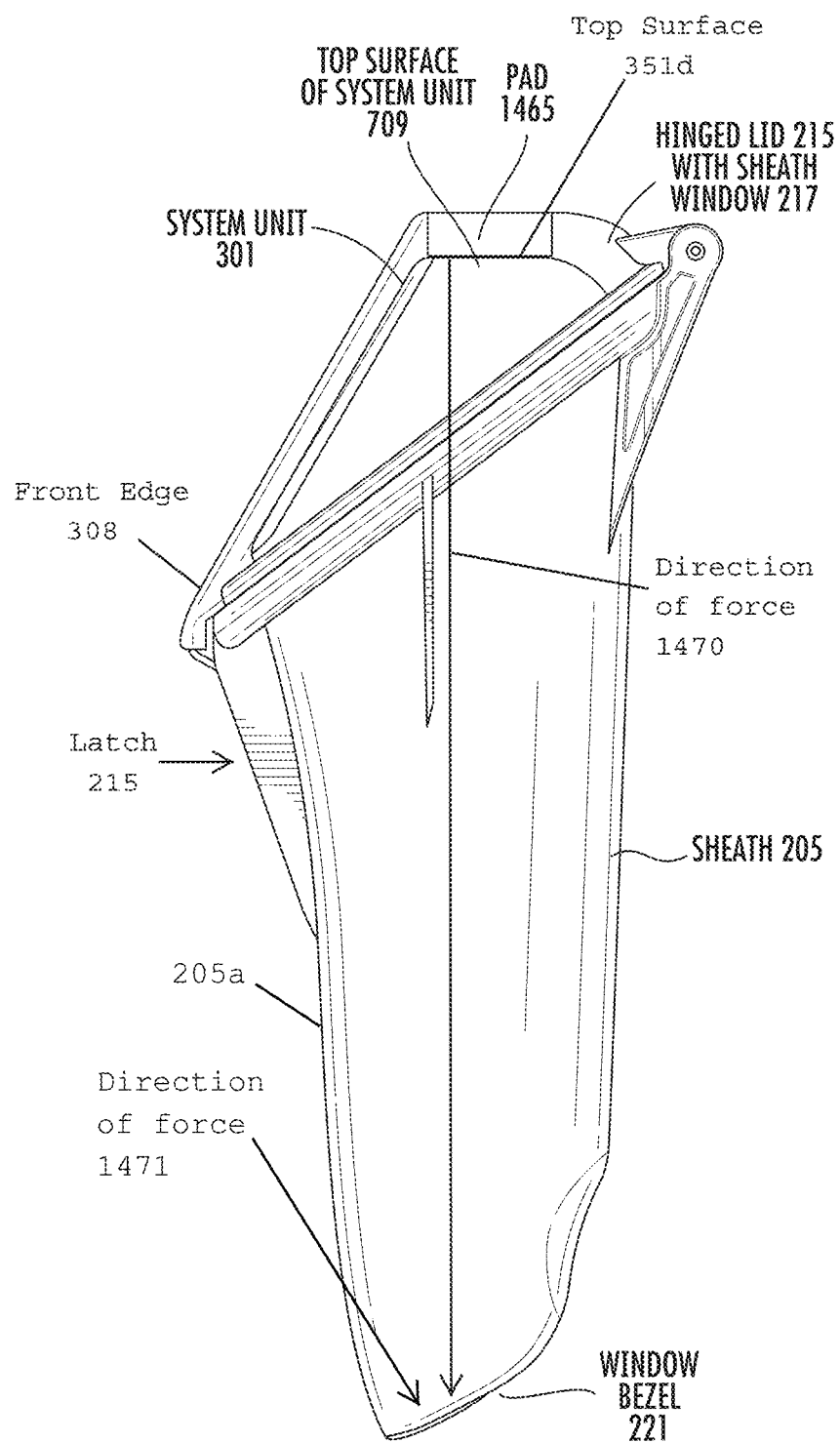
FIG. 21A shows a side view of the sheath with the system unit located in the sheath with the lid closed.

FIG. 21A shows a side view of the sheath with the system unit located in the sheath with the lid closed. This figure shows pad 1465 pressed against the top surface 709 of the sheath. When the pad is pressed against the top surface of the system unit with the lid of the sheath closed and latched, the pad pushes the system unit downward (direction of force 1470) so that the probe face of the probe tip of the system unit is pressed into contact with the sheath window 318 of the sheath. The pad provides sufficient force so that any air that might be between the probe face and the sheath window is effectively minimized or expelled from between the probe face and sheath window. As such, any air that would otherwise deflect radiation emitted from the probe face into the sheath window is reduced or eliminated.

In an implementation, an adhesive (e.g., a thin film of adhesive) is located on the surface of the sheath window that is inside the body of the sheath. For example, an adhesive may be located on the "inside" surface of the sheath window. The probe face of the system unit adheres to the adhesive and thus the inside surface of the sheath window. The adhesive can be a silicon adhesive or other type of adhesive. The adhesive may be located across the entire inside surface of the window and an outer ring of the adhesive may be the adhesive that adheres the sheath window to the body of the sheath when the window is pressed into the body. The remaining center portion of the adhesive (excluding the outer ring of adhesive) may be the adhesive that adheres to the probe face of the system unit. Thus, the inside surface of the sheath window may be coated once with an adhesive that performs two adhesive functions, namely to adhere the sheath window to the body of the sheath and adhere the probe face to the inside surface of the sheath window.

In an implementation, pad 1465 can press on the top surface 709 of the system unit to adhere the probe face to the adhesive and inner surface of the sheath window. The "outside" surface of the sheath window that is the opposite surface from the inside surface can be pressed into a relatively soft material so that the sheath window is supported from outside of the sheath when the probe face is pressed into contact with the adhesive and the inside surface of the sheath window.

In an implementation, when the system unit is placed into sheath 205 as shown in FIG. 20 with lid 215 of the sheath closed onto bottom portion 220 (e.g., body) of the sheath, pad 1465 places a force on the top surface of the battery housing, the top surface of the system unit, or both in a direction (direction of force 1470) toward the sheath window 218 (sometimes referred to as the bezel window of the sheath if the system unit includes a bezel). Thus, the bad places a force that is transferred to the probe face of the probe tip of the system unit to the inner surface of sheath window 218. The force allows for the probe face and inner surface of the sheath window to stay in contact while the system unit is used to make oximetry measurements. The force is sufficient so that the probe face and inner surface of the sheath window will not come out of contact when the sheath is oriented upward (e.g., upward with respect to the downward force of gravity of the earth).

In an implementation, where the force from the pad is applied to the top surface 351d of the battery housing, the battery transfers the applied force on the battery to the system unit.

In an implementation, when the system unit is placed into sheath 205 as shown in FIG. 20 with lid 215 of the sheath closed, the outside front surface 205a of the system unit contacts the inside front surface of the sheath. The contact of these surfaces creates a force 1471 that is directed towards the probe face. The force forces the probe face into contact with sheath window 221. The angle between force vector 1470 and 1471 makes the force between the probe face and inner surface of the sheath relatively uniform. In an implementation, the angle between the force vectors is from about 20 degrees to about 35 degrees. In an implementation, the angle between the force vectors is from about 25 degrees to about 30 degrees. In an implementation, the angle between the force vectors is from about 23 degrees to about 27 degrees.

In an implementation, the pad has a first elasticity, the lid of the sheath has a second elasticity, and the body of the sheath has third elasticity. The first elasticity is more elastic than the second elasticity and the third elasticity. The first elasticity may be in the OO durometer scale of the Shore durometers and the second and third elasticities may be in the D durometer scale of the Shore durometers. The OO scale is used for softer materials than the D scale is used for harder materials. The pad may have a Shore durometer from about OO45 to about OO55 in the OO scale. The lid may have a Shore durometer of about D80. The body may have a durometer of about 90.

The foam may be neoprene, polyethylene, cross-linked polyethylene, polyurethane, reticulated polyurethane, melamine, or another type of foam.

The lid of the sheath is a plastic material. The material can be polycarbonate, acrylic, polyethylene terephthalate (PET), PETG, polyester, acrylonitrile butadiene styrene (ABS), or other plastic material. Polycarbonate, for example, is a material the lid may be made of because the material is easy to form, can be transparent, can be easily polished, and can be sterilized by a variety of sterilization techniques and material, such as ethylene oxide (EtO), exposed to irradiation (both gamma and electron-beam), and steam autoclaving, isopropyl alcohol exposure, and other techniques and materials.

The body of the sheath is a plastic material. The material can be polycarbonate, acrylic, polyethylene terephthalate (PET), PETG, polyester, acrylonitrile butadiene styrene (ABS), or other plastic material. ABS, for example, is a material the body may be made of because the material is easy to form and can be sterilized by a variety of sterilization techniques and material, such as ethylene oxide (EtO), exposed to irradiation (both gamma and electron-beam), and steam autoclaving, isopropyl alcohol exposure, and other techniques and materials. In an implementation, the body of the sheath is metal. In an implementation, the body of the sheath is ceramic.

Because the foam is more elastic than the lid and body, the foam can compress by a distance (e.g., from about 0.2 millimeters to about 1.5 millimeters) and the force applied by the foam to the system unit (e.g., when the lid is closed, FIG. 20) is a spring force with a relatively low spring constant. Because the lid and body have low elasticities, the lid and body do not deform when the foam applies a force to the system unit when the lid is closed. Deformation of the lid or body could allow the sheath to leak, which is not desirable. Thus, the material for the lid and body are selected to have the described elasticities (e.g., lower than the foam) so that these elements do not deform when the system unit is in the sheath and the lid is closed.

In an embodiment, the pad can be a linear spring that behaves according to Hooke's Law, sometimes referred to as Hooke's Law of Elasticity. The force of a spring, such as a linear spring, is given by:

$$F=-kx \tag{1}$$

Hooke's Law is an approximation that states the extension of a spring is in direct proportion with the load added to it as long as this load does not exceed the elastic limit. Above a certain stress or force which may be referred to as the elastic limit or yield strength of an elastic material, the solid (e.g., the spring) may deform irreversibly, exhibiting plasticity. Generally, the forces discussed in this application applied to the pad to compress the pad will be within the elastic range (not plastic range) of the pad. In other implementations, the forces will exceed the elastic range of the pad. The spring contact of the foam is from about 3 Newtons per millimeter to about 5 Newtons per millimeters. In an implementation, spring contact of the foam is from about 3.9 Newtons per millimeter.

In an implementation, the latch is metal and applies a spring force to hold the lid closed to the body and thus applied a spring force in series with the pad to the system unit when the lid is closed and the latch is latched. The spring constant of the latch may be higher than the spring constant of the pad.

In an implementation the pad is positioned closer to the hinge 207 of the sheath than the front edge 308 or latch 215 of the sheath. The front edge, latch, and other portions of the lid allow a relatively large torque to be applied to the lid when the lid is closed and latch so that the force applied by the pad onto the system unit is mechanically leveraged. The mechanical leverage (i.e., mechanical advantage) allows for the force applied by the pad to system unit, and thus the for applied by the probe face to the inner surface of sheath window, to be sufficient so that the probe face and inner surface contact and do not come out of contact during use. In an implementation, the side of the foam closest to the axis of rotation of the hinge is from about 22 millimeters to about 25 millimeters. In an implementation, the side of the foam closest to the axis of rotation of the hinge is about 23.4 millimeters. In an implementation, the side of the foam farthest from the axis of rotation of the hinge is from about 41 millimeters to about 44 millimeters. In an implementation, the side of the foam farthest from the axis of rotation of the hinge is about 42.4 millimeters. In an implementation, the center of the foam from the axis of rotation of the hinge is from about 30 millimeters to about 34 millimeters. In an implementation, the center of the foam to the axis of rotation of the hinge is about 32.4 millimeters.

The torque or moment of a force with respect to a point is:

$$m = Fd \qquad (2)$$

where F is the force applied at a distance d from the point. In an implementation, distance d is a length of the offset or lever arm.

As one of skill in the art will recognize, variables such as the spring constant, the length of the lever arm of the lid and hinge, number of springs, arrangement of springs (e.g., springs in parallel and springs in series), and combinations of these can be varied to produce a desired pressure at the probe face on the inner surface of the sheath window 218 of the system unit so that the probe face and inner surface contact so that they do not come out of contact during use of the sheath and system unit when making oximetry measurement. Thus, the oximetry measurements can be reliable.

Factors that may contribute to the spring constant of the first spring (e.g., pad) and the second spring (e.g., latch) include the springs' dimensions such as the springs' length, width, or thickness, shape or cross-sectional shape of the spring which can affect a moment of inertia, the material that the spring is made of (e.g. plastic or metal), or combinations of these.

An implementation may include two or more springs in series (e.g., springs linked end-to-end), two or more springs in parallel (e.g. springs side-by-side), or a combination of springs in series and springs in parallel. For springs in parallel, the equivalent spring constant of the combination is a sum of the spring constants of each individual spring. For springs in series, to find the equivalent spring constant of the combination, add the reciprocals of the spring constants of each individual spring and take the reciprocal of the sum.

Figure 21B:
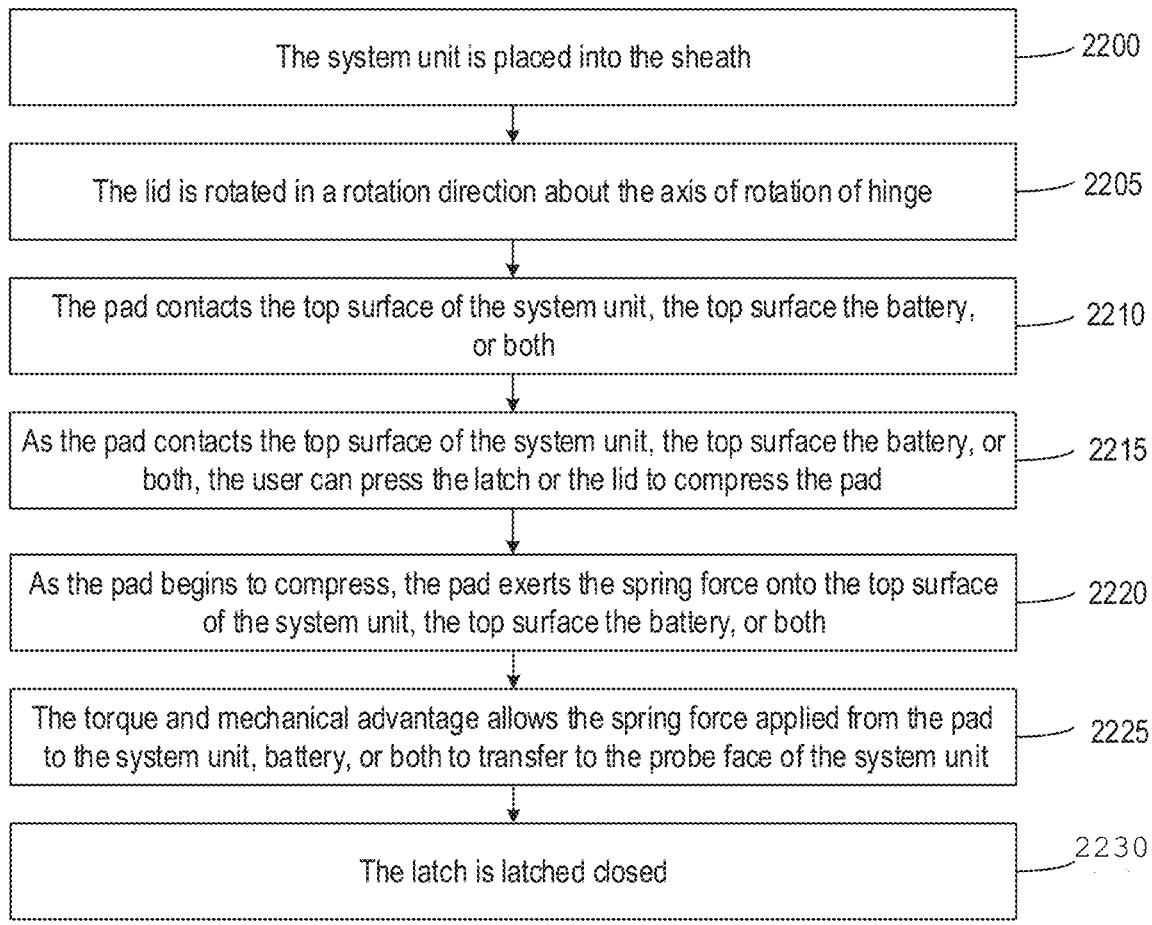
FIG. 21B is a flow diagram for a method of placing the system unit in the sheath and closing the lid so that the probe face contacts the sheath window with sufficient force for operation of the system unit to make oximetry measurements.

FIG. 21B is a flow diagram for a method of placing the system unit in the sheath and closing the lid so that the probe face contacts the sheath window 218 with sufficient force for operation of the system unit to make oximetry measurements. The flow diagram shows an example embodiment in an implementation. Steps may be added, removed, or combined without deviating from the method.

At 2200, the system unit is placed into the sheath. The system unit may be placed into the sheath by a non-sterile operator located in a non-sterile area of an operating room and a sterile operator may hold the sheath in a sterile area of an operating room. One or more curtains may separate the sterile and nonsterile areas of the operating room. The nonsterile operator may reach through the curtains to place the system unit in the sheath.

At 2205, the lid is rotated in a rotation direction (e.g., arrow 1900) about the axis of rotation of hinge 307. The lid is rotated by a user, such as the sterile operator located in the sterile area of the operating room. The lid or latch can be manipulate by the user to rotate the lid.

At 2210, the pad contacts the top surface of the system unit, the top surface the battery, or both.

At 2215, as the pad contacts the top surface of the system unit, the top surface the battery, or both, the user can press the latch or the lid to compress the pad.

At 2220, as the pad begins to compress, the pad exerts the spring force onto the top surface of the system unit, the top surface the battery, or both. The initial thickness of the pad before compressing the oximetry device is from about 6 millimeters to about 7 millimeters. In an implementation, initial thickness of the pad before compressing the oximetry device is about 6.35 millimeters. The initial thickness of the pad after compressing the oximetry device is from about 6 millimeters to about 7 millimeters. The initial thickness of the pad before compressing the oximetry device is from about 4 millimeters to about 5 millimeters. In an implementation, the initial thickness of the pad before compressing the oximetry device is about 4.48 millimeters (e.g., about 4.5 millimeters).

The torque and mechanical advantage of from the pad being closer to the hinge than the surfaces of the lid that a user presses on to close the lid allows for the user to easily compress the pad so that the pad applies the spring force as the pad compresses.

At 2225, the torque and mechanical advantage allows the spring force applied from the pad to the system unit, battery, or both to transfer to the probe face of the system unit. This transferred force allows the probe face to press against the inside surface of the sheath window 221 so that the surfaces connect with sufficient force so that the surfaces remain connected during use even if the sheath and system unit are turned upside down.

At 2230, the latch is latched into the recess pocket to seal the system unit into the sheath for use to make oximetry measurements.

Because the direction of the force is directed straight from the pad and through the oximeter device, the pressure of the probe face against the inner surface of sheath window 221 is relatively uniform. Uniform pressure allows for the refractive index at the interface between probe face and inner surface to be uniform and allow for the light from the system unit to be uniformly transmitted from the probe face and through the sheath window 218 to tissue of a patient allowing for more accurate oximetry measurements. The refractive index is uniform because the uniform pressure facilitates the probe face and the inner surface of the sheath window to be approximately parallel. When the surface are approximately parallel any gas remaining between the surfaces is substantially uniformly distributed, and the uniform gas distribution will allow for uniform refraction of light that passes through the gas.

The display has left-right symmetry. And the angle between the left side 351a and the right side 351b of the display approximately matches the angle between the left and right sides of the opening of the body of the sheath (FIG. 19). The angles are from about 5 degrees to about 45 degrees. The angles are a keying feature that allow the system unit to be placed completely in the sheath one way. In an implementation, the display and the opening of the body of the sheath do not have front back symmetry (e.g., for the sheath between the sides nearest the hinge and latch). In an implementation, one or more of the surfaces of the system unit and the sheath include mechanical keying features (e.g., slot and tabs) that allow the system unit to be placed in the sheath in only one orientation. For example, if the oximeter device is placed in the sheath sideways or backwards, from about 60 millimeters to about 80 millimeters will extend from the sheath. In an implementation, if the oximeter device is placed in the sheath sideways or backwards, about 70 millimeters will extend from the sheath. This if the oximeter device is placed in the sheath sideways or backwards, a user will have a large length of the oximeter device to hold so that the oximeter device can easily be removed from the sheath and not get lodged in the sheath with little or no portion of the oximeter device to hold to remove the device. The oximeter device is about 178 millimeters long, thus about 40 percent of the oximeter device will be outside of the body of the sheath if the oximeter device is placed in the sheath sideways or backwards.

In an implementation, information is displayed on the display in an orientation where the text or other information is arranged for reading from left to right (e.g., from side 315*a* to side 351*b*) where the text is upright with the top of text (e.g., tops letters) nearest to side 315*c* and the bottom of text (e.g., bottoms of letters) nearest to side 351*d*.

Figure 22:
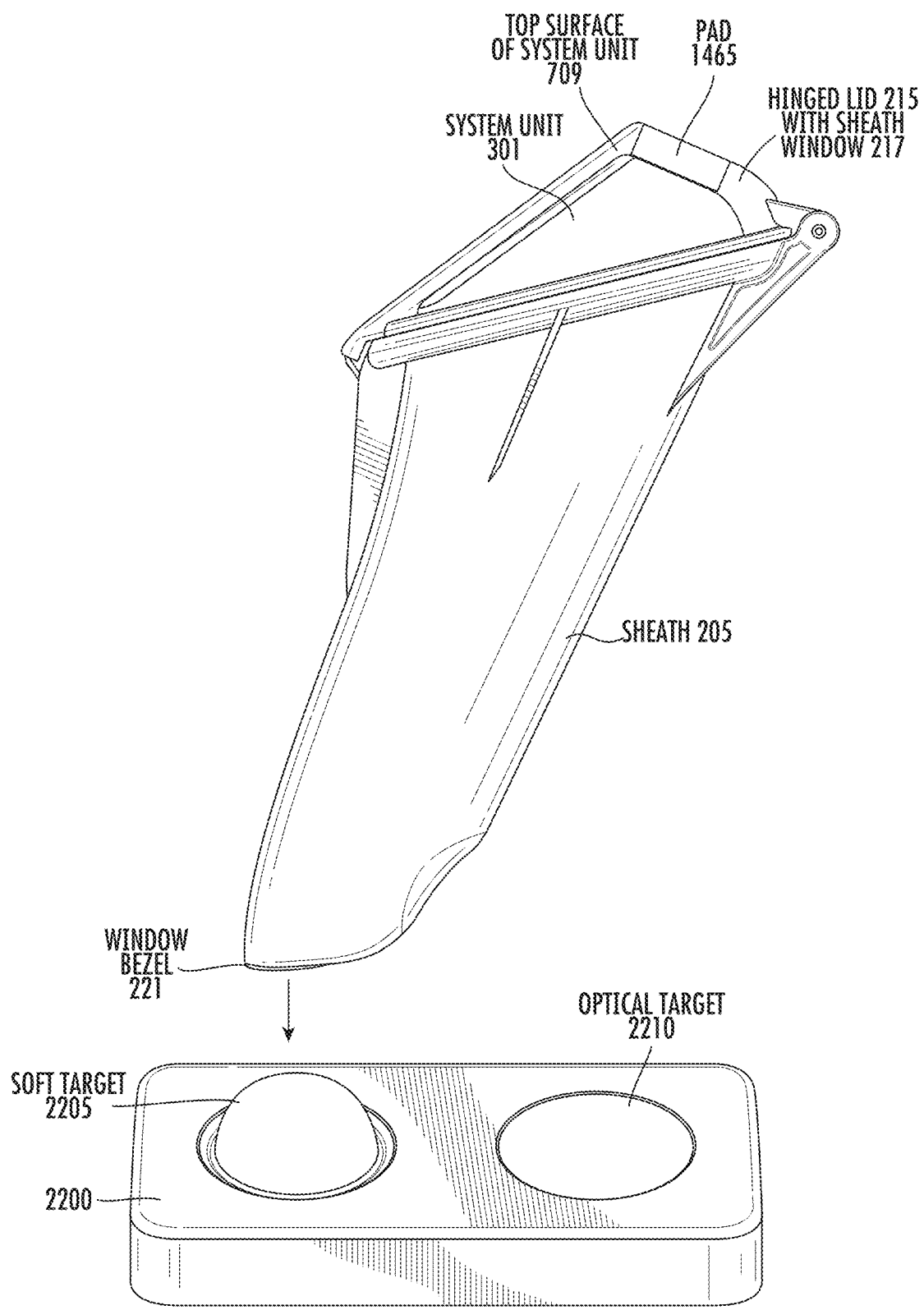
FIG. 22 shows an optical window tool that includes a soft target and an optical target.

FIG. 22 shows an optical window tool 2200 that includes a soft target 2205, which may be formed of a relatively soft plastic material or a relatively soft rubber material. The soft target may have a dome shape or other shape. The sheath window 218 can be pressed onto the soft target when the system unit is placed into the sheath and the lid is closed to adhere the probe face of the system window to the inside surface of the sheath window. The thickness of the material directly underneath optical target 2210 may be made as uniform as possible to ensure consistency of optical sampling performed on the optical target 2210.

The optical window tool may include an optical target 2210. After the inner surface of the sheath window contact, the sheath window can be contacted to the optical target so that the contact between the inside surface of the sheath window and the probe face may be analyzed. The contact between the inside surface of the sheath window and the probe face may be analyzed to determine whether there are any air pockets trapped between the inside surface and the probe face. The system unit can run an optical analysis to determine whether any air pockets are present between the inner surface and the probe face. The LEDs of the system unit can transmit light onto the optical target and the photodetectors can detect the after the light is reflected from the optical target. If the detected reflection is within predetermined parameters, then the system unit can determine whether the contact is adequate or inadequate. If the contact is adequate, the system unit may display a message indicating that the contact is adequate and normal operation of the system unit may proceed. If the contact is inadequate, the system unit may display a message indicating that the contact is inadequate and that the sheath window needs to be pressed onto the soft target again and another optical test using the optical target should be run.

In an embodiment, the system unit can illuminate and collect reflected light from a color code, a QR (i.e., quick response) code, or both to collect information encoded in the one or more colors of a color code or from a QR code. The color code may include one or more colors. The color code may be located on a color card, a box, a brochure, a label, a device, such as the sheath, or another device. The colors of the color code may be arranged in an array on the device that the colors are on. The color code may include coded information that the system unit can identify by identifying the colors included in the color code. The coded information may be encrypted and the system unit may decrypt the coded information subsequent to identifying the colors in the color code. The system unit may use the coded information to make decisions for how the system unit operates. For example, the coded information my include information that identifies a sheath, a batty housing, or anther device as authenticated and valid device (e.g., from a known and trusted source) or an unauthenticated and invalid device (e.g., from an unknown and untrusted source). Based on the authenticity or unauthenticity of a device, the system unit may determine whether the system unit will operate with the device. The coded information may include information for a melanin concentration of tissue of a patient. The system unit may use the melanin information when determining oximetry information (e.g., oxygen saturation) for the tissue. The coded information may be used by the system unit for affecting how one or more method steps of a method are performed.

The system unit may be adapted to detect and read a one-dimensional QR code, a two-dimensional QR, or both of these codes. The QR code may include encrypted or descrypted information and the information detected by the system unit may be used the as described above with respect to a color code.

In an implementation, if the accelerometer detects an accelerometer incident (e.g., bump or drop to the sheath and system unit, the system unit can direct a user via one or more message displayed on the display to run an optical test using the optical target to check the contact between the inner surface of the sheath window and the probe face. If the optical test indicates that the contact is inadequate, then the system unit may display a message informing a user to press the sheath window onto the soft target to attempt to re-adhere the inner surface to the probe face and then run another optical test using the optical target. This process may be repeated until contact is adequate or it is determined that one or both of the sheath and system unit should be replaced.

In another implementation, a gel or liquid is positioned between the probe face and sheath window to aid in expelling air between the probe face and sheath window. In one implementation, one or both surfaces of the sheath window are reflected with an anti-reflection coating that provides antireflection for red light in the visible spectrum, infrared light in the infrared spectrum, or both. Reducing or eliminating light reflection at the operative wavelength of light from the sheath window and used by the system unit facilitates obtaining more accurate oximetry measurements because unknown reflections are reduced or eliminated compared to a sheath window not having reflective coatings.

Figure 23:
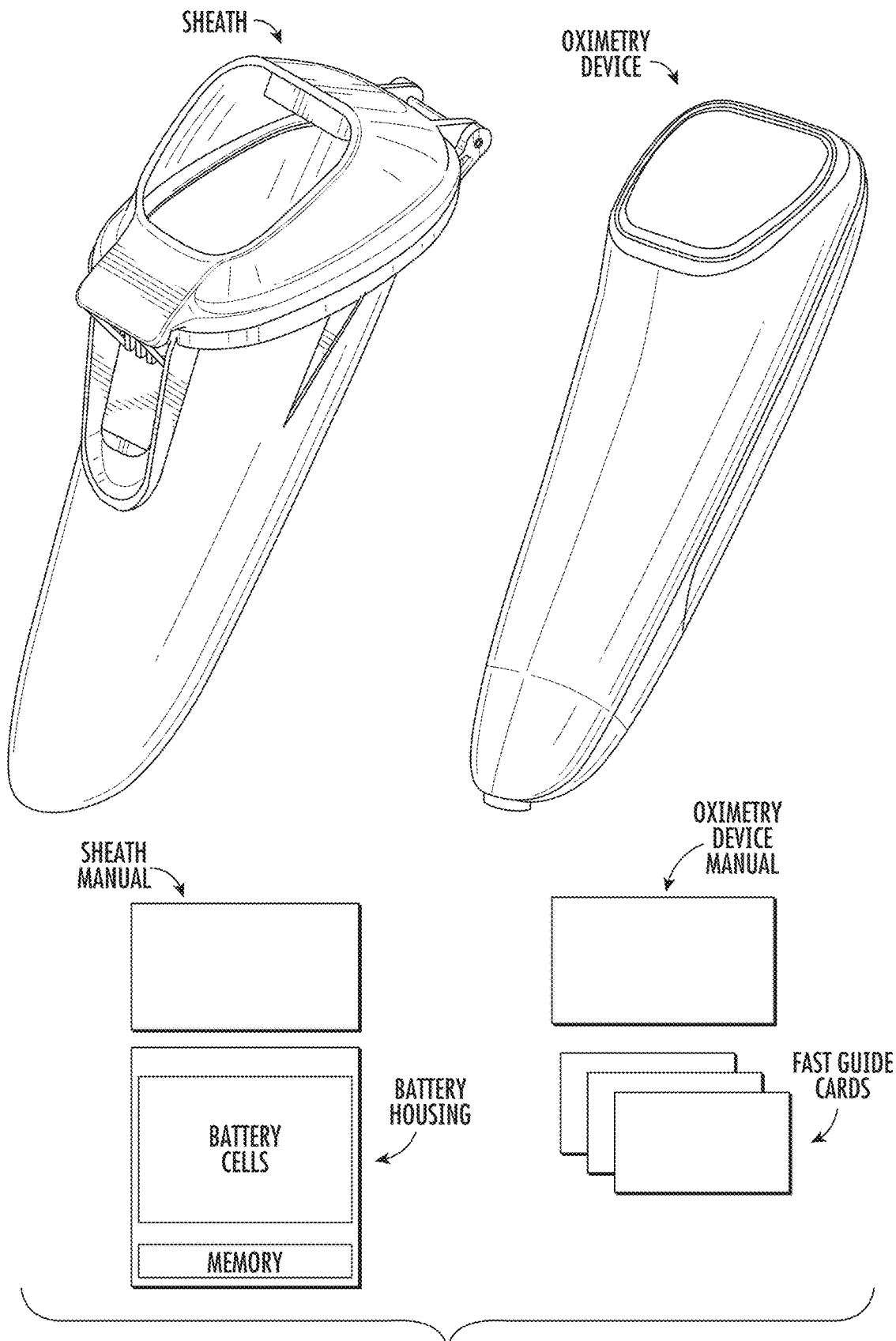
FIG. 23 shows an oximeter and sheath kit, in an implementation.

FIG. 23 shows an oximeter and sheath kit, in an implementation. The kit may include the sheath, oximeter, power block, quick reference cards for operation of the sheath and oximeter. The kit may also include instruction one or more instruction manuals. The kit may be provided in a sealed container (e.g., a box) that can be opened prior to use of the devices. The sealed container can keep the kit contents sanitary or sterile.

Figure 24:
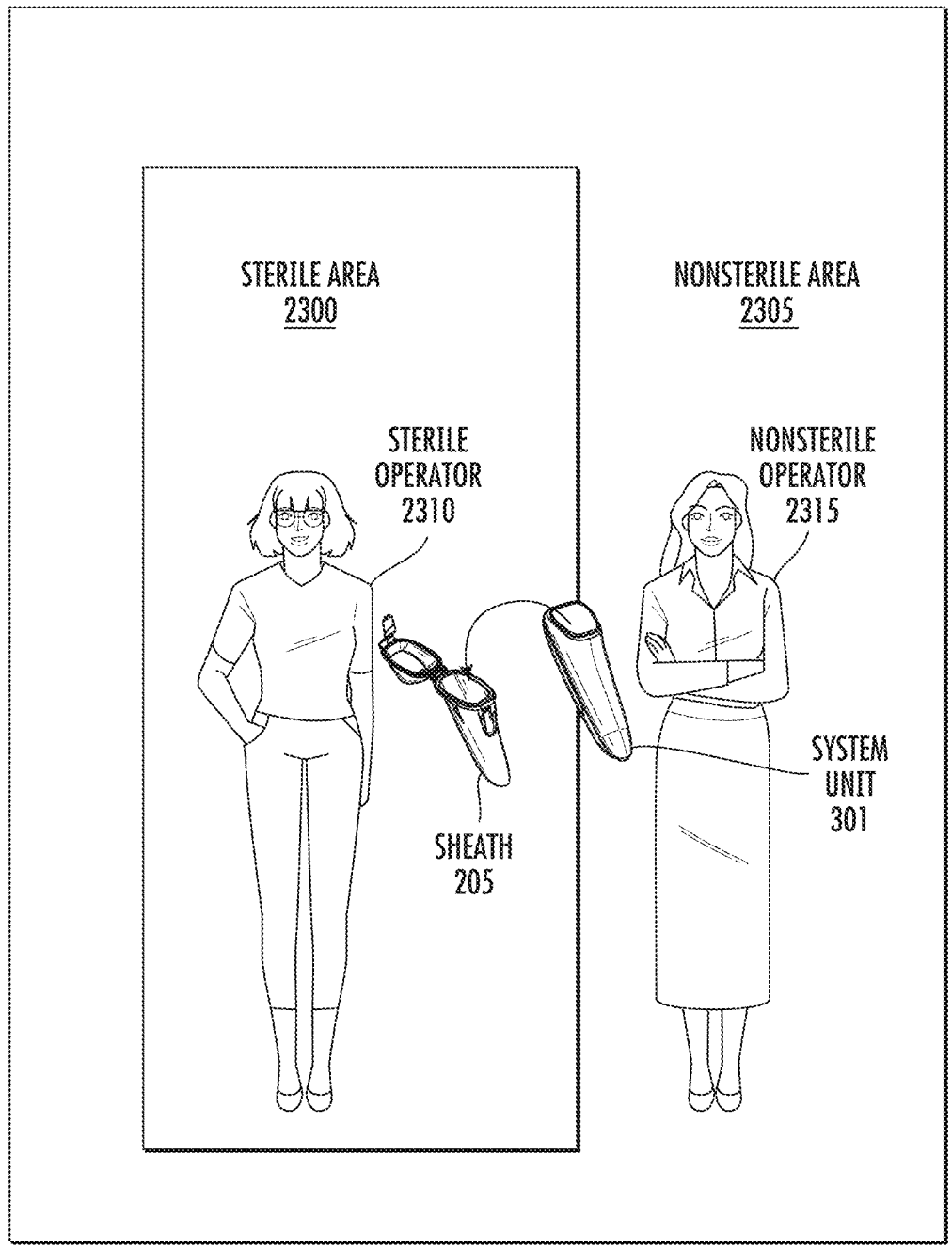
FIG. 24 shows a use environment implementation.

FIG. 24 shows a use environment implementation. FIG. 25B show the steps of a method in a series of image for use of the sheath and system unit in the use environment, such as an operating theater. There is a top row and a bottom row in FIG. 25B. The top row represents the non-sterile operator operating in the nonsterile area of the operating area. The bottom tow represent the sterile operator operating in the sterile area of the operating area.

The use environment may be an operating room in a hospital, surgical center, doctor's office, or other medical location or facility. The use environment includes a sterile area 2300 and a non-sterile area 2305 that is outside of the sterile area. In an implementation, a sterile operator 2310 (i.e., person, such as a sterile nurse) is in the sterility area and a non-sterile operator 2315 is outside of the sterile area in the non-sterile area. In an implementation where the sheath is intended to remain sterile during use, the sterile operator in the sterile area may unpackage a sterile sheath for use. A non-sterile operator may unpackage a system unit, which may be sterile or sanitary. The sterile operator may open the sheath lid so that the system unit can be placed into the sheath. The non-sterile operator may reach into the sterile area to place the system unit into the sheath without touching any portion of the sheath and the system unit not touching an exterior portion of the sheath. The sterile operator may close the lid of the sheath and latch the latch. Because the non-sterile operator has not touched the sheath and the system unit has not touched any outer surface of the sheath, the sheath remains sterile for use. In an implementation, the sterile area can be a sanitized area and the sterile operator can be a sanitary operator.

In an embodiment, the power block is placed on the system unit before the system unit is placed in the sheath for use. The nonsterile operator may attach the power block to the sheath before placing the system unit and power block in the sheath. The system unit may be turned on before the nonsterile operator places the system unit and battery pack in the sheath. The sterile operator may perform a contact test of the probe face of the system unit to the second window of the sheath, which is described above with respect to FIG. 22 for using the optical window tool.

Figure 25A:
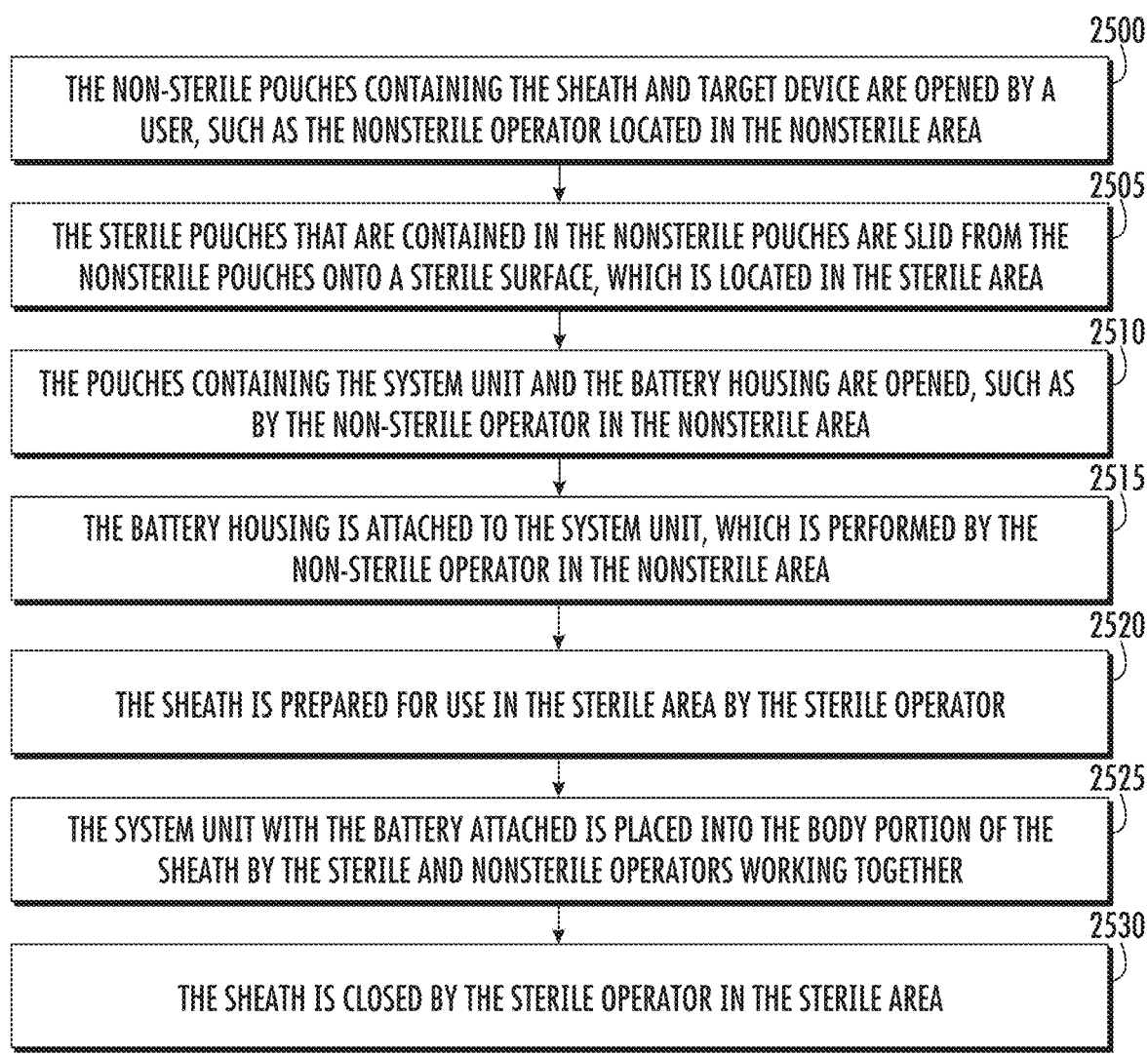
FIG. 25A is a flow diagram for a method of placing the system unit in the sheath in an operating theater, such as the operating theater shown in FIG. 24, in an implementation.
Figure 25B:
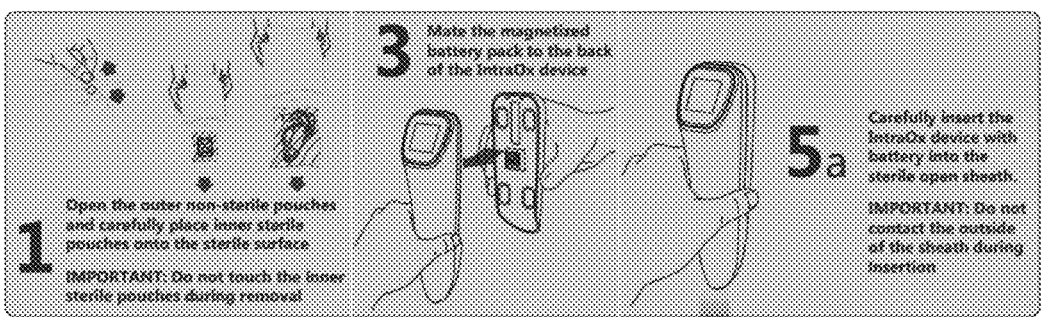
FIG. 25B show the steps of a method in a series of image for use of the sheath and system unit in the use environment, such as an operating theater.
Figure 25B:
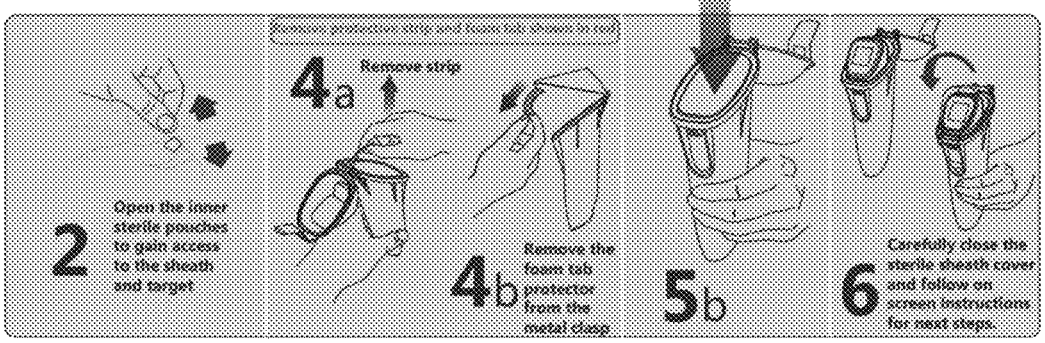

FIG. 25A is a flow diagram for a method of placing the system unit in the sheath in an operating theater, such as the operating theater shown in FIG. 24, in an implementation. The method facilitates that the outer surfaces of the sheath remain sterile before use, that a patient is not contaminated by the system unit, and the system unit is not contaminated by the patient. The flow diagram shows an example embodiment in an implementation. Steps may be added, removed, or combined without deviating from the method.

The sheath and a target device used with the sheath and system unit are located inside of sterile pouches and each sterile pouch is located in a nonsterile pouch. The system unit and battery housing may be located inside non-sterile pouches or may be located in sterile pouches, which are located in sterile pouches.

At 2500, the non-sterile pouches containing the sheath and target device are opened by a user, such as the nonsterile operator located in the nonsterile area. The user opening the nonsterile pouches may not touch the sterile pouches or the inside surfaces of the nonsterile pouches.

At 2505, the sterile pouches that are contained in the nonsterile pouches are slid from the nonsterile pouches onto a sterile surface, which is located in the sterile area.

At 2510, the pouches containing the system unit and the battery housing are opened, such as by the non-sterile operator in the nonsterile area.

At 2515, the battery housing is attached to the system unit. The attachment may be performed by the non-sterile operator in the nonsterile area.

At 2520, the sheath is prepared for use in the sterile area. Preparation may include the removal of foam cover that covers at least a portion of the metal latch of the sheath. The foam cover inhibits the metal sheath from becoming scratched or nicked prior to use and thus inhibits the latch from being able to become snagged and open the lid after being closed. Inhibiting the metal latch from becoming scratched or nicked additionally inhibits the latch from snagging and tearing surgical gloves.

At 2525, the system unit with the battery attached is placed into the body portion of the sheath. The sterile operator may hold the sheath with the lip opened in the sterile area. The nonsterile operator may place the system unit into the sheath without touching any outside surface of the sheath to inhibit the outside surfaces of the sheath from being contaminated.

At 2530, the sheath is closed. The lid is rotated to connect to the O-ring held in the body of the sheath and the latch on the lid is latched to the body. The sheath may be closed by the sterile operator. Thereafter, a user may follow one or more instructions on the display to operate the system unit.

Figure 26:
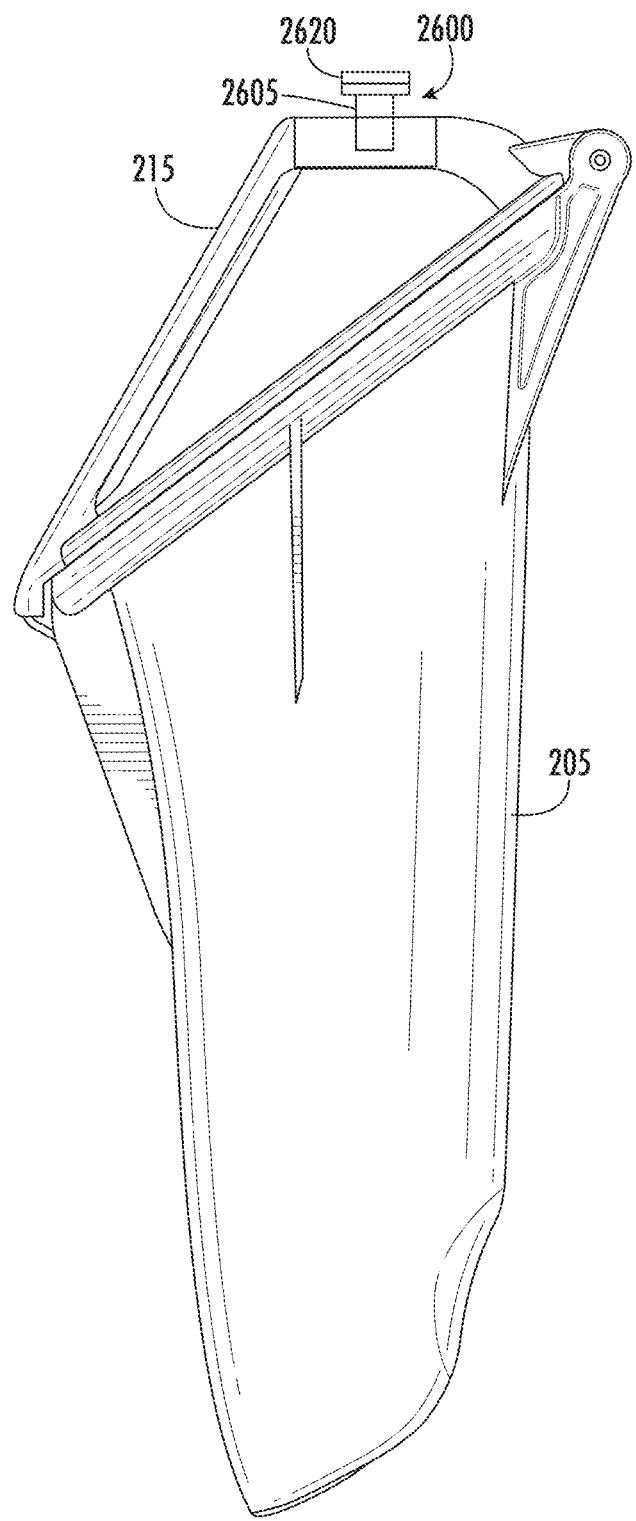
FIG. 26 shows the sheath in an implementation where the sheath includes a vent.

FIG. 26 shows sheath 205 in an implementation that includes a vent 2600. Vent 2600 is located in lid 215 of the sheath. In an implementation, the vent is located in the body of the sheath. The vent allows gas inside the sheath to pass through the vent and outside of the sheath, such as when the pressure (e.g., due temperature increase) of the pressure inside the sheath increases. The vent also allows gas to pass from outside of the sheath into the sheath, such as when the gas inside the sheath decreases. The vent does not allow bacteria, viruses, prions, water droplets, or other debris to pass through the vent. Because the vent allows gas to pass through the vent when the gas inside the sheath warms or cools, pressure inside of the sheath can remain approximately isobaric. Approximately isobaric pressure inside the sheath inhibits the sheath (e.g., body, lid, seal, first window, second window, or any combination of these elements) from mechanically deforming and inhibits joined surface (e.g., glue joints, gasket joints, O-ring, or other joints) of the sheath from leaking. The vent thus prevents bacteria, viruses, prions, or other debris inside the sheath from reaching a patient and prevents any contaminants outside of the sheath from reaching the system unit inside the sheath.

The lid includes a hole (e.g., a round hole or another shape hole) that extends through the lid. At least a portion of the vent is located in the hole and another portion of the vent is located outside of the hole.

Figure 27:
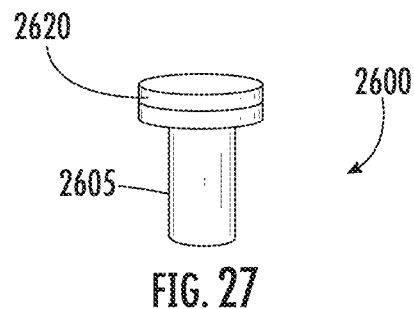
FIG. 27 shows a perspective view of the vent, in an implementation.

FIG. 27 shows a perspective view of the vent, in an implementation. The vent includes a frame 2605 and a vent material 2620. The vent material may be a filter that facilitates the filtering described above.

Figure 28:
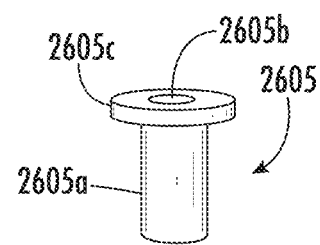
FIG. 28 shows a perspective view of the vent frame, in an implementation.

FIG. 28 shows a perspective view of the frame, in an implementation. The frame includes a tube 2605*a* that has an opening 2605*b* that extends from a first end of the frame to a second end of the frame. The tube may have a profile (e.g., a round profile) that compliments the shape (e.g., round shape) of the hole in the lid. At least a portion of tube is located in the hole.

The first end of the tube is a proximal end that is outside of the lid. The second end of the tube is a distal end that may be flush with a bottom surface of the lid, may by be inside the hole formed in the lid material, or may extend past the bottom of the hole in the lid and past a bottom surface of the lid. FIG. 26 shows the second end of the tube extending past the bottom surface of the lid.

The tube is sealed to the lid material around the hole. The vent may be epoxied to the lid, plastic welded to the lid (e.g., via ultrasonic welding, laser welding, or another weld process), integrally formed with the lid, attached to the lid by one or more fasteners, or otherwise attached to the lid at the hole location.

The radius of the second window of the sheath is from about 4 millimeters to about 5 millimeters. In an embodiment, the radius of the second window of the sheath is about 4.5 millimeters. The opening in the body of the sheath that holds the second window is less than the radius of the of the second window by about 1 micrometer to about 3 micrometers.

In an implementation, the frame includes a flange 2605*c* that is attached to the first end of the tube. In an implementation, the frame does not include a flange. When the frame is attached to the lid, the flange is located outside of the sheath and is above the lid as shown in FIG. 26. The flange may be generally flat with top and bottom surfaces that are approximately parallel. The flange may have a round profile. Opening 2605*b* extends through the flange.

Vent material 2620 is attached to a top surface of the flange. The vent material may be epoxied to the top surface of the flange, welded to the top surface of the flange (e.g., ultrasonically welded, laser welded to the flange, or another weld process).

Figure 29:
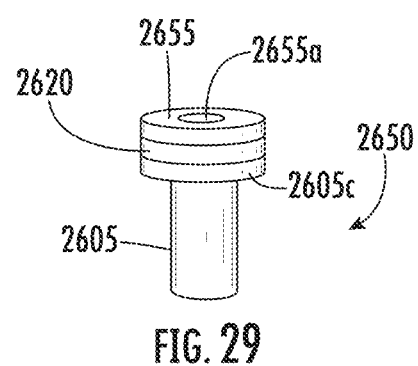
FIG. 29 shows a perspective view of a vent, in an embodiment.

FIG. 29 shows a perspective view of vent 2650, in an embodiment. The vent is similar to vent 2600 but differs from vent 2600 in that vent 2650 includes a cap 2655. The cap includes a hole 2655a that extends through the cap. The vent material may be located between the cap and the flange. The cap may be attached to the flange to hold the vent material by one or more fasteners (e.g., screws), may be welded to the flange (e.g., ultrasonically welded, laser welded to the flange, or another weld process). The hole in the frame and hole in the cap approximately register.

The frame and cap may be formed of the same material or different materials. The frame may be formed of a plastic material (e.g., polypropylene (PP)), a metal material, an organic material, a composite material (aluminum composite panels (ACP)), anther material, or a combination of these materials (e.g., PP and ACP). The frame material may have a relatively small pore size, such as 2-3 micrometers or less. The cap may be formed of the same material that the frame if formed from or a different material. The frame and cap may not be adapted to vent gas from inside the sheath to outside the sheath and allow gas to pass from outside of the sheath to inside of the sheath.

Figure 30:
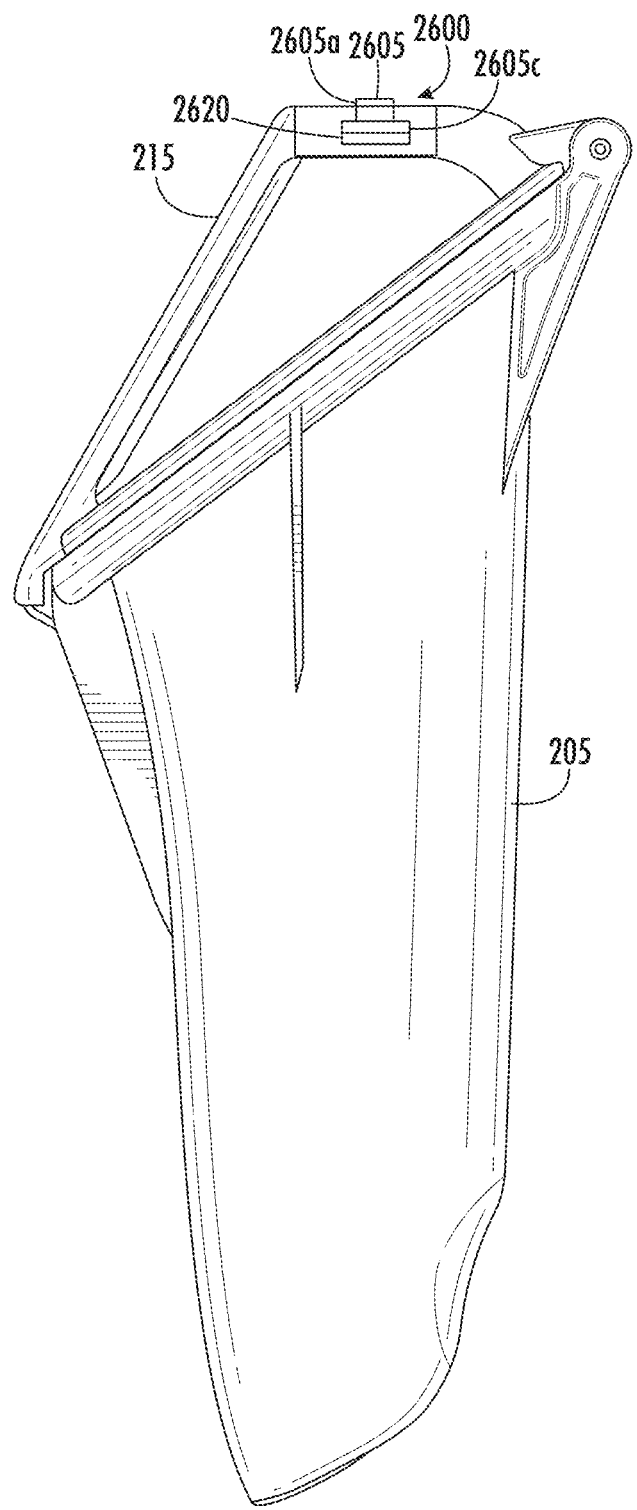
FIG. 30 shows a sheath in an implementation that includes a vent.

FIG. 30 shows sheath 205 in an implementation that includes vent 2600. Vent 2600 is oriented so that flange 2605c and vent material 2620 are below the bottom surface of the lid and in the interior space of the sheath when the lid is closed. The tube 2605a of frame 2605 extends through the hole in the lid where gases from inside the sheath can be vented outside of the sheath through the end of the tube, and where gasses from outside of the sheath can enter the vent for transmission through the vent into the interior space of the sheath. The end of tube 2605a can extend above a top surface of the lid as shown in FIG. 30 or can be flush or below the top surface of the lid. The vent facilitates that gas does not pass through any other portion of the sheath expect through the vent.

In an implementation, the frame does not include a flange and the vent material is be attached to tube 2605a to a top surface of the tube, to a sidewall of the tube, or both. The vent material may be attached to the tube as described above by a cap, epoxy, another device, or another adhesive.

Figure 31:
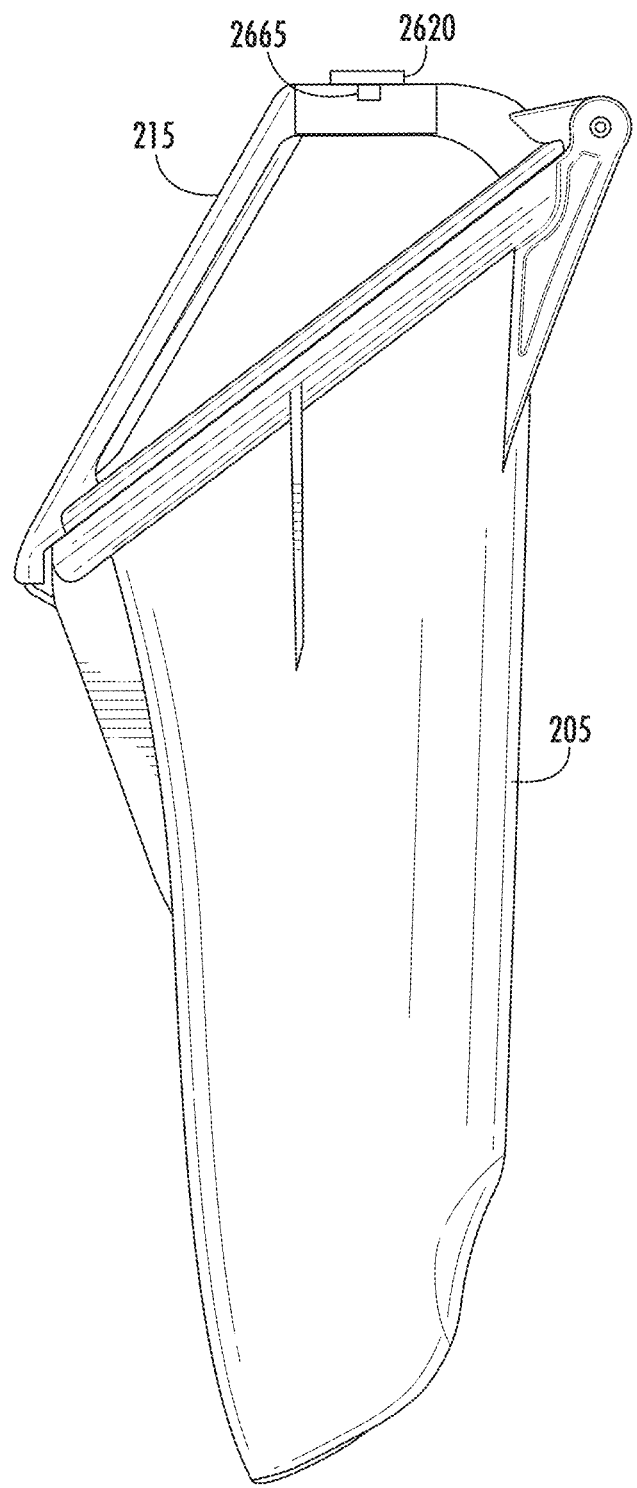
FIG. 31 shows the sheath with the vent material connected to the top surface of the lid, in an implementation.

FIG. 31 shows the sheath with the vent material 2620 connected to the top surface of the lid, in an implementation. The lid includes a through hole 2665 that extends through the top wall of the lid. Vent material 1620 is connected to the top wall and covers the through hole so that gases vent through the vent material and do not go around the vent material or vent through any other portion of the sheath. The vent material may be attached to the lid by a variety of techniques, such as epoxy, plastic welding, or other techniques. In alternative implementations, the vent material is connected to a different panel of the lid (e.g., front panel, back panel, or one of the side panels) or is connected to the body of the sheath.

Figure 32:
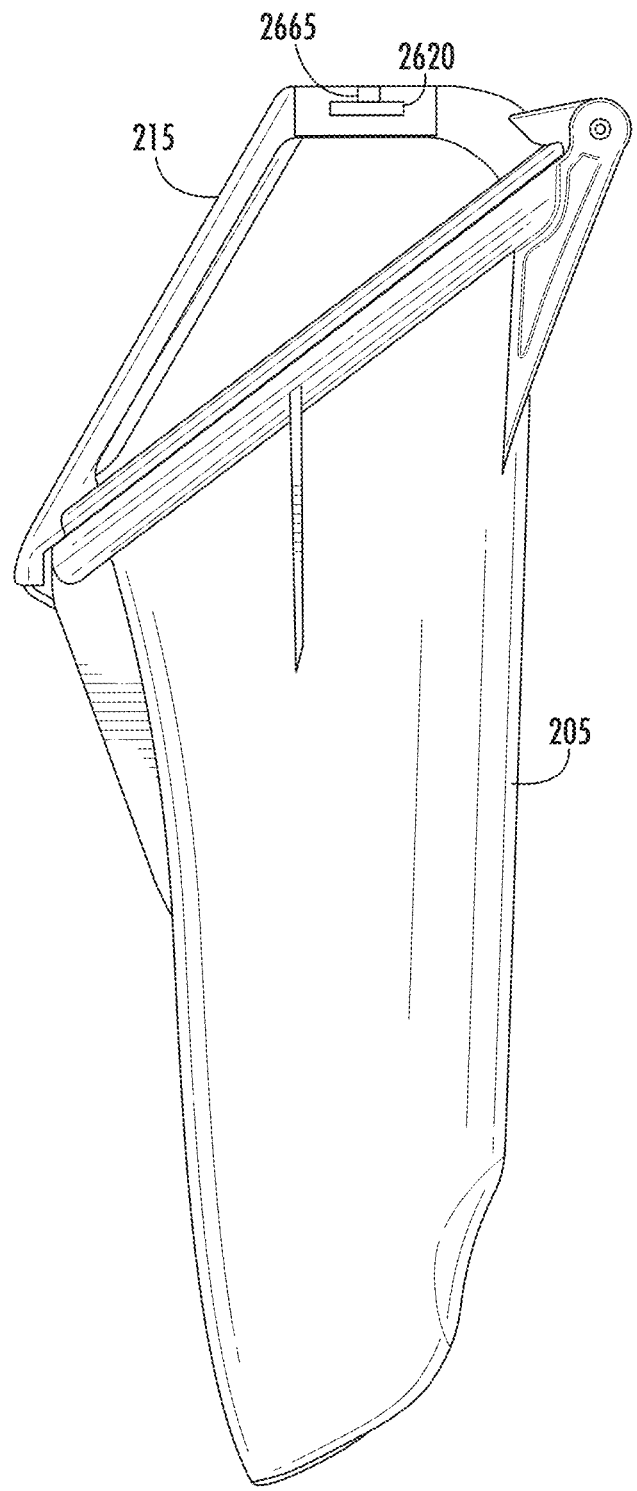
FIG. 32 shows the sheath with the vent material connected to the bottom surface of the lid, in an implementation.

FIG. 32 shows the sheath with the vent material 2620 connected to the bottom surface of the lid, in an implementation. Vent material 1620 is connected to the bottom surface of the top wall and covers the through hole so that gases vent through the vent material and do not go around the vent material. The vent material may be attached to the lid by a variety of techniques, such as epoxy, plastic welding, or other techniques. In alternative implementations, the vent material is connected to a different panel of the lid (e.g., front panel, back panel, or one of the side panels) or is connected to the body of the sheath.

The vent material of the various vent implementations performs the venting function described above. That is, the vent material allows gas to pass from outside of the sheath into the sheath, and to pass from inside of the sheath to outside of the sheath. The vent does not allow bacteria, viruses, prions, pyrogens, water droplets (e.g., hydrophobic to water droplets), or other debris to pass through the vent. The vent material may be a plastic material, a woven material, polytetrafluoroethylene, polyethylene (e.g., low density polyethylene), acrylic, polyester (e.g., 48 gauge PET), another material, or any combination of these materials. In an implementation, the vent material is formed of high density polyethylene fibers, such as Tyvek® 1073B manufactured by DuPont™ of Wilmington, Del. The vent material passes and adheres to the American Society for Testing and Materials (ASTM) protocol F1608, which is a test method for determining whether a material is porous to pathogens. The vent material may also pass and adhere to standards ISO 8536-4, ASTM F838-05, or both, or other similar standards.

In an embodiment, the sheath includes an expansive element. The expansive element may be adapted to expand as the temperature of gas inside the sheath increases and contract as the temperature inside the sheath decreases. The expansive element allows the pressure inside the sheath to remain approximately constant as the gas temperature increases or decreases. The expansive element can include a bellows, a balloon type device, a plunger type device, such as a syringe, or other device. The expansive element is not porous to gas, bacteria, viruses, prions, or other debris and prevents any contaminants in the sheath from reaching a patient and prevents any contaminants outside of the sheath from reaching the system unit inside the sheath.

In an embodiment, the sheath includes an chemical absorber. The chemical absorber can absorb gas inside the sheath as the temperature of the gas increases and can out gas when the temperature of the gas inside the sheath decreases. The chemical absorber can be a chemically reactive material, a porous material, or a combination of these materials.

In an embodiment, the O-ring or a portion of the O-ring is the filter material for a vent system. The O-ring or a portion of the O-ring may be PTFE or other material that is hydrophobic and will allow air to pass through the O-ring but will not allow bacteria, viruses, prions, or other debris to pass through the O-ring.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A housing for an oximeter device comprising:
a lid, wherein the lid comprises a first open end and a first closed end, located opposite to the first open end on the lid, and the first closed end comprises a first window;
a body of the housing, wherein the body comprises a second open end and a second closed end, located opposite to the second open end on the body, and the second closed end comprises a second window;
a hinge, wherein the hinge hinge-couples the lid and body of the housing, the lid comprises a back portion proximal to the hinge and a front portion distal from the hinge and the back portion;

a pad coupled to an inside surface of the lid at the back portion of the lid; and a latch coupled to the lid at the front portion of the lid, wherein the pad is a first distance from the hinge, the latch is a second distance from the hinge, and the first distance is less than the second distance.

2. The housing of claim 1 wherein the hinge is coupled to the lid at the back portion of the lid.

3. The housing of claim 1 wherein the pad has a first elasticity, the lid has a second elasticity, and the first elasticity is higher than the second elasticity.

4. The housing of claim 1 wherein the pad has a first elasticity, the body has a second elasticity, and the first elasticity is higher than the second elasticity.

5. The housing of claim 3 wherein the pad is foam.

6. The housing of claim 1 wherein the latch has a first spring constant, the pad has a second spring constant, and the first spring constant is larger than the second spring constant.

7. The housing of claim 1 wherein the latch applies a first spring force onto a top of the oximeter device when the oximeter device is enclosed in the housing, the pad is coupled to and applies a second spring force onto the top of the oximeter device when the oximeter device is enclosed in the housing, and the first and second spring forces are aligned.

8. The housing of claim 1 wherein the body comprises a first pocket, a pocket wall forms a side surface the first pocket, when the lid is hinge rotated into contact with the body, the latch is in the first pocket, and a top edge of the pocket wall is above an edge of the latch.

9. The housing of claim 8 wherein the body comprises a second pocket that is in the first pocket, when the lid is hinge rotated into contact with the body, a second portion of the latch that is bent is in the second pocket.

10. The housing of claim 1 wherein the second open end has a first side portion, a second side portion, and the first and second side portions are tapered with respect to each other.

11. The housing of claim 10 the first and second side portions are symmetric about a center of the second open end.

12. The housing of claim 10 the second open end is trapezoid-shaped.

13. The housing of claim 1 wherein when the oximeter device is enclosed in the housing, a display of the oximeter device is visible through the first window and a probe face of the oximeter device is coupled to the second window.

* * * * *